US011236167B2

(12) United States Patent
Ulitin et al.

(10) Patent No.: US 11,236,167 B2
(45) Date of Patent: Feb. 1, 2022

(54) MONOCLONAL ANTIBODY TO PD-L1

(71) Applicant: JOINT STOCK COMPANY "BIOCAD", St.Petersburg (RU)

(72) Inventors: Andrei Borisovich Ulitin, Puschino Moskovskaya obl. (RU); Viktoriia Mikhailovna Ekimova, Tyumen (RU); Ekaterina Vladimirovna Sofronova, Resp. Tatarstan (RU); Yulia Sergeevna Chernykh, Permskij krai (RU); Sergei Andreevich Ageev, Moskovskaya obl. (RU); Anna Konstantinovna Vladimirova, St.Petersburg (RU); Aleksei Aleksandrovich Aleksandrov, Perm (RU); Pavel Alekseevich Grebnev, G. Ust'-Ilimsk Irkutskaya Obl. (RU); Valery Vladimirovich Solovyev, Puschino Moskovskaya obl. (RU); Iakov Iurevich Ustiugov, Permskij krai (RU); Pavel Andreevich Iakovlev, St.Petersburg (RU); Timofey Aleksandrovich Nemankin, St.Petersburg (RU); Dmitry Valentinovich Morozov, St.Petersburg (RU)

(*) Notice: Subject to any disclaimer, the term of this patent is extended or adjusted under 35 U.S.C. 154(b) by 0 days.

(21) Appl. No.: 16/605,865

(22) PCT Filed: Apr. 11, 2018

(86) PCT No.: PCT/RU2018/050039
§ 371 (c)(1),
(2) Date: Oct. 17, 2019

(87) PCT Pub. No.: WO2018/194496
PCT Pub. Date: Oct. 25, 2018

(65) Prior Publication Data
US 2020/0369771 A1 Nov. 26, 2020

(30) Foreign Application Priority Data

Apr. 17, 2017 (RU) .......................... RU2017113141

(51) Int. Cl.
*C07K 16/28* (2006.01)
*A61K 39/395* (2006.01)
*A61K 45/06* (2006.01)

(52) U.S. Cl.
CPC .... *C07K 16/2827* (2013.01); *A61K 39/39558* (2013.01); *A61K 45/06* (2013.01); *C07K 2317/51* (2013.01); *C07K 2317/515* (2013.01); *C07K 2317/55* (2013.01); *C07K 2317/56* (2013.01); *C07K 2317/76* (2013.01); *C07K 2317/94* (2013.01)

(58) Field of Classification Search
None
See application file for complete search history.

(56) References Cited

U.S. PATENT DOCUMENTS

| 4,676,980 A | 6/1987 | Segal et al. |
|---|---|---|
| 4,816,567 A | 3/1989 | Cabilly et al. |
| 5,229,275 A | 7/1993 | Goroff |
| 5,500,362 A | 3/1996 | Robinson et al. |
| 5,537,905 A | 7/1996 | Zimmer et al. |
| 5,545,806 A | 8/1996 | Lonberg et al. |
| 5,545,807 A | 8/1996 | Surani et al. |
| 5,565,323 A | 10/1996 | Parker et al. |
| 5,567,610 A | 10/1996 | Borrebaeck et al. |
| 5,569,825 A | 10/1996 | Lonberg et al. |
| 5,571,894 A | 11/1996 | Wells et al. |
| 5,587,458 A | 12/1996 | King et al. |
| 5,591,669 A | 1/1997 | Krimpenfort et al. |
| 5,821,337 A | 10/1998 | Carter et al. |
| 5,869,046 A | 2/1999 | Presta et al. |
| 2013/0323249 A1 | 12/2013 | Zhou et al. |
| 2014/0356353 A1 | 12/2014 | Queva et al. |
| 2015/0203580 A1 | 7/2015 | Papadopoulos et al. |

FOREIGN PATENT DOCUMENTS

| CN | 105777906 A | 7/2016 |
|---|---|---|
| EP | 0003089 A1 | 7/1979 |
| RU | 2011128399 A | 1/2013 |
| WO | 91/00360 A1 | 1/1991 |
| WO | 92/00373 A1 | 1/1992 |
| WO | 93/08829 A1 | 5/1993 |
| WO | 93/16185 A2 | 8/1993 |
| WO | 94/04690 A1 | 3/1994 |
| WO | 97/17852 A1 | 5/1997 |
| WO | 2001/014557 A1 | 3/2001 |
| WO | 2002/086083 A2 | 10/2002 |
| WO | 2007/005874 A2 | 1/2007 |

(Continued)

OTHER PUBLICATIONS

Cancer "Breast Cancer hormone receptor status" accessed from cancer.org on Mar. 19, 2021 (Year: 2021).*
Sui "Anti-PD-1/PD-L1 Therapy for Non-Small-Cell Lung Cancer: Toward Personalized Medicine and Combination Strategies" Journal of Immunology Research vol. 2018, Article ID 6984948, 17 pages (Year: 2018).*
Chen "Enhancement and destruction of antibody function by somatic mutation: unequal occurrence is controlled by V gene combinatorial associations" EMBO 14(12):2784-2794 (Year: 1995).*
Kussie "A Single Engineered Amino Acid Substitution Changes Antibody Fine Specificity" J immunol 152(1):146-52 (Year: 1994).*
PCT/RU 2018/050039 International Search Report dated Nov. 22, 2018—English translation.

(Continued)

*Primary Examiner* — Adam Weidner
(74) *Attorney, Agent, or Firm* — Anglehart et al.

(57) ABSTRACT

The present invention relates to the field of biotechnology and provides antibodies that specifically binds to PD-L1. The invention also relates to DNA encoding said antibodies, to corresponding expression vectors and to methods of producing, and to methods of treatment using said antibodies.

21 Claims, 10 Drawing Sheets
Specification includes a Sequence Listing.

(56) References Cited

FOREIGN PATENT DOCUMENTS

| WO | 2010/036959 A2 | 4/2010 |
|---|---|---|
| WO | 2010/077634 A1 | 7/2010 |
| WO | 2011/066389 A1 | 6/2011 |
| WO | 2013/079174 A1 | 6/2013 |
| WO | 2014/055897 A2 | 4/2014 |
| WO | 2016/022630 A1 | 2/2016 |
| WO | WO 2016/061142 A | 4/2016 |
| WO | 2016/111645 A1 | 7/2016 |
| WO | 2016/149201 A2 | 9/2016 |
| WO | 2017/020291 A1 | 2/2017 |

OTHER PUBLICATIONS

Corresponding European patent application No. 18786945.8 extended search report dated Jan. 13, 2021.
Nishimura et al., Development of Lupus-like Autoimmune Diseases by Disruption of the PD-1 Gene encoding an ITIM Motif-Carrying Immunoreceptor. Immunity. vol. 11, Issue 2, Aug. 1, 1999, pp. 141-151.
Nishimura et al., Autoimmune Dilated Cardiomyopathy in PD-1 Receptor-Deficient Mice. Science. vol. 291, Issue 5502. Jan. 12, 2001.
Freeman et al., Engagement of the Pd-1 Immunoinhibitory Receptor by a Novel B7 Family Member Leads to Negative Regulation of Lymphocyte Activation. J. Exp. Med. 192: 1-9 (2000).
Latchman et al., PD-L2 is a second ligand for PD-1 and inhibits T cell activation. Nature Immunol 2: 261-268 (2001).
Tseng et al., B7-Dc, a New Dendritic Cell Molecule with Potent Costimulatory Properties for T Cells. J. Exp. Med. 193: 839-846 (2001).
Nishimura et al., Developmentally regulated expression of the PD-1 protein on the surface of double-negative(CD4-CD8-) thymocytes. International Immunology, vol. 8, Issue 5, May 1996, pp. 773-780.
Boettler et al., Expression of the Interleukin-7 Receptor Alpha Chain (CD127) on Virus-Specific CD8+ T Cells Identifies Functionally and Phenotypically Defined Memory T Cells during Acute Resolving Hepatitis B Virus Infection. ASM Journals. Journal of Virology. vol. 80, No. 7: 3532-3540 (2006).
Nielsen et al., Alternative splice variants of the human PD-1 gene. Cellular Immunology. vol. 235, Issue 2, Jun. 2005, pp. 109-116 (2005).
Ueda et al., Association of the T-cell regulatory gene CTLA4 with susceptibility to autoimmune disease. Nature 423: 506-511 (2003).
Wan et al., Aberrant Regulation of Synovial T Cell Activation by Soluble Costimulatory Molecules in Rheumatoid Arthritis. The Journal of Immunology. vol. 177, Issue 12. Dec. 15, 2006: 8844-8850 (2006).
Yamazaki et al., Expression of Programmed Death 1 Ligands by Murine T Cells and APC. J. Immunol. 169: 5538-5545 (2002).
Eppihimer et al., Expression and Regulation of the PD-L1 Immunoinhibitory Molecule on Microvascular Endothelial Cells. Microcirculation 9: 133-145 (2002).
Schreiner et al., Interferon-β enhances monocyte and dendritic cell expression of B7-H1 (PD-L1), a strong inhibitor of autologous T-cell activation: relevance for the immune modulatory effect in multiple sclerosis. Journal of Neuroimmunology. vol. 155, Issues 1-2, Oct. 2004, pp. 172-182.
Liu et al., Plasma cells from multiple myeloma patients express B7-H1 (PD-L1) and increase expression after stimulation with IFN-γ and TLR ligands via a MyD88- TRAF6-, and MEK dependent pathway. Blood HO: 296-304 (2007).
Lee et al., Interferon regulatory factor-1 is prerequisite to the constitutive expression and IFN-γ-induced upregulation of B7-H1 (CD274). FEBS Lett, 580: 755-762 (2006).
Parsa et al., Loss of tumor suppressor PTEN function increases B7-H1 expression and immunoresistance in glioma. Nature Medicine vol. 13, pp. 84-88 (2007).

Zhong et al., PD-L2 expression extends beyond dendritic cells/macrophages to B1 cells enriched for VH11/VH12 and phosphatidylcholine binding. Eur. J. Immunol. 37: 2405-2410 (2007).
Liang et al., Regulation of PD-1, PD-L1, and PD-L2 expression during normal and autoimmune responses. Eur. J. Immunol. 33: 2706-2716 (2003).
Loke et al., PD-L1 and PD-L2 are differentially regulated by Th1 and Th2 cells. PNAS 100: 5336-5341: (2003).
Freeman et al., Engagement of the Pd-1 Immunoinhibitory Receptor by a Novel B7 Family Member Leads to Negative Regulation of Lymphocyte Activation. J. Exp. Med. 192: 1027-1034 (2000).
Carter et al., PD-1:PD-L inhibitory pathway affects both CD4+ and CD8+ T cells and is overcome by IL-2. Eur. J. Immunol. 32: 634-643 (2002).
Nguyen et al., Cross-linking the B7 Family Molecule B7-DC Directly Activates Immune Functions of Dendritic Cells. J. Exp. Med. 196: 1393-1398 (2002).
Radhakrishnan et al., Naturally Occurring Human IgM Antibody That Binds B7-DC and Potentiates T Cell Stimulation by Dendritic Cells. J. Immunol. 170: 1830-1838 (2003).
Radhakrishnan et al., Immunotherapeutic Potential of B7-DC (PD-L2) Cross-Linking Antibody In Conferring Antitumor Immunity. Cancer Res. 64: 4965-4972 (2004).
Heckman et al., Retraction: Fast-tracked CTL: Rapid induction of potent anti-tumor killer T cells in situ. Eur. J. Immunol. 37: 1827-1835 (2007).
Radhakrishnan et al., Blockade of Allergic Airway Inflammation Following Systemic Treatment with a B7-Dendritic Cell (PD-L2) Cross-Linking Human Antibody. J. Immunol. 173. 1366-1365 (2004).
Radhakrishnan et al., RETRACTED: Dendritic cells activated by cross-linking B7-DC (PD-L2) block inflammatory airway disease. Journal of Allergy and Clinical Immunology. vol. 116, Issue 3, Sep. 2005, pp. 668-674.
Kuipers et al., Contribution of the PD-1 ligands/PD-1 signaling pathway to dendritic cell-mediated CD4+ T cell activation. Eur. J. Immunol. 36: 2472-2482 (2006).
Butte et al., Programmed Death-1 Ligand 1 Interacts Specifically with the B7-1 Costimulatory Molecule to Inhibit T Cell Responses. Immunity 27: 111-122 (2007).
Latchman et al., PD-L1-deficient mice show that PD-L1 on T cells, antigen-presenting cells, and host tissues negatively regulates T cells. Proc. Natl. Acad. Sci. USA 101: 10691-10696 (2004).
Almagro & Fransson, Humanization of antibodies. Front Biosci. 13:1619-1633 (2008).
Magdelaine-Beuzelin et al., Structure-function relationships of the variable domains of monoclonal antibodies approved for cancer treatment. Critical Reviews in Oncology/Hematology. vol. 64, Issue 3, Dec. 2007, pp. 210-225.
Lefranc et al., IMGT unique numbering for immunoglobulin and T cell receptor variable domains and Ig superfamily V-like domains. Developmental & Comparative Immunology. volume 27, Issue 1, Jan. 2003, pp. 55-77.
Green et al., Antigen-specific human monoclonal antibodies from mice engineered with human Ig heavy and light chain YACs. Nat Genet 1994, 7:13-21.
Clynes et al. Fc receptors are required in passive and active immunity to melanoma. PNAS (USA) 95: 652-656 (1998).
Gazzano-Santoro et al., A non-radioactive complement-dependent cytotoxicity assay for anti-CD20 monoclonal antibody. Journal of Immunological Methods. vol. 202, Issue 2, Mar. 28, 1997, pp. 163-171.
Skerra et al., Bacterial expression of immunoglobulin fragments. Current Opinion in Immunology. vol. 5, Issue 2, 1993, pp. 256-262.
Pluckthun, Mono- and Bivalent Antibody Fragments Produced in *Escherichia coli*: Engineering, Folding and Antigen Binding. Immunol. Revs. 130, 1992, pp. 151-188.
Clackson et al., Making antibody fragments using phage display libraries. Nature, 352, 1991, pp. 624-628.
Marks et al., By-Passing Immunization: Building High Affinity Human Antibodies by Chain Shuffling. Bio/Technology vol. 10, pp. 779-783 (1992).

(56) References Cited

OTHER PUBLICATIONS

Waterhouse, et al., 1993. Combinatorial infection and in vivo recombination: a strategy for making large phage antibody repertoires. Nucleic Acid Research 21: 2265-2266.

Morrison, et al., Chimeric human antibody molecules: mouse antigen-binding domains with human constant region domains. Proc. Natl. Acad. Sci. USA: 81, 1984, p. 6851.

Jones et al., Replacing the complementarity-determining regions in a human antibody with those from a mouse. Nature, 321, 1986, pp. 522-525.

Verhoeyen et al., Reshaping human antibodies: grafting an antilysozyme activity. Science, 239, 1988, pp. 1534-1536.

Carter et al., Humanization of an anti-p185HER2 antibody for human cancer therapy. Proc. Natl. Acad. Sci. USA: 89, 1992, p. 4285-4289.

Jakobovits et al., Analysis of homozygous mutant chimeric mice: deletion of the immunoglobulin heavy-chain joining region blocks B-cell evleopment and antibody production. Proc. Natl. Acad. Sci. USA: 90, 1993, p. 2551.

Griffith et al., Human anti-self antibodies with high specificity from phage display libraries. EMBO J., 12, 1993, pp. 725-734.

Morimoto et al., Single-step purification of F(ab')2 fragments of mouse monoclonal antibodies (immunoglobulins G1) by hydrophobic interaction high performance liquid chromatography using TSKgel Phenyl-5PW. Journal of Biochemical and Biophysical Methods 24, 1992, pp. 107-117.

Brennan et al., Preparation of bispecific antibodies by chemical recombination of monoclonal immunoglobulin G1 fragments. Science, 229, 1985, p. 81-83.

Carter et al., High Level *Escherichia coli* Expression and Production of a Bivalent Humanized Antibody Fragment. Bio/Technology, 10, 1992, pp. 163-167.

Millstein et al., Hybrid hybridomas and their use in immunohistochemistry. Nature, 305, 1983, pp. 537-540.

Traunecker et al., Bispecific single chain molecules (Janusins) target cytotoxic lymphocytes on HIV infected cells. EMBO J, 10, 1991, pp. 3655-3659.

Suresh et al., Bispecific monoclonal antibodies from hybrid hybridomas. Methods in Enzymology, 121, 1986, p. 210-228.

Shalaby et al., Development of humanized bispecific antibodies reactive with cytotoxic lymphocytes and tumor cells overexpressing the HER2 protooncogene. J. Exp. Med., 175, 1992, pp. 217-225.

Kostelny et al., Formation of a bispecific antibody by the use of leucine zippers, J. Immunol., 148(5), 1992, pp. 1547-1553.

Hollinger et al., "Diabodies": small bivalent and bispecific antibody fragments. Proc Natl Acad Sci 1993; 90: 6444-6448.

Lonberg et al., Antigen-specific human antibodies from mice comprising four distinct genetic modifications. Nature 1994, 368:856-859.

Dong et al., B7-H1, a third member of the B7 family, co-stimulates T-cell proliferation and interleukin-10 secretion. Nature Med. 5: 1365-1369 (1999).

Keir et al., PD-1 and Its Ligands in Tolerance and Immunity. Annual Review of Immunology. vol. 26:677-704 (Volume publication date Apr. 2008). First published online as a Review in Advance on Jan. 2, 2008.

Capel et al., Heterogeneity of Human IgG Fc Receptors. Immunomethods 4: 25-34 (1994).

Ravetch and Kinet, Fc Receptors. Annual Review of Immunology. vol. 9:457-492 (Volume publication date Apr. 1991).

Daëron, Fc Receptor Biology. Annu. Rev. Immunol. 15: 203-234 (1997).

McCafferty et al., Phage antibodies: filamentous phage displaying antibody variable domains. Nature, 348, 1990, pp. 552-554.

Marks et al., By-passing immunization: Human antibodies from V-gene libraries displayed on phage. Journal of Molecular Biology. vol. 222, Issue 3, Dec. 5, 1991, pp. 581-597.

Chothia et al., Canonical structures for the hypervariable regions of immunoglobulins. Journal of Molecular Biology. vol. 196, Issue 4, Aug. 20, 1987, pp. 901-917.

Johnson Kevin S. and Chiswell David J., Human antibody engineering: Current Opinion in Structural Biology 1993, 3:564-571. Current Opinion in Structural Biology, 3, 1993, pp. 564-571.

Presta et al., Humanization of an antibody directed against IgE. J. Immunol., 151, 1993, p. 2623.

Riechmann et al., Reshaping human antibodies for therapy. Nature, 332, 1988, pp. 323-327.

Guyer et al., Immunoglobulin VBinding by Mouse Intestinal Epithelial Cell Receptors. J. Immunol. 117: 587 (1976) (Abstract).

Kohler et al., Continuous cultures of fused cells secreting antibody of predefined specificity. Nature vol. 256, pp. 495-497 (1975).

Sims et al., A humanized CD18 antibody can block function without cell destruction. J Immunol Aug. 15, 1993, 151 (4) 2296-2308 (Abstract).

Gruber et al., Efficient tumor cell lysis mediated by a bispecific single chain antibody expressed in *Escherichia coli*.J. Immunol, 152, 1994, p. 5368 (Abstract).

Tutt et al., Trispecific F(ab')3 derivatives that use cooperative signaling via the TCR/CD3 complex and CD2 to activate and redirect resting cytotoxic T cells. J. Immunol., 147, 1991, p. 60-69 (Abstract).

\* cited by examiner

| Antibody | FcRn | FcgRIa | FcgRIIIaV |
|---|---|---|---|
| BCD-135 | 1.69E-08 | - | - |
| Atezolizumab | 1.45E-08 | - | - |

| Antigen | Concentration (nM) | Kd (M) |
|---|---|---|
| Human PDL1 | 9.62 | <1.0E-12 |
| Cynomolgus PDL1 | 19.2 | 5.55E-10 |

| Concentration in 100% human serum | Calculated concentration µg/ml | Measured concentration µg/ml | Decrease, fold |
|---|---|---|---|
| 4 µg/ml, control | 4 | >10 | <0.40 |
| 20 µg/ml, control | 20 | 26,2 | 0.77 |
| 100 µg/ml, control | 100 | 98,4 | 1.02 |
| 4 µg/ml, 7 days 37° C | 4 | 9,1 | 0.44 |
| 20 µg/ml, 7 days 37°C | 20 | 34,7 | 0.58 |
| 100 µg/ml, 7 days 37°C | 100 | 114,3 | 0.87 |

SEQUENCE LISTING

```
<160> NUMBER OF SEQ ID NOS: 10

<210> SEQ ID NO 1
<211> LENGTH: 5
<212> TYPE: PRT
<213> ORGANISM: Artificial Sequence
<220> FEATURE:
<223> OTHER INFORMATION: Synthesized Sequence

<400> SEQUENCE: 1

Asp Tyr Ala Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Synthesized Sequence

<400> SEQUENCE: 2

Asp Ile Ser Trp Ser Gly Ser Asn Thr Asn Tyr Ala Asp Ser Val Lys
1               5                   10                  15

Gly

<210> SEQ ID NO 3
<211> LENGTH: 13
<212> TYPE: PRT
<213> ORGANISM: Artificial Sequence
<220> FEATURE:
<223> OTHER INFORMATION: Synthesized Sequence

<400> SEQUENCE: 3

Ala Pro Leu Leu Leu Ala Met Thr Phe Gly Val Gly Ser
1               5                   10

<210> SEQ ID NO 4
<211> LENGTH: 122
<212> TYPE: PRT
<213> ORGANISM: Artificial Sequence
```

```
<220> FEATURE:
<223> OTHER INFORMATION: Synthesized Sequence

<400> SEQUENCE: 4

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Asp Ile Ser Trp Ser Gly Ser Asn Thr Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Ala Pro Leu Leu Leu Ala Met Thr Phe Gly Val Gly Ser Trp
            100                 105                 110

Gly Gln Gly Thr Leu Val Thr Val Ser Ser
        115                 120

<210> SEQ ID NO 5
<211> LENGTH: 14
<212> TYPE: PRT
<213> ORGANISM: Artificial Sequence
<220> FEATURE:
<223> OTHER INFORMATION: Synthesized Sequence

<400> SEQUENCE: 5

Gly Leu Ser Ser Gly Thr Val Thr Ala Ile Asn Tyr Pro Gly
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Synthesized Sequence

<400> SEQUENCE: 6

Asn Thr Asn Thr Arg His Ser
1               5

<210> SEQ ID NO 7
<211> LENGTH: 10
<212> TYPE: PRT
<213> ORGANISM: Artificial Sequence
<220> FEATURE:
<223> OTHER INFORMATION: Synthesized Sequence

<400> SEQUENCE: 7

Ala Leu Tyr Met Gly Asn Gly Gly His Met
1               5                   10

<210> SEQ ID NO 8
<211> LENGTH: 106
<212> TYPE: PRT
<213> ORGANISM: Artificial Sequence
<220> FEATURE:
<223> OTHER INFORMATION: Synthesized Sequence

<400> SEQUENCE: 8

Gln Thr Val Val Thr Gln Glu Pro Ser Leu Ser Val Ser Pro Gly Gly
```

```
            1               5                  10                 15
          Thr Val Thr Leu Thr Cys Gly Leu Ser Ser Gly Thr Val Thr Ala Ile
                          20                 25                 30

Asn Tyr Pro Gly Trp Tyr Gln Gln Thr Pro Gly Gln Ala Pro Arg Thr
                          35                 40                 45

Leu Ile Tyr Asn Thr Asn Thr Arg His Ser Gly Val Pro Asp Arg Phe
                          50                 55                 60

Ser Gly Ser Ile Ser Gly Asn Lys Ala Ala Leu Thr Ile Thr Gly Ala
           65                 70                 75                 80

Gln Ala Glu Asp Glu Ala Asp Tyr Tyr Cys Ala Leu Tyr Met Gly Asn
                          85                 90                 95

Gly Gly His Met Phe Gly Gly Gly Thr Lys
                          100                105

<210> SEQ ID NO 9
          <211> LENGTH: 452
          <212> TYPE: PRT
          <213> ORGANISM: Artificial Sequence
          <220> FEATURE:
          <223> OTHER INFORMATION: Synthesized Sequence

<400> SEQUENCE: 9

Glu Val Gln Leu Val Glu Ser Gly Gly Gly Val Val Arg Pro Gly Gly
           1               5                  10                 15

Ser Leu Arg Leu Ser Cys Ala Ala Ser Gly Phe Thr Phe Asp Asp Tyr
                          20                 25                 30

Ala Met Ser Trp Val Arg Gln Ala Pro Gly Lys Gly Leu Glu Trp Val
                          35                 40                 45

Ser Asp Ile Ser Trp Ser Gly Ser Asn Thr Asn Tyr Ala Asp Ser Val
                          50                 55                 60

Lys Gly Arg Phe Thr Ile Ser Arg Asp Asn Ala Lys Asn Ser Leu Tyr
           65                 70                 75                 80

Leu Gln Met Asn Ser Leu Arg Ala Glu Asp Thr Ala Leu Tyr His Cys
                          85                 90                 95

Ala Arg Ala Pro Leu Leu Leu Ala Met Thr Phe Gly Val Gly Ser Trp
                          100                105                110

Gly Gln Gly Thr Leu Val Thr Val Ser Ser Ala Ser Thr Lys Gly Pro
                          115                120                125

Ser Val Phe Pro Leu Ala Pro Ser Ser Lys Ser Thr Ser Gly Gly Thr
                          130                135                140

Ala Ala Leu Gly Cys Leu Val Lys Asp Tyr Phe Pro Glu Pro Val Thr
          145                 150                155                160

Val Ser Trp Asn Ser Gly Ala Leu Thr Ser Gly Val His Thr Phe Pro
                          165                170                175

Ala Val Leu Gln Ser Ser Gly Leu Tyr Ser Leu Ser Ser Val Val Thr
                          180                185                190

Val Pro Ser Ser Ser Leu Gly Thr Gln Thr Tyr Ile Cys Asn Val Asn
                          195                200                205

His Lys Pro Ser Asn Thr Lys Val Asp Lys Arg Val Glu Pro Lys Ser
                          210                215                220

Cys Asp Lys Thr His Thr Cys Pro Pro Cys Pro Ala Pro Glu Ala Ala
          225                 230                235                240

Gly Gly Pro Ser Val Phe Leu Phe Pro Pro Lys Pro Lys Asp Thr Leu
                          245                250                255

Met Ile Ser Arg Thr Pro Glu Val Thr Cys Val Val Val Asp Val Ser
```

```
              260                 265                 270
His Glu Asp Pro Glu Val Lys Phe Asn Trp Tyr Val Asp Gly Val Glu
                275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445

Ser Pro Gly Lys
        450

<210> SEQ ID NO 10
<211> LENGTH: 216
<212> TYPE: PRT
<213> ORGANISM: Artificial Sequence
<220> FEATURE:
<223> OTHER INFORMATION: Synthesized Sequence

<400> SEQUENCE: 10

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Thr Val Thr Ala Ile
            20                  25                  30

Asn Tyr Pro Gly Trp Tyr Gln Gln Thr Pro Gly Gln Ala Pro Arg Thr
        35                  40                  45

Leu Ile Tyr Asn Thr Asn Thr Arg His Ser Gly Val Pro Asp Arg Phe
    50                  55                  60

Ser Gly Ser Ile Ser Gly Asn Lys Ala Ala Leu Thr Ile Thr Gly Ala
65                  70                  75                  80

Gln Ala Glu Asp Glu Ala Asp Tyr Tyr Cys Ala Leu Tyr Met Gly Asn
                85                  90                  95

Gly Gly His Met Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
```

-continued

```
                165                 170                 175
Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

MONOCLONAL ANTIBODY TO PD-L1

FIELD OF THE INVENTION

The present invention relates to the field of biotechnology, in particular to antibodies or antigen-binding fragments thereof and use thereof. More specifically, the present invention relates to a monoclonal antibody that specifically binds to PD-L1 (CD274, B7-H1, programmed death ligand-1). The invention also relates to a nucleic acid encoding the antibody or antigen-binding fragment thereof, an expression vector, a method for producing the antibody, and use of the antibody for enhancing the T-cell function to upregulate cell-mediated immune responses and to treat T-cell dysfunction associated disorders, e.g. tumour immunity, and to treat cancer.

BACKGROUND OF THE INVENTION

Lymphocyte Development and Activation

The two major types of lymphocytes in humans are T (thymocytes) and B (bone marrow-derived). These cells are derived from hematopoietic stem cells in the bone marrow and fetal liver that are programmed to the lymphoid development pathway. The progeny of these stem cells follow divergent pathways to mature into either B or T lymphocytes. Human B-lymphocyte development takes place entirely within the bone marrow. T-cells, on the other hand, develop from immature precursors that leave the bone marrow and travel through the bloodstream to the thymus, where they proliferate and differentiate into mature T-lymphocytes.

Mature lymphocytes that emerge from the thymus or bone marrow are in a quiescent, or "resting" state, i.e., they are mitotically inactive. When dispersed into the bloodstream, these "virgin" or "naive" lymphocytes travel into various secondary or peripheral lymphoid organs, such as the spleen, lymph nodes or tonsils. Most virgin lymphocytes are characterized by an inherently short lifespan and die without a few days after leaving the bone marrow or thymus. However, if such a cell receives signals indicating the presence of an antigen, it may be activated and undergo successive rounds of cell division. Some cells of the resulting progeny then revert to the resting state and become memory lymphocytes—B- and T-cells that are essentially primed for the next encounter with the stimulating allergen. The other progeny of activated naive lymphocytes are effector cells that live for only a few days but perform specific defensive activities.

Lymphocyte activation is an ordered series of events through which a resting lymphocyte passes once it is stimulated to divide and produce progeny, some of which become effector cells. A full response includes both the induction of cell proliferation (mitogenesis) and the expression of immunologic functions. Lymphocytes become activated when specific ligands bind to receptors on their surfaces. The ligands are different from T-cells and B-cells, but the resulting intracellular physiological mechanisms are similar.

Some foreign antigens themselves can induce lymphocyte activation, particularly large polymeric antigens that cross-link surface immunoglobulins on B-cells, or other glycoproteins on T-cells. However, most antigens are not polymeric, and even direct binding to B-cells in large numbers fail to result in activation. These more common antigens activate B-cells when they are co-stimulated with nearby activated helper T-lymphocytes. Such stimulation may occur from lymphokines secreted by the T-cell but is transmitted most efficiently by direct contact of the B-cell with T-cell surface proteins that interact with certain B-cell surface receptors to generate a secondary signal.

T-Cells

T lymphocytes do not express immunoglobulins, but instead, detect the presence of foreign substances through surface proteins called T-cell receptors (TCR). These receptors recognize antigens by either direct contact or through influencing the activity of other immune cells. Together with macrophages, T-cells are the primary cell type involved in the cell-mediated immunity.

Unlike B-cells, T-cells can detect foreign substances only in specific conditions. In particular, T-lymphocytes recognize a foreign protein only if it is first cleaved into small peptides, which are then displayed on the surface of a second host cell, called an antigen-presenting cell (APC). Many types of host cells can present antigens under some conditions but certain types are more specifically adapted for this and are particularly important for regulation of the T-cell activity, including macrophages and other B-cells. Antigen presentation depends in part on specific proteins, called major histocompatibility complex (MHC) proteins, on the surface of the presenting cells. Thus, to stimulate cell-mediated immunity, foreign peptides must be presented to T-cells in combination with MHC peptides, and this combination must be recognized by a T-cell receptor.

There are two significant T-cell subsets: cytotoxic T-lymphocytes (Tc-cells or CTLs) and helper T ($T_H$) cells, which can roughly be identified on the basis of cell surface expression of the marker CD8 and CD4. Tc-cells are important in viral defence and can kill viruses directly by recognizing certain cell surface expressed viral peptides. $T_H$ cells promote proliferation, maturation and immunologic function of other cell types, e.g. lymphokine secretion to control the activity of B-cells, macrophages and cytotoxic T-cells. Both naive and memory T-lymphocytes normally remain in the resting state, and in this state, they do not exhibit significant helper or cytotoxic activity. In the activated state, these cells undergo several rounds of mitotic division to produce daughter cells. Some of these daughter cells return to the resting state as memory cells, but others become effector cells that actively exhibit helper or cytotoxic activity. These daughter cells are similar to their parents: CD4+ cells can only product CD4+ progeny, and CD8+ cells yield only CD8+ progeny. Effector T-cells express cell surface markers that are not expressed on resting T-cells, such as CD25, CD28, CD29, CD40L, transferrin receptors and class II MHC proteins. Without the activating stimuli, cytotoxic or helper activity gradually subsides over several days as the effector cells either die or revert to the resting state.

Similar to B-cell activation, T-lymphocyte response to most antigens also requires two types of simultaneous stimuli. The first is the antigen, which is appropriately displayed by MHC proteins on an antigen-presenting cell, can be recognized and bound by T-cell receptors. While this antigen-MHC complex does not send a signal into the cell interior, it is usually insufficient to result in T-cell activation. Full activation, such as the one occurs with helper T-cells, requires co-stimulation with other specific ligands called co-stimulators that are expressed on the surface of the antigen-presenting cell. On the other hand, cytotoxic T-cell activation generally requires IL-2—a cytokine secreted by activated helper T-cells.

PD-1 Pathway

An important negative co-stimulatory signal regulating T-cell activation is provided by programmed death-1 receptor (PD-1, CD279), and its ligand binding partners PD-L1

(B7-H1, CD274) and PD-L2 (B7-DC, CD273). The negative regulatory role of PD-1 was revealed by PD-1 knockouts (Pdcd1$^{-/-}$), which are prone to autoimmunity. (Nishimura et al, Immunity JJ: 141-51 (1999); Nishimura et al, Science 291: 319-22 (2001)). PD-1 is related to CD28 and CTLA-4 but lacks the membrane proximal cysteine that allows homodimerization. The cytoplasmic domain of PD-1 contains an immunoreceptor tyrosine-binding inhibition motif (ITIM, V/IxYxxL/V). PD-1 only binds to PD-L1 and PD-L2 (Freeman et al, J. Exp. Med. 192: 1-9 (2000); Dong et al, Nature Med. 5: 1365-1369 (1999); Latchman et al, Nature Immunol 2: 261-268 (2001); Tseng et al, J. Exp. Med. 193: 839-846 (2001)).

PD-1 can be expressed on T-cells, B-cells, natural killer T-cells, activated monocytes and dendritic cells (DCs). PD-1 is expressed by activated, but not by unstimulated human CD4$^+$ and CD8$^+$ T-cells, B-cells and myeloid cells. This discriminates it from the more restricted expression of CD28 and CTLA-4 (Nishimura et al, Int. Immunol. 8: 773-80 (1996); Boettler et al, J. Virol. 80: 3532-40 (2006)). There are at least 4 variants of PD-1 that have been cloned from activated human T-cells, including transcripts lacking (i) exon 2, (ii) exon 3, (iii) exons 2 and 3 or (iv) exons 2 through 4 (Nielsen et al, Cell. Immunol. 235: 109-16 (2005)). With the exception of PD-1Δex3, all variants are expressed at similar levels as full-length PD-1 in resting peripheral blood mononuclear cells (PBMCs). Expression of all variants is significantly induced upon activation of human T-cells with anti-CD3 and anti-CD28 antibodies. The PD-1Δex3 variants lack a transmembrane domain and are similar to soluble CTLA-4, which plays an important role in autoimmunity (Ueda et al, Nature 423: 506-11 (2003)). This variant is enriched in the synovial fluid and serum of patients with rheumatoid arthritis (Wan et al, J. Immunol. 177: 8844-50 (2006)). The two PD-1 ligands differ in their expression patterns. PD-L1 is constitutively expressed on mouse T- and B-cells, CDs, macrophages, mesenchymal stem cells and bone marrow-derived mast cells (Yamazaki et al, J. Immunol. 169: 5538-45 (2002)). PD-L1 is expressed on multiple nonhematopoietic cells (e.g., cornea, lung, vascular epithelium, liver nonparenchymal cells, mesenchymal stem cells, pancreatic islets, placental syncytiotrophoblasts, keratinocytes, etc.) [Keir et al, Annu. Rev. Immunol. 26: 677-704 (2008)], and is upregulated on multiple cell types after activation. Both type I and type II interferons, IFNs, upregulate PD-L1 (Eppihimer et al, Microcirculation 9: 133-45 (2002)); Schreiner et al, J. Neuroimmunol 155: 172-82 (2004). PD-L1 expression in cell lines is decreased when MyD88, TRAF6 and MEK are inhibited (Liu et al, Blood HO: 296-304 (2007)). JAK2 has also been involved in PD-L1 induction (Lee et al, FEBS Lett, 580: 755-62 (2006); Liu et al, Blood HO: 296-304 (2007)). Loss or inhibition of phosphatase and tensin homolog (PTEN), a cellular phosphatase that modifies phosphatidylinositol 3-kinase (PI3K) and Akt signalling increased post-transcriptional PD-L1 expression in cancer (Parsa et al, Nat. Med. 13: 84-88 (2007)).

The PD-L2 expression is more restricted than PD-L1. PD-L2 is inducibly expressed on DCs, macrophages, and bone marrow-derived mast cells. PD-L2 is also expressed on about half to two-thirds of resting peritoneal B1-cells, but not on conventional B2 B-cells (thong et al, Eur. J. Immunol. 37: 2405-10 (2007)). PD-L2+B1 cells bind phosphatidylcholine and may be important for an innate immune response against bacterial antigens. Induction of PD-L2 by IFN-γ is partially dependent upon NF-KB (Liang et al, Eur. J. Immunol. 33_: 2706-16 (2003)). PD-L2 can also be induced on monocytes and macrophages by GM-CF, IL-4 and IFN-γ (Yamazaki et al., J. Immunol. 169: 5538-45 (2002); Loke et al, PNAS 100: 5336-41 (2003)).

PD-1 signalling typically has a greater effect on cytokine production than on cellular proliferation, with a significant effect on IFN-γ, TNF-α and IL-2 production. PD-1 mediated inhibitory signalling also depends on the strength of the TCR signalling, the greater inhibition being provided at low levels of TCR stimulation. This reduction can be overcome by co-stimulation through CD28 [Freeman et al, J. Exp. Med. 192: 1027-34 (2000)] or the presence of IL-2 [Carter et al, Eur. J. Immunol. 32: 634-43 (2002)].

There are a growing number of evidence that signalling through PD-L1 and PD-L2 may be bidirectional. That is, in addition to modifying TCR or BCR signalling, the signal may also be delivered back to the cells expressing PD-L1 and PD-L2. While treatment of dendritic cells with a naturally human anti-PD-L2 antibody isolated from a patient with Waldenstrom's macroglobulinemia was not found to upregulate MHC II or B7 costimulatory molecules, such cells produced greater amount of proinflammatory cytokines, particularly TNF-α and IL-6, and stimulated T-cell proliferation (Nguyen et al, J. Exp. Med. 196: 1393-98 (2002)). Mice treatment with this antibody also (1) enhanced resistance to transplanted b16 melanoma and rapidly induced tumor-specific CTL (Radhakrishnan et al, J. Immunol. 170: 1830-38 (2003); Radhakrishnan et al, Cancer Res. 64: 4965-72 (2004); Heckman et al, Eur. J. Immunol. 37: 1827-35 (2007)); (2) blocked development of airway inflammatory disease in a mouse model of allergic asthma (Radhakrishnan et al, J. Immunol. 173: 1360-65 (2004); Radhakrishnan et al, J. Allergy Clin. Immunol. UJy. 668-74 (2005)).

One more evidence of reverse signaling into dendritic cells ("DCs") was obtained from the studies of bone marrow-derived DCs cultured with soluble PD-1 (PD-1 EC domain fused to Ig constant region—"s-PD-1") (Kuipers et al, Eur. J. Immunol. 36: 2472-82 (2006)). This sPD-1 inhibited DC activation and increased IL-10 production, in a reversible manner through the administration of anti-PD-1. Additionally, several studies identified a receptor for PD-L1 or PD-L2 that is independent of PD-1. B7.1 has already been identified as a binding partner for PD-L1 (Butte et al, Immunity 27: 111-22 (2007)). Chemical cross-linking studies show that PD-L1 and B7.1 may interact through their IgV-like domains. B7.1:PD-L1 interactions can induce an inhibitory signalling into T-cells. Ligation of PD-L1 on CD4+ T-cells by B7.1 or ligation of B7.1 on CD4+ T-cells by PD-L1 provides an inhibitory signal. T-cells lacking CD28 and CTLA-4 show decreased proliferation and cytokine production when stimulated by anti-CD3 plus B7.1 coated beads. In T-cells lacking all the receptors for B7.1 (i.e., CD28, CTLA-4 and PD-L1), T-cell proliferation and cytokine production were no longer inhibited by anti-CD3 plus B7.1 coated beads. This indicates that B7.1 acts specifically through PD-L1 on the T-cell in the absence of CD28 and CTLA-4. Similarly, T-cells lacking PD-1 showed decreased proliferation and cytokine production when stimulated in the presence of anti-CD3 plus PD-L1 coated beads, demonstrating the inhibitory effect of PD-L1 ligation on B7.1 on T-cells. When T-cells lacking all known receptors for PD-L1 (i.e., no PD-1 and B7.1), T-cell proliferation was no longer impaired by anti-CD3 plus PD-L1 coated beads. Thus, PD-L1 can exert an inhibitory effect on T-cells either through B7.1 or PD-1.

The direct interaction between B7.1 and PD-L1 indicates that the current understanding of costimulation is incomplete, and underscores the significance for the expression of these molecules on T-cells. Studies of PD-L1$^{-/-}$ T-cells show that PD-L1 on T-cells can downregulate cytokine production by T-cell. (Latchman et al, Proc. Natl. Acad. Sci. USA 101: 10691-96 (2004)). Because both PD-L1 and B7.1 are expressed on T-cells, B-cells, DCs and macrophages, there is the potential for directional interactions between B7.1 and PD-L1 on these cells types. Additionally, PD-L1 on nonhematopoietic cells may interact with B7.1 as well as PD-1 on T-cells, raising the question of whether PD-L1 is involved in their regulation. One possible explanation for the inhibitory effect of B7.1: PD-L1 interaction is that T-cell PD-L1 may trap or isolate APC B7.1 from interaction with CD28.

As a result, the antagonism of signalling through PD-L1, including blocking PD-L1 from interacting with either PD-1, B7.1 or both, thereby preventing PD-L1 from sending a negative co-stimulatory signal to T-cells and other antigen presenting cells is likely to enhance immunity in response to infection (e.g., acute and chronic) and tumour immunity. In addition, the anti-PD-L1 antibodies of the present invention may be combined with antagonists of other components of PD-1: PD-L1 signalling, for example, an antagonist of anti-PD-1 and anti-PD-L2 antibodies.

In particular, the inhibition of PD-L1 signalling has been proposed as a means to enhance T-cell immunity for the treatment of cancer (e.g., tumour immunity) and infections, including both acute and chronic (e.g., persistent) infections.

Inhibitors blocking the PD-L1: PD-1 interaction are known from, inter alia, WO2001014557, WO2002086083, WO2007005874, WO2010036959, WO2010077634, and WO2011066389.

Currently, in the early stage clinical trials, there are more than 10 mono- and bispecific drugs with an anti-PD-L1 component.

One monospecific anti-PD-L1 antibody, MPDL3280A (atezolizumab, Roche), has successfully passed clinical trials (CT) and is used in clinical practice. Athezolizumab has been approved by the FDA for use in patients with metastatic urothelial cancer; III phase CTs are continued in patients with non-small cell lung cancer (NSCLC), renal cell carcinoma, colorectal cancer (CRC), and breast cancer (BC). The preparation is an Ig1 antibody with a modified Fc-region (to eliminate the ADCC effect). Athezolizumab is described in WO2010077634.

Other anti-PD-L1 preparations in the final phase CT are avelumab (Pfizer) and durvalumab (AZ) preparations. Durvalumab (MEDI-4736) is described in WO2011066389. Avelumab is described in WO2013079174. The main difference of Avelumab preparation is the presence of the ADCC effect in the antibody, moreover, it can be enhanced with IFNg or IL12 (NCT01772004). In addition, the safety profile of the Avelumab preparation corresponds to that of other anti-PD-1/PD-L1 preparations (Cancer Immunol Res; 3(10) October 2015; Antibody-Dependent Cellular Cytotoxicity Activity of a Novel Anti-PD-L1 Antibody Avelumab on Human Tumor Cells; Benjamin Boyerinas).

Thus, there is a need to provide an effective inhibitor of PD-L1 (programmed death ligand-1)

In reference to the above, of great importance is to provide new antibodies that effectively bind to PD-L1.

The BCD-135 antibody selectively binds to PD-L1 and is an effective inhibitor of the programmed death ligand-1.

SUMMARY OF THE INVENTION

The present invention relates to binding molecules, in particular to antibodies that directed to bind PD-L1. Such antibodies can be used to treat a disease or disorder mediated by PD-L1.

In one aspect, the present invention relates a monoclonal antibody or an antigen-binding fragment thereof that specifically binds to PD-L1 comprising a heavy chain variable domain comprising an amino acid sequence that is at least 90% identical to SEQ ID NO: 3 and a light chain variable domain comprising an amino acid sequence that is at least 90% identical to SEQ ID NO: 7.

In some embodiments, the monoclonal antibody or the antigen-binding fragment thereof comprises a heavy chain variable domain comprising the amino acid sequence of SEQ ID NO: 3.

In some embodiments, the monoclonal antibody or the antigen-binding fragment thereof comprises a light chain variable domain comprising the amino acid sequence of SEQ ID NO: 7.

In some embodiments, the monoclonal antibody or the antigen-binding fragment thereof comprises a heavy chain variable domain comprising amino acid sequences that is at least 90% identical to SEQ ID NOs: 1-3.

In some embodiments, the monoclonal antibody or the antigen-binding fragment thereof comprises a heavy chain variable domain comprising the amino acid sequences of SEQ ID NOs: 1-3.

In some embodiments, the monoclonal antibody or the antigen-binding fragment thereof comprises a light chain variable domain comprising amino acid sequences that is at least 90% identical to SEQ ID NOs: 5-7.

In some embodiments, the monoclonal antibody or the antigen-binding fragment thereof comprises a light chain variable domain comprising the amino acid sequences of SEQ ID NOs: 5-7.

In some embodiments, the monoclonal antibody or the antigen-binding fragment thereof comprises a heavy chain variable domain comprising amino acid sequences that is at least 90%, identical to SEQ ID NOs: 1-3, and a light chain variable domain comprising amino acid sequences that is at least 90% identical to SEQ ID NOs: 5-7.

In some embodiments, the monoclonal antibody or the antigen-binding fragment thereof comprises a heavy chain variable domain comprising the amino acid sequences of SEQ ID NO: 1-3, and a light chain variable domain comprising the amino acid sequences of SEQ ID NOs: 5-7.

In some embodiments, the monoclonal antibody or the antigen-binding fragment thereof comprises a heavy chain variable domain comprising an amino acid sequence that is at least 90% identical to SEQ ID NO: 4.

In some embodiments, the monoclonal antibody or the antigen-binding fragment thereof comprises a heavy chain variable domain comprising the amino acid sequence of SEQ ID NO: 4.

In some embodiments, the monoclonal antibody or the antigen-binding fragment thereof comprises a light chain variable domain comprising an amino acid sequence that is at least 90% identical to SEQ ID NO: 8.

In some embodiments, the monoclonal antibody or the antigen-binding fragment thereof comprises a light chain variable domain comprising the amino acid sequence of SEQ ID NO: 8.

In some embodiments, the monoclonal antibody or the antigen-binding fragment thereof comprises a heavy chain variable domain comprising an amino acid sequence that is at least 908 identical to SEQ ID NO: 4, and a light chain variable domain comprising an amino acid sequence that is at least 90% identical to SEQ ID NO: 8.

In some embodiments, the monoclonal antibody or the antigen-binding fragment thereof comprises a heavy chain variable domain comprising the amino acid sequence of SEQ ID NO: 4, and a light chain variable domain comprising the amino acid sequence of SEQ ID NO 8.

In some embodiments, the monoclonal antibody comprises a heavy chain comprising an amino acid sequence that is at least 90% identical to SEQ ID NO: 9, and a light chain comprising an amino acid sequence that is at least 90% identical to SEQ ID NO: 10.

In some embodiments, the monoclonal antibody comprises a heavy chain comprising the amino acid sequence of SEQ ID NO: 9, and a light chain comprising the amino acid sequence of SEQ ID NO: 10.

In some embodiments, the monoclonal antibody specific for PD-L1 is a full-length IgG antibody.

In some embodiments, the full-length IgG antibody is of human IgG1, IgG2, IgG3, IgG4 isotype.

In some embodiments, the monoclonal antibody is of human IgG1 isotype.

In one aspect, the present invention relates to a nucleic acid encoding any of the above antibodies or antigen-binding fragments thereof.

In some embodiments, the nucleic acid is DNA.

In one aspect, the present invention relates to an expression vector comprising any above nucleic acid.

In one aspect, the present invention relates to a method of producing a host cell that is adapted to produce any of the above antibodies or antigen-binding fragments thereof comprising transforming a cell by the above vector.

In one aspect, the present invention relates to a host cell for producing any of the above antibodies or antigen-binding fragments thereof that comprises any of the above nucleic acids.

In one aspect, the present invention relates to a method for producing any of the above antibodies or antigen-binding fragments thereof comprising incubating the above host cell in a culture medium under conditions sufficient to obtain said antibody and optionally followed by isolation and purification of the obtained antibody.

In one aspect, the present invention relates to a pharmaceutical composition for the prevention or treatment of a disease or disorder—mediated by PD-L1 that comprises any of the above antibodies or antigen-binding fragments thereof and one or more pharmaceutically acceptable excipients.

In some embodiments, the pharmaceutical composition is intended for the prevention or treatment of a disease or disorder mediated by PD-L1-selected from the group of: HNSCC, cervical cancer, cancer of unknown primary, glioblastoma, oesophageal cancer, bladder cancer, TNBC, CRC, hepatocellular carcinoma, melanoma, NSCLC, kidney cancer, ovarian carcinoma, Hodgkin's lymphoma, CRC MSI.

In one aspect, the present invention relates to a pharmaceutical combination for the prevention or treatment of a disease or disorder mediated by PD-L1 that comprises any of the above antibodies or antigen-binding fragments thereof and at least one therapeutically active antitumor compound.

In some embodiments, the pharmaceutical combination is intended for the prevention or treatment of a PD-L1-mediated disease or disorder selected from the group of: HNSCC, cervical cancer, cancer of unknown primary, glioblastoma, oesophageal cancer, bladder cancer, TNBC, CRC, hepatocellular carcinoma, melanoma, NSCLC, kidney cancer, ovarian carcinoma, Hodgkin's lymphoma, CRC MSI.

In some embodiments, the pharmaceutical combination comprises a therapeutically active antitumor compound that is selected from a chemotherapeutic agent, an antibody or an anti-hormone agent.

In one aspect, the present invention relates to a method for inhibiting of PD-L1 biological activity in a subject in need thereof that comprises administering to the subject an effective amount of any of the above antibodies or antigen-binding fragments thereof.

In one aspect, the present invention relates to use of any of the above antibodies or antigen-binding fragments thereof or the above pharmaceutical composition for the treatment of a PD-L1-mediated disease or disorder in a subject in need thereof.

In some embodiments, the present invention relates to the use of any of the above antibodies or antigen-binding fragments thereof or the above pharmaceutical composition for the treatment of a PD-L1-mediated disease or disorder selected from the group of: HNSCC, cervical cancer, cancer of unknown primary, glioblastoma, oesophageal cancer, bladder cancer, TNBC, CRC, hepatocellular carcinoma, melanoma, NSCLC, kidney cancer, ovarian carcinoma, Hodgkin's lymphoma, CRC MSI.

DETAILED DESCRIPTION OF THE INVENTION

Definitions and General Methods

Figure 1:
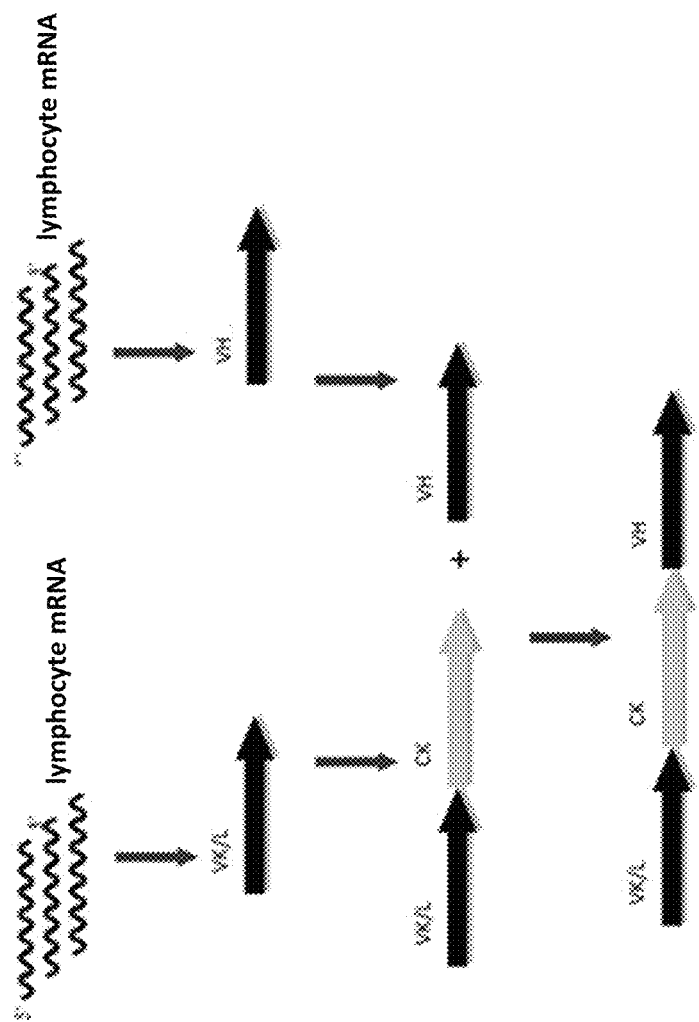
FIG. 1. Scheme for the human combinatorial naive library synthesis.

Unless otherwise defined, all technical and scientific terms used herein will have the same meaning as commonly understood by those of ordinary skill in the art. Although methods and materials similar or equivalent to those described herein can be used in the practice or testing of embodiments of the present invention, exemplary methods and materials are described below. All publications, patent applications, patents, and other references mentioned herein are incorporated by reference in their entirety. In case of conflict, the present specification, including definitions, will control. Although a number of documents are cited herein, this citation is not an admission that any of these documents form part of the common general knowledge in the art.

In addition, unless the context requires otherwise, the terms in the singular include plural terms, and plural terms include singular terms. Typically, used classification and methods of cell and tissue culture, molecular biology, immunology, microbiology, genetics, analytical chemistry, organic synthesis chemistry, medical and pharmaceutical chemistry, as well as the hybridization and chemistry of protein and nucleic acids described herein are well known to those skilled in the art and are widely used in this field. Enzymatic reactions and purification techniques may be performed according to manufacturer's specifications or as commonly accomplished in the art or as described herein.

In this description and embodiments, the words "have" and "contain" or variations thereof, such as "has," "having," "contains," or "containing," are to be understood as including indicated integer or group of integers but without exclusion of any other integer or group of integers.

Antibody-Associated Definitions

PD-L1 (programmed death ligand-1), also known as Cluster Differentiation 274 (CD274) or homologue B7 (B7-H1), is a 40 kDa type 1 transmembrane protein. It consists of 3 domains: extracellular, represented by Ig V and C-like domains (220), transmembrane (21) and intracellular (31). It plays an important role in immune system suppression during pregnancy, transplantation of foreign tissue, some diseases, for example, in hepatitis. Under normal conditions, in response to self-antigens, a certain amount of antigen-specific CD8+ T-effector cells is accumulated in the lymph nodes and spleen, in order to prevent an autoimmune process, PD-1/PD-L1 or B7-1/PD-L1 complexes are formed resulting in inhibitory signalling that reduces the CD8+ T-cell proliferation in lymph nodes. Thus, PD-1/PD-L interaction is one of the key events in the development of immune tolerance.

"Dysfunction" in the context of immune dysfunction, refers to a state of immune reduced responsiveness to antigenic stimulation. The term includes the common elements of both exhaustion and/or anergy, in which antigen recognition may occur, but the ensuing immune response is ineffective to control infection or tumour growth.

"Enhancing T-cell function" means to induce, cause or stimulate a T-cell to have a sustained or amplified biological function, or renew or reactivate exhausted or inactive T-cells. Examples of enhancing T-cell function include: increased secretion of γ-interferon from $CD8^+$ T-cells, increased proliferation, increased antigen responsiveness (e.g., viral or pathogen clearance) relative to such levels before the intervention. In one embodiment, the level of enhancement is at least 50%, alternatively 60%, 70%, 80%, 90%, 100%, 120%, 150%, 200%. The manner of measuring this enhancement is known to those of ordinary skill in the art.

A "T-cell dysfunctional disorder" is a disorder or condition of T-cells characterized by decreased responsiveness to antigenic stimulation. In a particular embodiment, a T-cell dysfunctional disorder is a disorder that is specifically associated with inappropriately increased signalling through PD-1. In another embodiment, T-cell dysfunctional disorder is one in which T-cells are anergic or have decreased ability to secrete cytokines, proliferate, or execute the cytolytic activity. In a specific aspect, the decreased responsiveness results in ineffective control of a pathogen or a tumour expressing an immunogen. Examples of T-cell dysfunctional disorders characterized by T-cell dysfunction include unresolved acute infection, chronic infection and tumour immunity.

"Tumor immunity" refers to the process in which tumours evade immune recognition and clearance. Thus, as a therapeutic concept, tumour immunity is "treatable" when such evasion is attenuated, and the tumours are recognized and attacked by the immune system. Examples of tumour recognition include tumour binding, tumour shrinkage and tumour clearance.

The term "vaccine" as used herein includes any nonpathogenic immunogen that, when inoculated into a host, induces protective immunity against a specific pathogen. Vaccines can take many forms. Vaccines can be whole organisms that share antigens with the pathogen but are not pathogenic themselves (e.g., cowpox). Vaccines can also be prepared from killed (e.g., Salk polio vaccine) or attenuated (lost ability to produce disease—e.g., Sabin polio vaccine). Vaccines can also be prepared from purified macromolecules isolated from the pathogenic organism. For example, toxoid vaccines (e.g., tetanus and diphtheria) containing the inactive form of soluble bacterial toxin and resulting in the production of anti-toxin antibodies, but not immunity to the intact bacteria. Subunit vaccines (e.g., Hepatitis B) contain only a single immunogenic protein isolated from the pathogen of interest. Hapten conjugate vaccines attach certain carbohydrate or polypeptide epitopes isolated from the pathogen of interest to immunogenic carriers, such as tetanus toxoid. These strategies essentially use the epitopes as haptens to induce antibody production, which then recognize the same epitope in the native pathogen. However, to be maximally effective, such vaccines must incorporate both B- and T-cell epitopes, and the T-cell epitopes must be chosen to ensure that they can be recognized, presented and responded to by the immune systems of the host individuals. DNA vaccines exploit the ability of host cells to take up and express DNA encoding pathogenic proteins that is injected intramuscularly. Host responses to immunogens can be enhanced if administered as a mixture with adjuvants. Immune adjuvants function in one or more of the following ways: (1) prolonging retention of the immunogen, (2) increasing effective size of the immunogen (and hence promoting phagocytosis and presentation to macrophages), (3) stimulating the influx of macrophage or other immune cells to the injection site, or (4) promoting local cytokine production and other immunologic activities. Examples of adjuvants include complete Freund's adjuvant (CFA), aluminium salts, and mycobacterial derived proteins, such as muramyl di- or tri-peptides.

Amplification of this gene and/or overexpression of protein thereof have been found in many cancers, including HNSCC, cervical cancer, cancer of unknown primary, glioblastoma, oesophageal cancer, bladder cancer, TNBC, CRC, hepatocellular carcinoma, melanoma, NSCLC, kidney cancer, ovarian carcinoma, Hodgkin's lymphoma, CRC MSI.

The term "binding molecule" includes antibodies and immunoglobulins.

The term "antibody" (Ab) or "immunoglobulin" (lg) as used herein includes whole antibodies and any antigen-binding fragment (i.e., "antigen-binding portion") or individual chains thereof. The term "antibody" refers to a glycoprotein comprising at least two heavy (H) chains and two light (L) chains interconnected by disulfide bonds or antigen-binding portions thereof. Each heavy chain contains a heavy chain variable region (abbreviated herein as VH) and a heavy chain constant region. The heavy chain constant region is comprised of three domains CH1, CH2, and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with the antigen. The constant regions of the antibodies may mediate the immunoglobulin binding to host tissues or factors, including various cells of the immune system (e.g., effector cells) and the first component (Clq) of the classical complement system.

The term "antigen-binding portion" of an antibody (or simply "antibody portion" or "antibody fragment") as used herein refers to one or more fragments of an antibody that retain the ability to specifically bind to an antigen. It has been shown that the antigen-binding function of an antibody can be performed by fragments of a full-length antibody. Examples of binding fragments included within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 341:544-546), which consists of a VH/VHH domain; and (vi) an isolated complementarity determining region (CDR). Furthermore, although the two domains of the Fv fragment, VL and VH, are encoded by separate genes, they can be joined using recombinant methods by a synthetic linker that enables them to be made as a single contiguous chain, in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those skilled in the art, and the fragments are screened in the same manner as are intact antibodies.

Preferably, CDR of the antigen-binding region or the entire antigen-binding portion of the antibodies of the invention is derived from a mouse, llama or donor human library or is substantially of a human origin with certain amino acid residues modified, for example, substituted with different amino acid residues so as to optimize specific antibody properties, e.g., KD, koff, IC50, EC50, ED50. Preferably, the antibody framework regions according to the invention are of a human origin or substantially of a human origin (at least by 80, 85, 90, 95, 96, 97, 98 or 99% of a human origin).

In other embodiments, the antibody antigen-binding region of the invention may be derived from other non-human species, including but not limited to mice, llama, rabbit, rat or hamster. Alternatively, the antigen-binding region may be derived from human species.

The term "variable" refers to the fact that certain segments of the variable domains differ extensively in sequence among antibodies. The V domain mediates antigen binding and defines the specificity of a particular antibody for its particular antigen. However, the variability is not evenly distributed across the 110-amino acid span of the variable domains. Instead, the V regions consist of relatively invariant fragments called framework regions (FRs) of 15-30 amino acids separated by shorter stretches of extreme variability called "hypervariable regions" or CDR or "HVR" or "HV." Each variable domain of native heavy and light chains contains four FRs, mostly receiving the configuration of beta sheets linked by three hypervariable regions, which form loops that bind, and in some cases are part of the beta fold structure. The hypervariable regions in each chain are held together in close proximity by the FRs and with the hypervariable regions from the other chain contribute to the formation of the antigen-binding site of antibodies (see Kabat et al., Sequences of Proteins of Immunological Interest. 5th Ed. Public Health Service, National Institutes of Health, Bethesda, Md. (1991)). The constant domains do not directly participate in antibody binding to the antigen but exhibit different effector functions, such as antibody participation in antibody-dependent cellular cytotoxicity (ADCC).

The term "hypervariable region" ("HVR" or "HV") as used herein refers to the amino acid residues of an antibody that are responsible for antigen binding. Typically, the hypervariable region comprises amino acid residues from the "complementarity determining region" or "CDR" and/or such residues from the "hypervariable loop."

In some cases, it may also be preferable to modify one or more amino acid residues of CDR regions to increase the binding affinity to the target epitope. This is known as "maturation of affinity" and in some cases can be performed in connection with humanization, for example, when humanization of the antibody results in a decrease in binding specificity or affinity, and sufficiently improving the binding specificity or affinity by only inverse mutations is not possible. Various affinity maturation methods are known in the art, for example the in vitro scanning saturation mutagenesis method described by Burks et al., Proc Natl Acad Sci USA, 94:412-417 (1997), and the stepwise in vitro affinity maturation method suggested in Wu et al., Proc Natl Acad Sci USA 95:6037 6042 (1998).

"Framework regions" (FR) are those variable domain residues other than the CDR residues. Each variable domain typically has four FRs identified as FR1, FR2, FR3 and FR4. If the CDRs are defined according to Kabat, the light chain FR residues are localised about at residues 1-23 (LCFR1), 35-49 (LCFR2), 57-88 (LCFR3), and 98-107 (LCFR4) and the heavy chain FR residues are localised about at residues 1-30 (HCFR1), 36-49 (HCFR2), 66-94 (HCFR3), and 103-113 (HCFR4) in the heavy chain. If the CDRs comprise amino acid residues from hypervariable loops, the light chain FR residues are localised about at residues 1-25 (LCFR1), 33-49 (LCFR2), 53-90 (LCFR3), and 97-107 (LCFR4) in the light chain and the heavy chain FR residues are localised about at residues 1-25 (HCFR1), 33-52 (HCFR2), 56-95 (HCFR3), and 102-113 (HCFR4) in the heavy chain residues. In some instances, when the CDR comprises amino acids from both CDR as defined by Kabat and those of a hypervariable loop, the FR residues are adjusted accordingly. For example, when CDRH1 includes amino acids H26-H35, the heavy chain FR1 residues are at positions 1-25 and the FR2 residues are at positions 36-49.

An inventive antibody "binding to" a target antigen is an antibody that binds to the antigen with sufficient affinity such that the antibody can be used as a diagnostic and/or therapeutic agent when targeting a protein or an antigen-expressing cell or tissue and is slightly cross-reactive with other proteins. Based on analytical methods: Fluorescence Activated Cell Sorting (FACS), radioimmunoprecipitation (RIA) or ELISA, in such embodiments, the extent of the binding of an antibody to a non-target protein (to an "off-target protein") is less than 10% of the antibody binding to a particular target protein. With regard to the binding of an antibody to a target molecule, the term "specific binding" or "specifically binds to" or is "specific for" a particular polypeptide or an epitope on a particular polypeptide target means binding that is detectably (measurably) different from a non-specific interaction (e.g., for bH1-44 or bH1-81, a non-specific interaction is binding to bovine serum albumin, casein, fetal bovine serum, or neuravidin). Specific binding can be measured, for example, by determining binding of a molecule compared to binding of a control molecule. For example, specific binding can be determined by competition reaction with another molecule that is similar to the target, for example, an excess of non-labelled target. In this case, specific binding is indicated if the binding of the labelled target to a probe is competitively inhibited by an excess of the non-labelled target. As used herein, the term "specific binding" or phrases "specifically binds to" or is "specific for" a particular polypeptide or an epitope on a particular polypeptide target can be exhibited, for example, by a molecule having a Kd for the target of at least about 200 nM, or at least about 150 nM, or at least about 100 nM, or at least about 60 nM, or at least about 50 nM, or at least about 40 nM, or at least about 30 nM, or at least about 20 nM, or at least about 10 nM, or at least about 8 nM, or at least about 6 nM, or at least about 4 nM, or at least about 2 nM, or at least about 1 nM, or greater. In one embodiment, the term "specific binding" refers to a binding where a molecule binds to a particular polypeptide or epitope on a particular polypeptide without substantially binding to any other polypeptide or polypeptide epitope.

The term "Ka", as used herein, refers to the association rate of a particular antibody-antigen interaction, whereas the term "Kd" refers to the dissociation rate of a particular antibody-antigen interaction.

"Binding affinity" generally refers to the strength of the sum total of noncovalent interactions between a single binding site of a molecule (e.g., an antibody) and its binding partner (e.g., an antigen). Unless indicated otherwise, "binding affinity" refers to intrinsic (inherent, true) binding affinity which reflects a 1:1 interaction between members of a binding pair (e.g., antibody and antigen). The affinity of a molecule X for its partner Y can generally be represented by the dissociation constant (Kd). Desirably the Kd is about 200 nM, 150 nM, 100 nM, 60 nM, 50 nM, 40 nM, 30 nM, 20 nM, 10 nM, 8 nM, 6 nM, 4 nM, 2 nM, 1 nM, or less. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods for measuring the binding affinity are known in the art, any of which can be used for purposes of the present invention.

In one embodiment, the "Kd" or "Kd value" according to the invention is measured by using surface plasmon resonance assays on a BIAcore™-2000 or a BIAcore™-3000 instrument (BIAcore, Inc., Piscataway, N.J.) at 25° C. using immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the manufacturer's instructions. An antigen is diluted with 10 mM sodium acetate, pH 4.8, to 5 μg/ml (~0.2 μM) concentration and then loaded (injected) at a flow rate of 5 μl/minute to achieve approximately 10 response units (RU) of the bound protein. Following the injection of the antigen, 1M ethanolamine solution is injected to block unreacted groups. For kinetics measurements, two-fold serial dilutions of Fab (e.g., 0.78 nM to 500 nM) are injected in PBS with 0.05% Tween (PBST) at 25° C. at a flow rate of approximately 25 μl/min. Association rates (kon) and dissociation rates (koff) are calculated using a simple one-to-one Langmuir binding model (BIAcore Evaluation Software version 3.2) by simultaneous fitting the association and dissociation sensorgram. The equilibrium dissociation constant (Kd) is calculated as the ratio koff/kon. See, e.g., Chen, Y., et al., (1999) J. Mol. Biol. 293: 865-881. If the on-rate exceeds $10^6$ $M^{-1}$ $s^{-1}$ by the surface plasmon resonance assay above, then it can be determined by using a fluorescent quenching technique that measures the increase or decrease in fluorescence emission intensity (excitation=295 nm; emission=340 nm, 16 nm band-pass) at 25° C. of a anti-antigen antibody (Fab form) solution at 20 nM concentration in PBS, pH 7.2, in the presence of increasing antigen concentrations as measured using a spectrometer, such as a stop-flow spectrophometer (Aviv Instruments) or a 8000-series SLM-Aminco spectrophotometer (ThermoSpectronic) with a stir cuvette.

The term "koff" refers to the dissociation rate constant of a particular interaction between a binding molecule and an antigen. The dissociation rate constant koff+ can be measured by biolayer interferometry, for example using an Octetm system.

A "association rate" ("on-rate") or "kon" according to the invention can also be determined with the same surface plasmon resonance technique described above using a BIAcore™-2000 or a BIAcore™-3000 instrument (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the manufacturer's instructions. An antigen is diluted with 10 mM sodium acetate, pH 4.8, to 5 μg/ml (~0.2 μM) concentration and then loaded (injected) at a flow rate of 5 μl/minute to achieve approximately 10 response units (RU) of the bound protein. Following the injection of the antigen, 1M ethanolamine solution is injected to block unreacted groups. For kinetics measurements, two-fold serial dilutions of Fab (e.g., 0.78 nM to 500 nM) are injected in PBS with 0.05% Tween 20 (PBST) at 25° C. at a flow rate of approximately 25 μl/min. Association rates (kon) and dissociation rates (koff) are calculated using a simple one-to-one Langmuir binding model (BIAcore Evaluation Software version 3.2) by simultaneous fitting the association and dissociation sensorgram. The equilibrium dissociation constant (Kd) is calculated as the ratio koff/kon. See, e.g., Chen, Y., et al., (1999) J. Mol. Biol. 293: 865-881. However, if the on-rate exceeds $10^6$ $M^{-1}$ $s^{-1}$ by the surface plasmon resonance assay above, then it can be determined by using a fluorescent quenching technique that measures the increase or decrease in fluorescence emission intensity (excitation=295 nm; emission=340 nm, 16 nm band-pass) at 25° C. of a anti-antigen antibody (Fab form) solution at 20 nM concentration in PBS, pH 7.2, in the presence of increasing antigen concentrations as measured using a spectrometer, such as a stop-flow spectrophometer (Aviv Instruments) or a 8000-series SLM-Aminco spectrophotometer (ThermoSpectronic) with a stir cuvette.

Unless stated otherwise, the phrases "biologically active" and "biological activity" and "biological characteristics" with respect to a polypeptide of the invention means having the ability to bind to a biological molecule.

The phrase "biological molecule" refers to a nucleic acid, a protein, a carbohydrate, a lipid, and a combination thereof. In one embodiment, the biologic molecule exists in nature.

Antibody fragments, such as Fab and F(ab')2 fragments, can be obtained by pepsin or papain hydrolysis of whole antibodies by conventional methods. Moreover, antibodies, antibody portions and immunoadhesion molecules can be obtained using standard recombinant DNA techniques, as described herein.

The term "recombinant antibody" refers to an antibody that is expressed from a cell or cell line comprising the nucleotide sequence(s) that encodes the antibody, wherein said nucleotide sequence(s) are not naturally associated with the cell.

The term "variant" antibody, as used herein, refers to an antibody having an amino acid sequence which differs from the amino acid sequence of its "parent" antibody by adding, removing and/or replacing one or more amino acid residues relative to the parent antibody sequence. In a preferred embodiment, the variant antibody comprises at least one or more (e.g., one to twelve, e.g., two, three, four, five, six, seven, eight or nine, ten, eleven or twelve, and in some embodiments of the invention, from one to about ten) additions, deletions and/or substitutions of amino acids relative to the parent antibody. In some embodiments, the invention additions, deletions and/or substitutions are made at CDR-variant antibody sites. Identity or homology with respect to the variant antibody sequence is defined herein as the percentage of amino acid residues in the variant antibody sequence that are identical with the parent antibody residues, after aligning the sequences and introducing gaps, if necessary, to achieve the maximum percent sequence identity. Variant antibody retains the ability to bind to the same antigen, and preferably an epitope, which binds to the parent antibody, and in some embodiments, at least one property or bioactivity is greater than similar properties of the parent antibody. For example, the variant antibody may be, e.g., a binding affinity expressed, longer half-life, lower IC50 or enhanced ability to inhibit the biological activity of the antigen compared to the parent antibody. Of particular interest herein is the variant antibody showing the biological activity of greater than at least 2 times (preferably at least 5 times, 10 times or 20 times) the biological activity of the parent antibody.

The term "bispecific antibody" means an antibody containing an antigen-binding domain or antigen-binding domains that are capable of specifically binding to two different epitopes on one biological molecule or capable of specifically binding to epitopes on two different biological molecules. A bispecific antibody is also referred to herein as having "dual specificity" or as being an antibody with a "dual specificity."

The term "chimeric antibody" refers broadly to an antibody that contains one or more regions from one antibody and one or more regions from one or more other antibodies, typically an antibody, partly of human origin and partly of non-human origin, i.e. partly obtained from a non-human animal, e.g., mouse, rat, or other rodent or camelid such as llama or alpaca. Chimeric antibodies are preferred over non-human antibodies in order to reduce the risk of an immune response directed against human antibodies, e.g., response directed against murine bodies in a man in the case of the murine antibody. An example of a typical chimeric antibody is one where the variable region sequences are murine, whereas the constant region sequences are human. In the case of the chimeric antibody, non-human portions may be subjected to further change in order to antibody humanisation.

The term "humanisation" refers to the fact that when the antibody is fully or partially of non-human origin, e.g., mouse or llama antibody obtained by immunization of mice or llama, respectively, with an antigen of interest, or is a chimeric antibody based on such mouse or llama antibodies, one can replace some amino acids, in particular in the framework regions and constant domains of the heavy and light chains, in order to avoid or minimize the immune response in humans. The specificity of the interaction between an antibody and target antigen is primarily inherent to the amino acid residues located in six heavy and light chain CDR regions. Therefore, amino acid sequences within CDR regions are much more variable among different antibodies compared to sequences outside the CDR regions. Since the CDR region sequences are responsible for most antibody-antigen interactions, it is possible to express recombinant antibodies that mimic the properties of specific naturally occurring antibody or, more generally, any specific antibody having given amino acid sequence, e.g., by constructing expression vectors that express the CDR region sequences from specific antibody into framework sequences of another antibody. As a result, it is possible to "humanise" a non-human antibody and substantially retain the binding specificity and affinity of the parent antibody. Although it is impossible to accurately predict the immunogenicity and thus an immune response against a human antibody, a specific antibody, non-human antibodies are generally more immunogenic than human antibodies. Chimeric antibodies, in which the foreign (e.g., camel or rodent) constant regions have been replaced by sequences of human origin, showed generally lower immunogenicity than antibodies of completely foreign origin, and there is a tendency to use humanized or fully human antibodies as therapeutic antibodies. Chimeric antibodies or other antibodies of non-human origin, thus, can be humanized to reduce the risk of an immune response directed against the antibody in humans.

For chimeric antibodies, humanization generally involves modification of the framework regions of the variable region sequences. The amino acid residues that are part of the complementarity-determining regions (CDR regions), most likely would not change due to humanization, although in some cases it may be desirable to change the individual amino acid residues in CDR region, for example, to remove the glycosylation site, deamidation site, aspartate isomerization section or undesired cysteine or methionine residue. N-linked glycosylation occurs by oligosaccharide chain addition to the asparagine residue in the tripeptide sequence Asn-X-Ser or Asn-X-Thr, where X can be any amino acid except Pro. Removing N-glycosylation site can be achieved by mutating Asn or Ser/Thr residue for another residue, preferably by conservative substitution. Deamidation of asparagine and glutamine residues can occur depending upon such factors as pH and the surface exposure. Asparagine residues are particularly susceptible to deamidation, particularly if they are present in the Asn-Gly sequence and to a lesser extent in other dipeptide sequences, such as Asn-Ala. With such deamidated region, in particular, Asn-Gly in CDR region sequence, it may be preferable to remove this region, generally by conservative substitution to remove one of the residues involved.

Many methods for humanising an antibody sequence are known in the art; see., e.g., the review by Almagro &

Fransson, Front Biosci. 13:1619-1633 (2008). One of the most commonly used methods is grafting CDR regions, for example, when chimeric antibodies of murine origin involve identification of human germline gene equivalents to murine variable region genes and grafting the sequences of mouse CDR regions into this framework. CDR region grafting may be based on the CDR-region definitions by Kabat, although the later publication (Magdelaine-Beuzelin et al, Crit Rev. Oncol Hematol. 64:210-225 (2007)) suggests that the definition by IMGT® (the International ImMunoGeneTics Information System®, www.imgt.org) may improve the humanization result (see Lefranc et al, Dev. Comp Immunol. 27:55-77 (2003)). In some instances, CDR region grafting can reduce the binding specificity and affinity, and therefore biological activity in non-human CDR-grafted antibody compared to a parent antibody CDR regions derived. Reverse mutations (sometimes referred to as "framework region reparation") can be applied to selected positions in the CDR-grafted antibody, usually in the framework regions, in order to restore binding affinity and specificity of the parent antibody. Determination of possible positions for reverse mutations can be performed using the information available in the literature and in the antibody databases. Amino acid residues that are candidates for reverse mutations are typically exposed on the surface of the antibody molecule, while residues that deepen or have a low degree of surface exposure would usually not changed. An alternative to CDR region grafting and reverse mutation method of humanization is a surface change when unexposed residues of non-human origin are retained, while exposed residues are replaced to human residues.

There are two technologies for obtaining fully human antibodies: using in vitro constructed phage libraries or by in vivo immunization of humanized animals (mice, rats, etc.).

Phage display is the first and most widely used in vitro technology for antibody identification. In 1985, Smith discovered that foreign DNA sequences could be cloned into the filamentous bacteriophage M13 in such a way that the cloned gene sequences are expressed on the surface of the phage particles as fusion proteins (Smith G P: Filamentous fusion phage: novel expression vectors that display cloned antigens on the virion surface. Science 1985, 228:1315-1317). Thus, the fusion proteins of interest may be selected based on their ability to bind other proteins. This discovery was combined with PCR amplification techniques, which allowed cloning the cDNA repertoire of immunoglobulin genes to create a variety of phage libraries containing variable domains that can be used to quickly searching the target-specific monoclonal antibodies. The repertoire of phage libraries reflects the repertoire of B-lymphocyte antibodies of each human or animal whose blood was used to create the library. In 1995, two articles reported about the creation of genetically engineered mice that expressed fully human antibodies, the repertoire of which could be matched with those produced by the hybridoma technology (Lonberg N, Taylor L D, Harding F A, Trounstine M, Higgins K M, Schramm S R, Kuo C C, Mashayekh R, Wymore K, McCabe J G et al.: Antigen-specific human antibodies from mice comprising four distinct genetic modifications. Nature 1994, 368:856-859; Green L L, Hardy M C, Maynard-Currie C E, Tsuda H, Louie D M, Mendez M J, Abderrahim H, Noguchi M, Smith D H, Zeng Y et al.: Antigen-specific human monoclonal antibodies from mice engineered with human Ig heavy and light chain YACs. Nat Genet 1994, 7:13-21.) These animals have disrupted targeted genes of their own endogenous heavy and k light chains of immunoglobulins and introduced transgenes representing segments of human heavy and k light chain genes. The human gene repertoire was found to be used by the mouse immune system to create highly specific and high-affinity antibodies to a greater variety of antigens. Despite the fact that human immunoglobulin transgenic mice express B-cell receptors that are essentially hybrids of mouse and human components (e.g., human immunoglobulin, mouse Igα and Igβ and other signalling molecules), their B-cells develop and mature normally. In some cases, it may also be preferable to modify one or more amino acid residues of CDR regions to increase the binding affinity to the target epitope. This is known as "maturation of affinity" and in some cases can be performed in connection with humanization, for example, when humanization of the antibody results in a decrease in binding specificity or affinity, and sufficiently improving the binding specificity or affinity by only inverse mutations is not possible. Various affinity maturation methods are known in the art, for example the in vitro scanning saturation mutagenesis method described by Burks et al., Proc Natl Acad Sci USA, 94:412-417 (1997), and the stepwise in vitro affinity maturation method suggested in Wu et al., Proc Natl Acad Sci USA 95:6037 6042 (1998).

The term "monoclonal antibody" or "mAb" refers to an antibody synthesized and secreted by an individual clonal population of cells. The clonal population can be a clonal population of immortalized cells. In some embodiments, the immortalized cells in the clonal population are hybrid cells, hybridomas, typically produced by the fusion of individual B-lymphocytes from immunized animals with individual cells from a lymphocytic tumour. Hybridomas are engineered cell type and do not occur in nature.

"Native antibodies" are typically heterotetrameric glycoproteins of about 150,000 daltons composed of two identical light (L) chains and two identical heavy (H) chains. Each light chain is linked to a heavy chain by one covalent disulfide bond, while the number of disulfide linkages between the heavy chains varies among different immunoglobulin isotypes. Each heavy and light chain also has regularly spaced intrachain disulfide bridges. Each heavy chain has at one end a variable domain (VH) followed by a number of constant domains. Each light chain has a variable domain at one and (VL) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains.

The "isolated" ("separated") definition used to describe various antibodies of the disclosure refers to an antibody identified and isolated and/or regenerated from a cell or cell culture where it is expressed. Contaminant components (contaminants) of its natural environment are materials that usually interfere with the diagnostic or therapeutic use of the polypeptide and may include enzymes, hormones, and other proteinaceous or non-proteinaceous species. In preferred embodiments, the antibody is purified (1) to a degree sufficient to obtain at least 15 residues of N-terminal or internal amino acid sequence by use of a spinning cup sequenator (Edman sequenator), or (2) to homogeneity by SDS-PAGE method under reducing or non-reducing conditions using Coomassie blue or, preferably, silver stain. Isolated antibody includes the antibodies in situ within recombinant cells since at least one component of the antibody's natural environment is not be present. Usually, however, the isolated antibody is prepared by at least one purification step.

An "isolated" nucleic acid molecule is a nucleic acid molecule that is identified and separated from at least one contaminant nucleic acid molecule, with which it is ordinarily associated in the natural source of the antibody nucleic acid. An isolated nucleic acid molecule is distinguished from the form or setting in which it is found in nature. Isolated nucleic acid molecules, therefore, are distinguished from the nucleic acid molecules as they exist in natural cells. However, an isolated nucleic acid molecule includes nucleic acid molecules contained in cells that ordinarily express the antibody where, for example, the nucleic acid molecule is in a chromosomal location different from that of natural cells.

The term "epitope" as used herein refers to a portion (determinant) of an antigen that specifically binds to a binding molecule (e.g., an antibody or a related molecule, such as a bispecific binding molecule). Epitopic determinants usually consist of chemically active surface groupings of molecules such as amino acids or sugar side chains and usually have specific three-dimensional structural characteristics, as well as specific charge characteristics. An epitope can be "linear" or "conformational." In a linear epitope, all the points of interaction between the protein (e.g., an antigen) and the interacting molecule (such as an antibody) occur linearly along the primary amino acid sequence of the protein. In a conformational epitope, the points of interaction occur across amino acid residues on the protein that are separated from one another in the primary amino acid sequence. Once the desired antigen epitope is identified, antibodies to this epitope can be generated using techniques well known in the art. In addition, the generation and characterization of the antibodies or other binding molecules may shed light on the information about desirable epitopes. Based on this information, binding molecules can then be competitively screened for binding to the same or similar epitopes, e.g. by competition studies to find binding molecules that compete for binding to the antigen.

The term "peptide linker" herein means any peptide having the ability to link domains with lengths depending on the domains that it binds to each other containing any amino acid sequence. Preferably, the peptide linker has a length of more than 5 amino acids and consists of any set of amino acids selected from G, A, S, P, E, T, D, K.

The term "effector function" of an antibody refers to the biological activities associated with the Fc region (Fc region native sequence or variant Fc region amino acid sequence) of the antibody and varies depending on the antibody isotype. Examples of antibody effector functions are $Cl_q$-binding; complement dependent cytotoxicity; Fc receptor binding; antibody-dependent cellular cytotoxicity (ADCC); phagocytosis; downregulation of cell surface receptors (e.g. B-cell receptor, BCR) and B-cell activation.

"Antibody-dependent cell-mediated cytotoxicity of cells" and "ADCC" refer to a cell-mediated response wherein non-specific cytotoxic cells that express Fc receptors (FcR) (e.g. natural killer (NK) cells, neutrophils, cells, and macrophages) recognize bound antibody on a target cell and subsequently induce target cell lysis. The primary cells for mediating ADCC, NK cells, express only FcγRIII, whereas monocytes express FcγRI, FcγRII and FcγRIII. FcR expression on hematopoietic cells is summarized in Table 3 on page 464 in Ravetch and Kinet, Annu. Rev. Immunol 9: 457-92 (1991). To assess ADCC activity of a molecule of interest, in vitro ADCC assays can be performed, such as described in U.S. Pat. No. 5,500,362 or 5,821,337. Effector cells useful for such assays include peripheral blood mononuclear cells (PBMC) and Natural Killer (NK) cells. Alternatively or additionally, ADCC activity of the molecule of interest can be assessed in vivo, for example in an animal model such as that disclosed in Clynes et al. PNAS (USA) 95: 652-656 (1998).

"Human effector cells" are leukocytes, which express one or more FcRs and perform effector functions. Preferably, the cells express at least FcγRIII and perform ADCC effector function. Examples of human leukocytes that mediate ADCC include peripheral blood mononuclear cells (PBMC), natural killer (NK) cells, monocytes, cytotoxic T-cells and neutrophils; PBMC and NK cells being preferred. Effector cells can be isolated from their natural source, for example from blood or PBMC, as described herein.

The terms "Fc receptor" or "FcR" are used to describe a receptor that binds the Fc region of an antibody. The preferred FcR is a native sequence human FcR. Moreover, a preferred FcR is FcR (receptor gamma) which binds an IgG antibody, the preferred receptors including FcγRI, FcγRII, and FcγRIII subclasses of receptors, including allelic variants and alternatively spliced forms of these receptors. FcγRII receptors include FcγRIIA ("activating receptor") and FcγRIIB ("inhibiting receptor"), which have similar amino acid sequences that differ primarily in the cytoplasmic domains. Activating receptor FcγRIIA contains the immunoreceptor tyrosine-based activation motif (ITAM) in its cytoplasmic domain. Inhibiting receptor FcγRIIB contains the immunoreceptor tyrosine-based inhibition motif (ITIM) in its cytoplasmic domain (see Daëron, Annu. Rev. Immunol. 15: 203-234 (1997)). A review of FcR is provided in Ravetch and Kinet, Annu. Rev. Immunol 9: 457-92 (1991); Capel et al., Immunomethods 4: 25-34 (1994); and de Haas et al., J. Lab. Clin. Med. 126: 330-41 (1995). Other FcR, including FcR, which will be identified in the future, are included herein within the term "FcR." The term also includes the neonatal receptor, FcRn, which is responsible for the transfer of maternal IgG to the fetus (Guyer et al., J. Immunol. 117: 587 (1976), and Kim et al., J. Immunol. 24: 249 (1994)).

"Complement dependent cytotoxicity" or "CDC" refers to the ability of molecule in the presence of a complement to lyse a target. Complement activation pathway is initiated by the binding of the first component of the complement system (C1q) with a molecule (e.g. an antibody) in complex with its antigen. To assess complement activation, a CDC assay can be performed, e.g. as described in Gazzano-Santoro et al., J. Immunol. Methods 202: 163 (1996).

The term "identity" or "homology" should be interpreted to mean, if necessary to achieve the maximum percent identity of the whole sequence, and does not replace any part of the sequence identity to the conserved considered, in aligning the sequences and after the introduction of "gaps", the percentage of residues in the candidate sequence with the corresponding sequence compared to the same amino acid residues. Either N- or C-terminal extensions and insertions should not be construed as reducing identity or homology. Methods and computer programs for the alignment are well known. Sequence identity may be measured using sequence analysis software (for example, Sequence Analysis Software Package, Genetics Computer Group, University of Wisconsin Biotechnology Center, 1710 University Ave., Madison, Wis. 53705). This software is useful for such sequences by determining the degree of homology for a variety of substitutions, deletions (eliminations), and other modifications.

The term "homologous" with respect to an antibody polypeptide sequence should be construed as an antibody exhibiting at least 70%, preferably 80% sequence, more preferably 90% and most preferably 95% sequence identity to a polypeptide sequence. The term in relation to a nucleic acid sequence should be construed as a nucleotide sequence exhibiting at least 85%, preferably 90%, more preferably 95% and most preferably 97% sequence identity relative to a nucleic acid sequence.

A modification(s) in the amino acid sequences of the antibodies described herein is provided. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions, and/or insertions into and/or substitutions of, residues within the amino acid sequences of the antibody. Any combination of deletion, insertion, and substitution is made to arrive at the final construct, provided that the final construct possesses the desired characteristics. The amino acid alterations may also alter post-translational processes in the antibody, such as changes in the number or positions of glycosylation sites.

A variant for modifying amino acid sequences of antibodies by amino acid substitutions. Such variant is a substitution of at least one amino acid residue in the antibody molecule with another residue. Sites of interest for substitutional mutagenesis include hypervariable regions or CDRs, but substitutions are also contemplated in the FR or Fc region. Conservative substitutions are shown in Table 1 under the heading of "preferred substitutions." If such substitutions result in a change in biological activity, then more substantial changes, denominated exemplary substitutions in Table A or as further described below in reference to amino acid classes, can be introduced and the products can be screened.

TABLE A

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

The terms "nucleic acid," "nucleic sequence," "nucleic acid sequence," "polynucleotide," "oligonucleotide," "polynucleotide sequence," and "nucleotide sequence," which are used interchangeably herein, denote an exact sequence of nucleotides modified or unmodified determining a nucleic acid fragment or region containing or not non-natural nucleotides and being either a double-stranded DNA or RNA or single-chain DNA or RNA or transcription products of said DNAs.

It must be understood that the present invention does not relate to the nucleotide sequences in their natural chromosomal environment, i.e. in the natural state. The sequences of the invention have been isolated and/or purified, i.e. they have been collected, directly or indirectly, for example by copying, their environment has been at least partially modified. Thus, isolated nucleic acids obtained by genetic recombination, for example, by receiving cells (host cells), or obtained by chemical synthesis are also to be contemplated herein.

A reference to the nucleotide sequence encompasses its complement unless otherwise specified. Thus, a reference to a nucleic acid having a specific sequence should be understood as encompassing its complementary strand having its complementary sequence.

The expression "control sequences" refers to DNA sequences necessary for the expression of an operably linked coding sequence in a particular host organism. The control sequences that are suitable for prokaryotes, for example, include a promoter, optionally an operator, and a ribosome binding site. Eukaryotic cells are known to utilize promoters, polyadenylation signals, and enhancers.

The nucleic acid is "operably linked" when it is placed into a functional relationship with another nucleic acid sequence. For example, a pre-sequence or secretory leader DNA sequence is operably linked to a polypeptide DNA when it is expressed as a preprotein that participates in the polypeptide secretion; a promoter or enhancer is operably linked to a coding sequence when it impacts on the sequence transcription; or a ribosome binding site is operably linked to a coding sequence when it is positioned so as to facilitate translation. Generally, "operably linked" means that linked DNA sequences are contiguous and, as for a secretory leader, are contiguous and in reading phase. However, enhancers do not have to be contiguous. Linking is accomplished by ligation at existing restriction sites. If such sites do not exist, the synthetic oligonucleotide adaptors or linkers are used in accordance with conventional practice.

The term "vector" as used herein means a nucleic acid molecule capable of transporting another nucleic acid to which it is linked. In some embodiments of the invention, the vector is a plasmid, i.e., a circular double-stranded piece of DNA into which additional DNA segments may be ligated. In some embodiments of the invention, the vector is a viral vector, wherein additional DNA segments may be ligated into the viral genome. In some embodiments of the invention, the vectors are capable of autonomous replication in a host cell into which they are introduced (e.g., bacterial vectors having a bacterial origin of replication and episomal mammalian vectors). In other embodiments of the invention, the vectors (e.g., non-episomal mammalian vectors) can be integrated into the host cell genome when introduced into a host cell and thereby are replicated along with the host gene. Moreover, certain vectors are capable of directing the expression of genes to which they are operably linked. Such vectors are referred to herein as "recombinant expression vectors" (or simply "expression vectors").

The term "recombinant host cell" (or simply "host cell") as used herein is intended to refer to a cell into which a recombinant expression vector has been introduced. The present invention relates to host cells, which may include, e.g., a vector according to the present invention described above. The present invention also relates to host cells that comprise, for example, a nucleotide sequence encoding a heavy chain or antigen-binding portions thereof, a nucleotide sequence encoding a light chain or antigen-binding portions thereof or both of the first binding domain and/or second binding domain in a trispecific binding molecule of the invention. It should be understood that "recombinant host cell" and "host cell" are intended to refer not only to the particular subject cell but to the progeny of such a cell. Since modifications may be held in succeeding generations due to either mutation or environmental influences, such progeny may not, in fact, be identical to the parent cell, but such cells are still included within the scope of the term "host cell" as used herein.

The term "excipient" is used herein to describe any ingredient other than the compound(s) of the invention.

A "pharmaceutical composition" means a composition comprising an antibody of the invention and at least one of components selected from the group consisting of pharmaceutically acceptable and pharmacologically compatible vehicles, solvents, diluents, carriers, auxiliary, dispensing and receptive agents, delivery agents, such as preservatives, stabilizers, fillers, dispersing agents, humectants, emulsifiers, suspending agents, thickeners, sweeteners, fragrances, flavorings, antibacterial agents, fungicides, lubricants, and prolonged delivery adjusters, the choice and suitable proportions of which depend on the nature and the method of administration and dosage. Exemplary suspending agents are ethoxylated isostearyl alcohol, polyoxyethylene, sorbitol and sorbitan ester, microcrystalline cellulose, aluminium metahydroxide, bentonite, agar and tragacanth, as well as mixtures thereof. Protection against microorganism action can be provided by various antibacterial and antifungal agents, such as parabens, chlorobutanol, sorbic acid, and similar compounds. The composition may also include isotonic agents, for example, sugars, sodium chloride and the like. Prolonged action of the composition can be provided by the use of agent delaying absorption, for example, aluminium monostearate and gelatin. Examples of suitable carriers, solvents, diluents, or delivery agents are water, ethanol, polyalcohols and mixtures thereof, vegetable oils (such as olive oil) and injectable organic esters (such as ethyl oleate). Exemplary fillers are lactose, milk sugar, sodium citrate, calcium carbonate, calcium phosphate and the like. Examples of dispersing and dispensing agents are starch, alginic acid and its salts, silicates. Examples of lubricants are magnesium stearate, sodium lauryl sulfate, talc, and polyethylene glycol of high molecular weight. A pharmaceutical composition for oral, sublingual, transdermal, intramuscular, intravenous, subcutaneous, topical or rectal administration of the agent, alone or in combination with another agent, can be administered to animals and humans in a standard form of administration as a mixture with conventional pharmaceutical carriers. Suitable standard forms of administration include oral forms such as tablets, gelatin capsules, pills, powders, granules, chewing gums and oral solutions or suspensions, sublingual and buccal forms of administration, aerosols, implants, local, transdermal, subcutaneous, intramuscular, intravenous, intranasal or intraocular forms of administration and rectal forms of administration.

"Drug (medication)" means a substance (or a mixture of substances in the form of a pharmaceutical composition) in the form of tablets, capsules, injections, ointments and other ready-to-use forms intended to restore, correct or modify physiological functions in humans and animals, and also for treatment and prevention of diseases, diagnostics, anesthesia, contraception, cosmetology and others.

The term "PD-L1 mediated disease or disorder" contemplate all diseases or disorders that are either directly or indirectly related to PD-L1, including the aetiology, development, progress, persistence or pathology of the disease or disorder.

"Treat," "treatment" and "therapy" refer to a method of attenuating or eliminating a biological disorder and/or at least one of its associated symptoms. As used herein, to "relieve" a disease, disorder or condition means reducing the severity and/or incidence of the disease, disorder or condition symptoms. In addition, the references herein to "treatment" include references to curative, palliative and preventive therapy.

In one aspect, the subject of the treatment or the patient is a mammal, preferably a human subject. The above subject may be male or female of any age.

The term "disorder" means any condition that can be improved by the treatment of the present invention. The definition of this term includes chronic and acute disorders or diseases, including pathological conditions that cause the predisposition of the mammal to the disorder manifestation. Non-limiting examples of diseases to be treated include benign and malignant tumors; leukemias and lymphoid malignancies, in particular breast, ovarian, stomach, endometrial, salivary gland, lung, kidney, colon, thyroid, pancreas, prostate or bladder cancer; neural, glial, astrocytic, hypothalamus and other glandular, macrophage, epithelial, stromal and blastocoelic disorders; inflammatory, angiogenic and immunological disorders. A preferred disorder to be treated according to the invention is cancer.

The terms "cancer" and "cancerous" refer to or describe the physiological condition in mammals that is typically characterized by unregulated cell growth/proliferation. Included in this definition are benign and malignant cancers. Examples of cancer include but are not limited to carcinoma, lymphoma, blastoma, sarcoma, and leukaemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastric or stomach cancer including gastrointestinal cancer, pancreatic cancer, glioblastoma, glioma, cervical cancer, ovarian cancer, liver cancer, bladder cancer, breast cancer, colon cancer, colorectal cancer, endometrial or uterine carcinoma, salivary gland carcinoma, kidney cancer (e.g., renal cell carcinoma), prostate cancer, vulval cancer, thyroid cancer, hepatic carcinoma, anal carcinoma, penile carcinoma, melanoma, and various types of head and neck cancer.

The terms "immune response," "autoimmune reaction," and "autoimmune inflammation" refer, for example, to the action of lymphocytes, antigen presenting cells, phagocytic cells, granulocytes, and soluble macromolecules produced by these cells or liver cells (including antibodies, cytokines, and complement, resulting from selective damage to, destruction of, or elimination from the human body invasive pathogens, cells or tissues infected with pathogens, cancerous cells, or, in cases of autoimmunity or pathological inflammation, normal human cells or tissues).

"Therapeutically effective amount" is considered to be an amount of the therapeutic agent administered during treatment that will relieve to some extent one or more symptoms of the disease being treated.

The term "chronic" application refers to the continuous (prolonged) use of an agent(s) as opposed to the acute (short-term) administration, so as to maintain the initial therapeutic effect (activity) for a long period of time.

"Intermittent" use refers to a treatment that is not carried out consistently without interruptions but rather is periodic in its nature.

In the present description and in the following claims, unless the context otherwise requires, the words "have," "contain" and "comprise" or variations thereof such as "has," "having," "contains," "containing," "comprises" or "comprising" are to be understood as the inclusion of a stated integer or group of integers but not the exclusion any other integer or group of integers.

DETAILED DESCRIPTION OF THE INVENTION

Antibody

The present invention relates to an antibody or antigen-binding fragment that binds to PD-L1 (programmed death ligand 1 protein).

In one embodiment, the present invention relates to an isolated antibody or antigen-binding fragment thereof that binds to PD-L1 and comprises:

(a) a heavy chain variable region comprising CDR3 with an amino acid sequence having at least 90%, 91%, 92%, 93%, 94%, 95%, 96%, 97%, 98% or 99% homology or identity to the sequence of APLLLAMTFGVGS (SEQ ID NO: 3), and (b) a light chain variable region comprising a CDR3 with an amino acid sequence having at least 90%, 91%, 92%, 93%, 94%, 95%, 96%, 97%, 98% or 99% homology or identity to the sequence of ALYMGNGGHM (SEQ ID NO: 7).

In one embodiment, the present invention relates to an isolated antibody or antigen-binding fragment thereof that binds to PD-L1 and comprises:

(a) a heavy chain variable region comprising CDR3 with the amino acid sequence of APLLLAMTFGVGS (SEQ ID NO: 3), and (b) a light chain variable region comprising CDR3 with the amino acid sequence of ALYMGNGGHM (SEQ ID NO:7).

In one embodiment, the present invention relates to an isolated antibody or antigen binding fragment thereof that binds to PD-L1 and comprises:

(a) a heavy chain variable region comprising:

(i) CDR1 with an amino acid sequence having at least 90%, 91%, 92%, 93%, 94%, 95%, 96%, 97%, 98% or 99% homology or identity to the sequence of DYAMS (SEQ ID NO: 1), (ii) CDR2 with an amino acid sequence having at least 90%, 91%, 92%, 93%, 94%, 95%, 96%, 97%, 98% or 99% homology or identity to the sequence of DISWSGSNTNYADSVKG (SEQ ID NO: 2), (iii) CDR3 with an amino acid sequence having at least 90%, 91%, 92%, 93%, 94%, 95%, 96%, 97%, 98% or 99% homology or identity to the sequence of APLLLAMTFGVGS (SEQ ID NO: 3), and (b) a light chain variable region comprising:

(i) CDR1 with an amino acid sequence having at least 90%, 91%, 92%, 93%, 94%, 95%, 96%, 97%, 98% or 99% homology or identity to the sequence of GLSSGTVTAINYPG (SEQ ID NO: 5), (ii) CDR2 with an amino acid sequence having at least 90%, 91%, 92%, 93%, 94%, 95%, 96%, 97%, 98% or 99% homology or identity to the sequence of NTNTRHS (SEQ ID NO: 6), (iii) CDR3 with an amino acid sequence having at least 90%, 91%, 92%, 93%, 94%, 95%, 96%, 97%, 98% or 99% homology or identity to the sequence of ALYMGNGGHM (SEQ ID NO:7).

In one embodiment, the present invention relates to an isolated antibody or antigen-binding fragment thereof that binds to PD-L1 and comprises:

(a) a heavy chain variable region comprising:

(i) CDR1 with the amino acid sequence of DYAMS (SEQ ID NO: 1), (ii) CDR2 with the amino acid sequence of DISWSGSNTNYADSVKG (SEQ ID NO: 2), (iii) CDR3 with the amino acid sequence of APLLLAMTFGVGS (SEQ ID NO: 3), and (b) a light chain variable region comprising:

(i) CDR1 with the amino acid sequence of GLSSGTVTAINYPG (SEQ ID NO: 5), (ii) CDR2 with the amino acid sequence of NTNTRHS (SEQ ID NO: 6), (iii) CDR3 with the amino acid sequence of ALYMGNGGHM (SEQ ID NO:7).

In one embodiment, the present invention relates to an isolated antibody or antigen binding fragment thereof that binds to PD-L1 and comprises:

(a) a heavy chain variable region with an amino acid sequence having at least 90%, 91%, 92%, 93%, 94%, 95%, 96%, 97%, 98% or 99% homology or identity to the sequence of EVQLVESGGGVVRPGGSLRLSCAASGFTFDDYAMSWVRQAPGKGLEWVSDISWSGSNTNYADSV KGRFTISRDNAKNSLYLQMNSLRAEDTALYHCARAPLLLAMTFGVGSWGQGTLVTVSS (SEQ ID NO: 4), and (b) a light chain variable region with an amino acid sequence having at least 90%, 91%, 92%, 93%, 94%, 95%, 96%, 97%, 98% or 99% homology or identity to the sequence of QTVVTQEPSLSVSPGGTVT LTCGLSSGTVTAINYPGWYQQTPGQAPRTLIYNTNTRHSGVPDRF SGSISGNKAALTITGAQAEDEADYYCALYMGNGGHMFGGGTK (SEQ ID NO: 8).

In one embodiment, the present invention relates to an isolated antibody or antigen-binding fragment thereof that binds to PD-L1 and comprises:

(a) a heavy chain variable region with the amino acid sequence of EVQLVESGGGVVRPGGSLRLSCAASGFTFDDYAMSWVRQAPGKGLEWVSDISWSGSNTNYADSV KGRFTISRDNAKNSLYLQMNSLRAEDTALYHCARAPLLLAMTFGVGSWGQGTLVTVSS (SEQ ID NO: 4), and (b) a light chain variable region with the amino acid sequence of QTVVTQEPSLSVSPGGTVTLTCGLSSGTVT AINYPGWYQQTPGQAPRTLIYNTNTRHSGVPDRF SGSISGNKAALTITGAQAEDEADYYCALYMGNGGHMFGGGTK (SEQ ID NO: 8).

In one embodiment, the present invention relates to an isolated antibody that binds to PD-L1 and comprises:

(a) a heavy chain with an amino acid sequence having at least 90%, 91%, 92%, 93%, 94%, 95%, 96%, 97%, 98% or 99% homology or identity to the sequence of EVQLVESGGGVVRPGGSLRLSCAASGFTFDDYAMSWVRQAPGKGLEWVSDISWSGSNTNYADSV KGRFTISRDNAKNSLYLQMNSLRAEDTALYHCARAPLLLAMTFGVGSWGQGTLVTVSSASTKGP SVFPLAPSSKSTSGGTAALGCLVKDYFPEPVTVSWNSGALTSGVHTFPAVLQSSGLYSLSSVVT VPSSSLGTQTYICNVNHKPSNTKVDKRVEPKSCDKTHTCPPCPAPEAAGGPSVFLFPPKPKDTL MISRTPEVTCVVVDVSHEDPEVKFNWYVDGVEVHNAKTKPREEQYNSTYRVVSVLTVLHQDWLN GKEYKCKVSNKALPAPIEKTISKAKGQPREPQVYTLPPSRDELTKNQVSLTC LVKGFYPSDIAV EWESNGQPENNYKTTPPVLDSDGSFFLYSKLTVDKSRWQQGNVFSCSVMHEALHNHYTQKSLSLSPGK (SEQ ID NO: 9), and (b) a light chain with an amino acid sequence having at least 90%, 91%, 92%, 93%, 94%, 95%, 96%, 97%, 98% or 99% homology or identity to the sequence of QTVVTQEPSLSVSPGGTVTLTCGLSSGTVTAINYPGWYQQTPGQAPRTLIYNTNTRHSGVPDRF SGSISGNKAALTITGAQAEDEADYYCALYMGNGGHMFGGGTKLTVLGQPKAAPSVTLFPPSSEE LQANKATLVCLISDFYPGAVTVAWKADSSPVKAGVETTTPSKQSNNKYAASSYLSLTPEQWKSH RSYSCQVTHEGSTVEKTVAPTECS (SEQ ID NO: 10).

In one embodiment, the present invention provides an isolated antibody that binds to PD-L1 and comprises:

(a) a heavy chain with an amino acid sequence of EVQLVESGGGVVRPGGSLRLSCAASGFTFDDYAMSWVRQAPGKGLEWVSDISWSGSNTNYADSVKGRFTISRDNAKNSLYLQMNSLRAEDTALYHCARAPLLLAMTFGVGSWGQGTLVTVSSASTKGP SVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEAAGGPSVFLFPPKPKDTL MISRTPEVTCVVVDVSHEDPEVKFNWYVDGVEVHNAKTKPREEQYNSTYRVVSVLTVLHQDWLN GKEYKCKVSNKALPAPIEKTISKAKGQPREPQVYTLPPSRDELTKNQVSLTCL VKGFYPSDIAV EWESNGQPENNYKTTPPVLDSDGSFFLYSKLTVDKSRWQQGNVFSCSVMHEALHNHYTQKSLSLSPGK (SEQ ID NO: 9), and (b) a light chain with an amino acid sequence of QTVVTQEPSLSVSPGGTVTLTCGLSSGTVTAINYPGWYQQTPGQAPRTLIYNTNTRHSGVPDRF SGSISGNKAALTITGAQAEDEADYYCALYMGNGGHMFGGGTKLTVLGQPKAAPSVTLFPPSSEE LQANKATLVCLISDFYPGAVTVAWKADSSPVKAGVETTTPSKQSNNKYAASSYLSLTPEQWKSH RSYSCQVTHEGSTVEKTVAPTECS (SEQ ID NO: 10).

In one embodiment of the present invention, the isolated antibody that binds to PD-L1 is a monoclonal antibody.

In one embodiment of the present invention, the monoclonal antibody that binds to PD-L1 is a full-length IgG antibody.

In one embodiment of the invention, the full-length IgG antibody is of human IgG1, IgG2, IgG3, IgG4 isotype.

In one embodiment of the invention, the full-length IgG antibody is of human IgG1 isotype.

In one embodiment of the present invention, the isolated antibody is a BCD-135 antibody that binds PD-L1 and contains a heavy chain variable region comprising CDR3 with the amino acid sequence of SEQ ID NO: 3, a light chain variable region comprising CDR3 with the amino acid sequence of SEQ ID NO:7.

In one embodiment of the present invention, the isolated antibody is a BCD-135 antibody that binds PD-L1 and contains a heavy chain variable region comprising CDR1-3 with the corresponding amino acid sequences of SEQ ID NO: 1-3 and a light chain variable region comprising CDR1-3 with the corresponding amino acid sequences of SEQ ID NO: 5-7.

In one embodiment of the present invention, the isolated antibody is a BCD-135 antibody that binds to PD-L1 and contains a heavy chain variable region with the amino acid sequence of SEQ ID NO: 4 and a light chain variable region with the amino acid sequence of SEQ ID NO: 8.

In one embodiment of the present invention, the isolated antibody is a BCD-135 antibody that binds to PD-L1 and contains a heavy chain with the amino acid sequence of SEQ ID NO: 9 and a light chain with an amino acid sequence of SEQ ID NO: 10.

Nucleic Acid Molecules

The present invention also relates to nucleic acid molecules and sequences encoding an anti-PD-L1 antibody of the invention described herein. In some embodiments, first domain and second domain amino acid sequences of the anti-PD-L1 antibody are encoded by the various nucleic acid molecules. Where the first domain and/or the second domain comprises a heavy chain and a light chain, in some embodiments, the heavy chain and light chain amino acid sequences are encoded by various nucleic acids. In other embodiments, the heavy chain and light chain amino acid sequences are encoded by the same nucleic acid molecule. In certain embodiments, the nucleic acid molecule can encode any combination of amino acid sequences (e.g., heavy and light chain sequences) of the first and the second domains. In a particular embodiment, the nucleic acid molecule can encode the amino acid sequence of the first binding domain and the light chain amino acid sequence of the second binding domain, optionally including any sequence of the peptide linker linking thereof. A reference to the nucleotide sequence encompasses its complement unless otherwise specified. Thus, a reference to a nucleic acid having a specific sequence should be understood as encompassing its complementary strand having its complementary sequence. The term "polynucleotide" as referred to herein means a polymeric form of nucleotides at least 10 bases in length, either ribonucleotides or deoxynucleotides or a modified form of either type of nucleotide. The term includes the single and double-stranded form.

The present invention also relates to nucleotide sequences that are at least 75%, 80%, 85%, 90%, 95%, 97%, 98% or 99% identical to one or more of the above nucleotide sequences encoding an amino acid sequence selected from the group consisting of SEQ ID NO: 1-3, 5-7. In certain embodiments, nucleotide sequences is at least 90%, 91%, 92%, 93%, 94%, 95%, 96%, 97%, 98% or 99% identical to a nucleotide sequence encoding an amino acid sequence selected from the group consisting of SEQ ID NO: 4 or 8. The present invention also relates to nucleotide sequences that are at least 80%, 85%, 90%, 95%, 97%, 98% or 99% identical to one or more of the above nucleotide sequences encoding an amino acid sequence selected from the group consisting of SEQ ID NO: 9-10.

In one aspect, the present invention relates to a nucleic acid molecule comprising a nucleotide sequence that encodes an amino acid sequence selected from SEQ ID NO: 1-10. The nucleic acid molecule can also comprise any combination of these nucleotide sequences. In one embodiment, the nucleic acid molecule comprises a nucleotide sequence encoding the amino acid of SEQ ID NO: 3 and the nucleotide sequence encoding the amino acid sequence of SEQ ID NO: 7. In another embodiment, the nucleic acid molecule comprising nucleotide sequences encoding the amino acid of SEQ ID NO: 1-3 and nucleotide sequences encoding the amino acid sequence of SEQ ID NO: 5-7. In one embodiment, the nucleic acid molecule comprises a nucleotide sequence encoding the amino acid of SEQ ID NO: 4 and the nucleotide sequence encoding the amino acid sequence of SEQ ID NO: 8. In one embodiment, the nucleic acid molecule comprises a nucleotide sequence encoding the amino acid of SEQ ID NO: 9 and the nucleotide sequence encoding the amino acid sequence of SEQ ID NO: 10.

In any of the above embodiments, the nucleic acid molecules can be isolated.

The nucleic acid molecule of the present invention can be isolated from any source that produces an anti-PD-L1 antibody or a portion thereof. In certain embodiments, the nucleic acid molecule of the invention can be synthesized but not isolated.

In some embodiments, the nucleic acid molecule of the invention can comprise a nucleotide sequence encoding a VH domain of the first or second domain from the anti-PD-L1 antibody of the invention coupled in-frame to a nucleotide sequence encoding a heavy chain constant domain from any source. Similarly, the nucleic acid molecule of the invention can comprise a nucleotide sequence encoding a VL domain of the first or second region from the anti-PD-L1 antibody of the invention, combined in frame with the nucleotide sequence encoding a light chain constant domain from any source.

In another aspect of the present invention, the nucleic acid molecules encoding the variable domain of the heavy (VH) and light (VL) chains of the first or second binding domain may be "converted" to full-length antibody genes. In one embodiment, the nucleic acid molecules encoding the VH or VL domains are converted into full-length antibody genes by inserting into an expression vector already encoding heavy chain constant (CH) or light chain constant (CL) domains, respectively, such that the VH segment is operatively linked to the CH segment(s) within the vector and/or the VL segment is operatively linked to the CL segment within the vector. In another embodiment, nucleic acid molecules encoding the VH and/or VL domains are converted into full-length antibody genes by linking, e.g., ligating, a nucleic acid molecule encoding a VH and/or VL domain to a nucleic acid molecule encoding a CH and/or CL domain using standard molecular biological techniques. Nucleic acid molecules encoding the full-length heavy and/or light chains may then be expressed from a cell into which they have been introduced.

Nucleic acid molecules can be used to express a large quantity of recombinant anti-PD-L1 antibodies. The nucleic acid molecules can be used to produce human antibodies, humanized antibodies, chimeric antibodies, bispecific antibodies, single-chain antibodies, immunoadhesins, diabodies, mutated antibodies and antibody derivatives, as described herein.

Vector

In yet another aspect, the present invention relates to a vector suitable for the expression of any of the nucleotide sequences described herein.

The present invention relates to vectors containing the nucleic acid molecules encoding any of the amino acid sequences of anti-PD-L1 antibodies or portions thereof (e.g., first binding domain heavy chain and/or second binding domain heavy and/or light chain sequences) as described herein. The present invention further relates to vectors comprising nucleic acid molecules encoding fusion proteins, modified antibodies, antibody fragments.

In another embodiment of the invention, the nucleic acid molecules and vectors can be used to produce mutated anti-PD-L1 antibodies. The antibodies can be mutated within variable domains of the first and/or second binding domain heavy and/or light chains, for example, to alter the binding affinity of the anti-PD-L1 antibodies. For example, a mutation may occur in one or more CDR regions to increase or decrease $K_D$ of anti-PD-L1 antibodies, to increase or decrease $k_{off}$ or modify the antibody binding specificity to PD-L1. In another embodiment, subjected to one or more mutations is an amino acid residue that is known to be altered compared to the germline in the antibody corresponding to the first or second binding domain of an anti-PD-L1 antibody of the invention. These mutations can be made in CDR region or framework region within a variable domain or constant domain. In a preferred embodiment of the invention, the mutations are produced within the variable domain. In another embodiment of the invention, subjected to one or more mutations is an amino acid residue that is known to be altered compared to the germline in CDR or framework region of the variable domain in the anti-PD-L1 antibody of the invention.

In some embodiments, the anti-PD-L1 antibodies of the invention are expressed by inserting a DNA encoding partly or completely the sequence of the first and second binding domain (e.g., sequences of the heavy and light chain, wherein the binding domain comprises a sequence of the heavy and light chain) obtained as described above in expression vectors such that the genes are operatively linked to the necessary expression control sequences such as transcription and translation control sequences. Expression vectors include plasmids, retroviruses, adenoviruses, adeno-associated viruses (AAV), plant viruses such as cauliflower mosaic virus, tobacco mosaic virus, cosmids, YAC, EBV derived episomes, and the like. DNA molecules can be ligated into a vector such that the sequences controlling transcription and translation in the vector operate the intended function of DNA transcription and translation regulation. The expression vector and expression control sequences may be selected so as to be compatible with the expression host cell used. DNA molecules encoding a part of or the full-length sequence of the first and second binding domains (e.g., sequences of the heavy and light chain, wherein the binding domain comprises a sequence of the heavy and light chain) can be inserted into separate vectors. In one embodiment of the invention, any combination of the above DNA molecules is introduced into the same expression vector. DNA molecules can be introduced into the expression vector by standard methods (e.g., ligation of complementary restriction sites on the antibody gene fragment and vector, or blunt end ligation if there are no restriction sites).

A suitable vector is one that encodes a functionally complete sequence of the human CH or CL immunoglobulin to design an appropriate restriction site so that any VH or VL sequence can be easily incorporated and expressed, as described above. NA- and LC-encoding genes into such vectors may contain intron sequences leading to an overall increase in protein antibody products by stabilizing the corresponding mRNA. Intron sequences are surrounded by splice donor and splice acceptor sites, which determine where RNA splicing will occur. Intron sequences may be located either within variable or constant regions of antibody chains or in both the variable and constant regions when several introns are used. Polyadenylation and transcription termination can be downstream the native chromosome site-encoded regions. The recombinant expression vector can also encode a signal peptide that facilitates production of antibody chains by the host cell. Antibody chain gene can be cloned into the vector such that the signal peptide is linked to the reading frame amino terminus of the immunoglobulin chain. The signal peptide can be an immunoglobulin signal peptide or a heterologous signal peptide (i.e., a signal peptide that is not of the immunoglobulin protein nature).

In addition to antibody chain genes, the recombinant expression vectors of the invention may carry regulatory sequences that control the expression of the antibody chain genes in a host cell. Those skilled in the art will appreciate that the design of the expression vector, including the selection of regulatory sequences, may depend on such factors as the selection of the host cell to be transformed, the level of expression of protein desired, etc. Preferred regulatory sequences for mammalian expression host cells include viral elements to ensure a high level of protein expression in mammalian cells, such as promoters and/or enhancers derived from retroviral LTR, cytomegalovirus (CMV) (e.g., CMV promoter/enhancer), Simian Virus 40 (SV40) (e.g., SV40 promoter/enhancer), adenovirus, (e.g., large adenovirus late promoter (AdMLP)), polyoma virus, as well as strong mammal promoters such as native immunoglobulin and actin promoters. For further description of viral regulatory elements, and sequences thereof, see., e.g., U.S. Pat. Nos. 5,168,062; 4,510,245; and 4,968,615. Methods for expression of binding molecules such as antibodies in plants, including a description of promoters and vectors, as well as the transformation of plants, are known in the art. See., e.g., U.S. Pat. No. 6,517,529. Methods for expression of polypeptides in bacterial cells or fungal cells, e.g., yeast cells, are also well known in the art.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665; and 5,179,017). For example, typically the selectable marker gene confers resistance to drugs, such as G418, hygromycin or methotrexate, to a host cell into which the vector is introduced. For example, selectable marker genes include dihydrofolate reductase gene (DHFR) (for use in dhfr-host cells with selection/MTX amplification), neo gene (for selection of G418) and glutamate synthetase gene.

The term "expression control sequence" as used herein means polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and, optionally, sequences that enhance protein secretion. The nature of such control sequences differs depending upon the host organism; in prokaryotes, such control sequences generally include a promoter, ribosomal binding site, and transcription termination sequence; in eukaryotes, generally, such control sequences include promoters and transcription termination sequences. The term "control sequences" includes at least all components whose presence is essential for expression and processing, and can also include additional components whose presence is useful, for example, leader sequences and fused cell sequences.

Host Cells

A further aspect of the invention relates to methods for producing anti-PD-L1 antibodies of the invention. One embodiment of the invention relates to a method for producing anti-PD-L1 antibodies as defined herein comprising providing a recombinant host cell capable of expressing an anti-PD-L1 antibody, cultivating said host cell under conditions suitable for the production of the anti-PD-L1 antibody, and recovering the produced anti-PD-L1 antibody. Anti-PD-L1 antibody produced by such expression in such recombinant host cells are referred to herein as "recombinant anti-PD-L1 antibody." The invention also relates to progeny cells of such host cells and to anti-PD-L1 antibodies obtained by the same way.

Nucleic acid molecules encoding anti-PD-L1 antibodies of the invention and vectors comprising these nucleic acid molecules may be used for transfection of a suitable mammalian, plant, bacterial or yeast host cell. The conversion may occur by any known method for introducing polynucleotides into a host-cell. Methods for introducing heterologous polynucleotides into mammalian cells are well known in the art and include dextran-mediated transfection, nucleic acid and positively charged polymer complex transfection, nucleic acid and calcium phosphate precipitation transfection, polybrene-mediated transfection, protoplast fusion, transfection by polynucleotides encapsulated in liposomes, and direct microinjection of the DNA into nuclei. In addition, nucleic acid molecules may be introduced into mammalian cells by viral vectors. Methods for transforming the cells are well known in the art. See., e.g., U.S. Pat. Nos. 4,399,216; 4,912,040; 4,740,461; and 4,959,455. Methods for transforming the plant cells are well known in the art, including, e.g., *Agrobacterium*-mediated transformation, biolistic transformation, direct injection, electroporation, and viral transformation. Methods for transforming the bacteria and yeast cells are also well known in the art.

Mammalian cell lines used as hosts for transformation are well known in the art and include many immortalized available cell lines. These include in particular Chinese Hamster Ovary cells (CHO), NS0 cells, SP2, HEK-293T-cells, Freestyle 293 cells (Invitrogen), NIH-3T3 cells, HeLa cells, baby hamster kidney (BHK) cells, African green monkey kidney cells (COS), human hepatocellular carcinoma cells (e.g., Hep G2), A549 cells, and a number of other cell lines. Cell lines are selected through determining which cell lines have high expression levels and provide desired characteristics of the protein produced. Other cell lines that may be used are insect cell lines, such as Sf9 or Sf21 cells. When recombinant expression vectors encoding the anti-PD-L1 antibodies are introduced into mammalian host cells, the antibodies are produced by culturing the host cells for a time sufficient for expression of the antibodies in the host cells or, more preferably, the release of the antibodies in a culture medium where host-cells grown. The anti-PD-L1 antibodies can be recovered from the culture medium using standard protein purification methods. Plant host cells, for example, include *Nicotiana, Arabidopsis*, duckweed, corn, wheat, potatoes, etc. Bacterial host cells include *E. coli* and *Streptomyces* species. Yeast host cells include *Schizosaccharomyces pombe, Saccharomyces cerevisiae* and *Pichia pastoris*.

In addition, producing level of the anti-PD-L1 antibodies of the present invention from production cell lines can be enhanced using a number of known methods. For example, glutamine synthetase gene expression system (GS system) is quite common for enhancing expression under certain conditions. GS system is discussed in general or partly in connection with EP patents 0216846, 0256055, 0323997, and 0338841.

The anti-PD-L1 antibodies from different cell lines or transgenic animals will likely differ by the glycosylation profile. However, all anti-PD-L1 antibodies encoded by the nucleic acid molecules described herein, or comprising the amino acid sequences set forth herein are part of this invention regardless of the binding molecule glycosylation status and in general regardless of the presence or absence of post-translational modifications.

Antibody Preparation

The invention also relates to methods and processes for producing anti-PD-L1 antibodies and antigen-binding fragments thereof.

Monoclonal Antibodies

Monoclonal antibodies may be made using the hybridoma-based method first described by Kohler et al., Nature, 256, 1975, p. 495, or may be made by recombinant DNA methods (U.S. Pat. No. 4,816,567).

In the hybridoma-based method, a mouse or other appropriate host animal, such as a hamster, is immunized as hereinabove described to elicit lymphocytes that produce or are capable of producing antibodies able to specifically bind to the protein used for immunization. Alternatively, lymphocytes may be immunized in vitro. After immunization, lymphocytes are isolated and fused with myeloma cell line using a suitable fusing agent, such as polyethylene glycol, to form hybridoma cells (Goding, Monoclonal Antibodies: Principles and Practice, Academic Press, 1986, pp. 59-103).

The hybridoma cells thus prepared are plated and grown in a suitable culture medium that preferably contains one or more substances that inhibit the growth or survival of the unfused, parental myeloma cells. For example, if the parental myeloma cells lack the hypoxanthine guanine phosphoribosyl transferase enzyme (HGPRT or HPRT) the hybridoma culture medium typically is to include hypoxanthine, aminopterin, and thymidine (HAT medium), i.e. substances that prevent the growth of HGPRT-deficient cells.

Preferred myeloma cells used as a component for cell fusion are cells that are readily to fuse, maintain a stable high level of antibody production by selected antibody-producing cells and are sensitive to the selective medium on which unbound parent cells are selected. Preferred myeloma cell lines are murine myeloma lines, such as those derived from MOPC-21 and MPC-11 mouse tumours available from the Salk Institute Cell Distribution Center, San Diego, Calif., USA, and SP-2 or X63-Ag8-653 cells available from the American Type Culture Collection, Rockville, Md., USA. Human myeloma and mouse-human heteromyeloma cell lines also have been described for the production of human monoclonal antibodies (Kozbor, J. Immunol., 133, 1984, p. 3001; and Brodeur et al, Monoclonal Antibody Production Techniques and Applications, Marcel Dekker Inc., New York, 1987, pp. 51-63).

Preferably, the binding specificity of monoclonal antibodies produced by hybridoma cells is determined by immunoprecipitation or by in vitro binding assays, such as radioimmunoassay (RIA) or enzyme-linked immunoabsorbent assay (ELISA).

The binding affinity of a monoclonal antibody or portion thereof also can be determined by the Scatchard analysis described in Munson et al, Anal. Biochem., 107, 1980, p. 220.

Upon the identification of hybridoma cells that produce antibodies of the desired specificity, affinity, and/or activity, the clones may be subcloned by limiting dilution method and grown by standard methods (Goding, Monoclonal Antibodies: Principles and Practice, Academic Press, 1986, pp. 59-103). Useful culture media for this purpose include, for example, D-MEM or RPMI-1640 medium. In addition, the hybridoma cells may be grown in vivo as ascites tumours in animals, for example, by intraperitoneal (i.p.) injection of cells into mice.

The monoclonal antibodies secreted by the subclones can be separated from the culture medium, ascites fluid, or serum by conventional immunoglobulin purification methods such as affinity chromatography (for example, protein A- or protein Q-Sepharose) or ion-exchange chromatography, hydroxylapatite chromatography, gel electrophoresis, dialysis and the like.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce immunoglobulin protein, to provide the synthesis of monoclonal antibodies in the recombinant host cells. Review articles on recombinant expression in bacteria of DNA encoding the antibody see Skerra et al., Curr. Opinion in Imunol., 5, 1993, pp. 256-262, and Pliickthun, Immunol. Revs. 130, 1992, pp. 151-188.

In a further embodiment of the invention, monoclonal antibodies or antibody fragments can be isolated from antibody phage libraries generated using the techniques described in McCafferty et al., Nature, 348, 1990, pp. 552-554. Clackson et al., Nature, 352, 1991, pp. 624-628 and Marks et al., J. Mol. Biol., 222, 1991, pp. 581-597 describe the isolation of murine and human antibodies, respectively, using phage libraries. Subsequent publications describe the production of high-affinity (nM range) human antibodies by chain shuffling (Marks et al., Bio/Technology, 10, 1992, pp. 779-783), as well as combinatorial infection and in vivo recombination as a strategy for constructing very large phage libraries (Waterhouse et al., Nucl. Acids. Res., 21, 1991, pp. 2265-2266). Thus, these techniques are viable alternatives to traditional monoclonal antibody hybridoma-based techniques for isolation of monoclonal antibodies.

DNA encoding the antibody can also be modified, for example, so as to obtain chimeric or fused antibody polypeptides, e.g. by replacing the sequence of heavy- and light-chain ($C_H$ and $C_L$) constant regions to the homologous murine sequences (U.S. Pat. No. 4,816,567; and Morrison, et al., Proc. Natl. Acad. Sci. USA: 81, 1984, p. 6851) or by covalently joining the immunoglobulin-coding sequence to all or part of the sequence encoding a non-immunoglobulin polypeptide (heterologous polypeptide). Non-immunoglobulin polypeptide sequences can be replaced with antibody constant regions or replaced with variable regions of the antibody antigen-binding site, creating a chimeric bivalent antibody that contains one antigen-binding site having specificity for an antigen and another antigen-binding site having specificity for another antigen.

Humanized Antibodies

Methods for creating "humanized" antibodies in non-human animals are known in the art. Preferably, the humanized antibody has one or more amino acid residues incorporated therein derived from a non-human source. These amino acid residues derived from a non-human source are often referred to as "import" residues since they are usually obtained from an "imported" variable region. Humanization can be essentially performed following the method of Winter and co-workers (Jones et al., Nature, 321, 1986, pp. 522-525; Riechmann et al., Nature, 332, 1988, pp. 323-327; Verhoeyen et al., Science, 239, 1988, pp. 1534-1536) by substituting hypervariable region sequences for the corresponding sequences of a human antibody. Accordingly, "humanized" antibodies are chimeric antibodies (U.S. Pat. No. 4,816,567) wherein a region that is substantially less than an intact human variable region has been substituted by the corresponding sequence from the non-human species. In practice, humanized antibodies are typically human antibodies wherein some hypervariable region residues and possibly some FR residues are substituted by residues from analogous regions in rodent antibodies.

The choice of human variable domains, both light and heavy, to be used in making the humanized antibodies is very important to reduce antigenicity and HAMA-response (human anti-murine antibody) when the antibody is intended for human treatment. According to the so-called "best-fit" method, the sequence of the variable region of a rodent antibody is screened against the entire library of known human variable-region sequences. The human V-region sequence, which is the closest to that of the rodent, is identified and a human framework (FR) suitable for use in a humanized antibody is selected within it (Sims et al., J. Immunol., 151, 1993, p. 2296); Chothia et al., J. Mol. Biol., 196, 1987, p. 901). Another method uses a particular framework derived from the consensus sequence of a particular subgroup of all human antibody light or heavy chains. The same framework may be used for several different humanized antibodies (Carter et al., Proc. Natl. Acad. Sci. USA: 89, 1992, p. 4285; Presta et al., J. Immunol., 151, 1993, p. 2623).

It is further important that antibodies be humanized with retention of high binding affinity for the antigen and other favourable biological properties. To achieve this goal, according to a preferred method, humanized antibodies are prepared by an analysis process of the parental sequences and various humanized products using conceptual three-dimensional models of the parental and humanized sequences. Three-dimensional immunoglobulin models are commonly available and are familiar to those skilled in the art. Computer programs are available, which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

The humanized antibody can be an antibody fragment, such as a Fab fragment, optionally conjugated to one or more cytotoxic agent(s) to create an immunoconjugate. Alternatively, the humanized antibody can be a full-length antibody, e.g., a full-length IgG1 antibody.

Human Antibodies and Phage Display Library Technique

As an alternative to humanization, human antibodies can be obtained. For example, currently, it is possible to produce transgenic animals (for example, mice) that upon immunization are capable of producing a full spectrum of human antibodies in the absence of endogenous immunoglobulin production. For example, it has been described that the homozygous deletion of the antibody heavy-chain joining region ($J_H$-segment) gene in chimeric and germ-line mutant mice results in complete inhibition of endogenous antibody production. Transfer of the human germ-line immunoglobulin gene array into such germ-line mutant mice results in the production of human antibodies upon antigen challenge (see, for example, Jakobovits et al., Proc. Natl. Acad. Sci. USA: 90, 1993, p. 2551; Jakobovis et al., Nature, 362, 1993, pp. 25-258; Bruggemann et al., Year in Immuno., 7, 1993, p. 33; U.S. Pat. Nos. 5,545,806; 5,569,825; 5,591,669 (all of GenPharm); U.S. Pat. No. 5,545,807; and WO 97/17852)

Alternatively, to produce human antibodies and antibody fragments in vitro from the immunoglobulin variable region (V) spectrum from the immunized donors, phage display technology can be used (McCafferty et al., Nature, 348, 1990, pp. 552–553). According to this technique, the antibody V region genes are cloned in the reading frame with either a major or minor gene of the envelope protein of a filamentous bacteriophage such as M13 or fd and presented as functional antibody fragments on the surface of the phage particle. Since the filamentous particle contains a copy of the single-stranded DNA of the phage genome, the functional property-based selections of the antibody also result in the selection of a gene encoding an antibody that has said properties. Thus, the phage mimics some properties of the B-cell. A phage presentation can be performed in various formats (review see, for example, Johnson Kevin S. and Chiswell David J., Current Opinion in Structural Biology, 3, 1993, pp. 564-571). For phage presentation, different sources of V-gene segments can be used. Clackson et al., Nature, 352, 1991, pp. 624-628 isolated various sets of anti-oxazolone antibodies from a small arbitrary combinatorial library of V-genes derived from the spleen of immunized mice. It is possible to design a spectrum of V genes obtained from immunized human donors and antibodies to a different set of antigens (including autoantigens) can be isolated in general according to the methods described in Marks et al., J. Mol. Biol., 222, 1991, pp. 581-597, or in Griffith et al., EMBO J., 12, 1993, pp. 725-734) (see also U.S. Pat. Nos. 5,565,323; and 5,537,905).

As described above, human antibodies can also be produced in vitro by activated B-cells (see U.S. Pat. Nos. 5,567,610 and 5,229,275).

Antibody Fragments

In certain cases, it is advisable to use antibody fragments, rather than complete antibodies. The smaller size of the fragments contributes to their rapid clearance and may contribute to better penetration into solid tumours.

Various techniques have been developed for the production of antibody fragments. Traditionally, these fragments were derived via proteolytic digestion of intact antibodies (see, e.g., Morimoto et al., Journal of Biochemical and Biophysical Methods 24, 1992, pp. 107-117, and Brennan et al., Science, 229, 1985, p. 81). These fragments, however, can now be produced directly by recombinant host cells. Fab, Fv and scFv fragments of antibodies can be expressed and secreted from *E. coli* that allow facilitating the production of large amounts of these fragments. Antibody fragments can be isolated from the above phage antibody libraries. In another embodiment, Fab'-SH-fragments can be directly isolated from *E. coli* and chemically coupled to form F(ab')$_2$-fragments (Carter et al, Bio/Technology, 10, 1992, pp. 163-167). According to another approach, F(ab')$_2$-fragments can be isolated directly from the culture of recombinant host cells. The Fab and F(ab')$_2$ fragment with an increased in vivo half-life, in which the residues of the epitope-binding receptor are retained, are described in U.S. Pat. No. 5,869,046. Other procedures for the preparation of antibody fragments should be apparent to those skilled in the art. In other embodiments, the selected antibody is a single chain Fv fragment (scFv) (see WO 93/16185, U.S. Pat. Nos. 5,571,894, and 5,587,458). Fv and sFv are the only species with intact binding sites lacking constant regions; as a result, they can be used for reduced non-specific binding when used in vivo. The fused proteins carrying sFv can be designed to produce a fusion of the effector protein either at the N- or C-terminus of sFv (see Antibody Engineering, ed. Borrebaeck, above). The antibody fragment may also be a "linear antibody," for example, as described in U.S. Pat. No. 5,641,870. Such fragments of the linear antibody can be monospecific or bispecific.

Bispecific Antibodies

Bispecific antibodies are antibodies that are able to specific binding to two different epitopes. For example, bispecific antibodies can bind to two different epitopes of the PD-L1 protein. Other bispecific antibodies can carry a binding site for PD-L1 in combination with a binding site for another protein. Bispecific antibodies can be obtained as full-length antibodies or antibody fragments (e.g., F(ab')$_2$ fragments of bispecific antibodies).

Methods for making bispecific antibodies are well known in the art. Traditional production of full-length bispecific antibodies is based on the coexpression of two immunoglobulin heavy chain-light chain pairs, where both chains have different specificities (Millstein et al, Nature, 305, 1983, pp. 537-539). Because of the random assortment of immunoglobulin heavy and light chains, these hybridomas (quadromas) produce a potential mixture of 10 different antibody molecules, of which only one has the correct bispecific structure. Purification of the correct molecule, which is usually done by several affinity chromatography steps, is rather cumbersome, and the product yield is low. Similar procedures are disclosed in WO 93/08829, and in Traunecker et al., EMBO J., 10, 1991, pp. 3655-3659.

According to a different approach, antibody variable domains with the desired binding specificity (antibody antigen-binding sites) are fused to immunoglobulin constant region sequences. The fusion preferably is performed with an Ig-heavy chain constant region comprising at least part of hinge $C_H2$ and $C_H3$ regions. It is preferred to have the first heavy-chain constant region ($C_H1$) containing the site necessary for light chain binding, present in at least one of the fusions. DNAs encoding the immunoglobulin heavy chain fusions and, if desired, the immunoglobulin light chain, are inserted into separate expression vectors and are co-transfected into a suitable host organism. This provides for great flexibility in adjusting the mutual proportions of the three polypeptide fragments in embodiments when unequal ratios of the three polypeptide chains are used in the construct to provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific molecule from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121, 1986, p. 210.

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ region. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., with alanine or threonine). This provides a mechanism for increasing the yield of the heterodimer over other unwanted end-products such as homodimers.

Bispecific antibodies include cross-linked antibodies or "heteroconjugates." For example, one of the antibodies in the heteroconjugate can be coupled to avidin, the other to biotin. Such antibodies can, for example, be used to target immune system cells to unwanted cells (U.S. Pat. No. 4,676,980), and for treatment of HIV infection (WO 91/00360, WO 92/200373 and EP 03089). Heteroconjugate antibodies may be made using any convenient cross-linking methods. Suitable cross-linking agents are well known in the art and are described in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229, 1985, p. 81 describe a procedure wherein intact antibodies are proteolytically cleaved to generate F(ab')$_2$ fragments. These fragments are reduced in the presence of the dithiol complexing agent, such as sodium arsenite, to stabilize vicinal dithiols and prevent intermolecular disulfide bonds formation. The Fab' fragments generated are then converted to thionitrobenzoate (TNB) derivative. One of the Fab'-TNB derivatives is then reconverted to the Fab'-thiol by reducing with mercaptoethylamine and is mixed with an equimolar amount of the other Fab'-TNB derivative to create the bispecific antibody. The bispecific antibodies produced can be used as agents for the selective immobilization of enzymes.

Current progress makes possible to facilitate Fab'-SH fragments be directly recovered from *E. coli* that can be chemically coupled to form bispecific antibodies. Shalaby et al, J. Exp. Med., 175, 1992, pp. 217-225 described the production of a fully humanized bispecific antibody molecule F(ab')$_2$ fragment. Each Fab' fragment was separately secreted from *E. coli* and subjected to direct chemical coupling in vitro to form the bispecific antibody. The bispecific antibody thus obtained had the ability to bind to cells that are characterized by overexpression of the ErbB2 receptor and to normal human T-cells, as well as to stimulate the lytic activity of human cytotoxic lymphocytes targeted by a human breast tumour.

Various techniques for making and isolating bispecific antibody fragments directly from recombinant cell culture have also been described. For example, bispecific antibodies have been produced using leucine "zippers" (Kostelny et al., J. Immunol., 148(5), 1992, pp. 1547-1553). The leucine "zipper" peptides from the Fos and Jun proteins were linked to the Fab' fragments of two different antibodies by gene fusion. The antibody homodimers were reduced in the hinge region to form monomers and then re-oxidized to form the antibody heterodimers. This method can also be used to produce antibody homodimers. The "diabody" technology described by Hollinger et al., Proc. Natl. Acad. Sci. USA, 90, 1993, pp. 6444-6448, is an alternative mechanism for making bispecific antibody fragments. The fragments comprise a heavy-chain variable (VH) region connected to a light chain variable (VL) region by a linker that is too short to allow pairing between the two domains on the same chain. Accordingly, the VH and VL regions of one fragment are forced to pair with the complementary VL and VH regions of another fragment, thereby forming two antigen-binding sites. Another strategy for making bispecific antibody fragments based on the use of single-chain Fv (sFv) dimers has also been reported (see Gruber et al, J. Immunol, 152, 1994, p. 5368).

Antibodies having more than two valencies also fall within the scope of the invention. For example, trispecific antibodies can be prepared (Tutt et al, J. Immunol., 147, 1991, p. 60).

Multivalent Antibodies

The multivalent antibody can be internalized (and/or dissimilated) by a cell expressing the antigen to which the antibody binds faster than the bivalent antibody. The antibodies of the present invention may be multivalent antibodies (non-IgM class) with three or more antigen-binding sites (e.g., tetravalent antibodies) that can be readily prepared by recombinant expression of the nucleic acid encoding the polypeptide chains of the antibody. The multivalent antibody may comprise a dimerized domain and three or more antigen-binding sites. The preferred dimerized domain comprises (or consists of) an Fc fragment or hinge region. In such a case, the antibody should contain an Fc fragment and three or more antigen-binding sites located at the N-terminus with respect to the Fc fragment. As used herein, a preferred multivalent antibody comprises (or consists of) 3 to about 8, but preferably 4, antigen-binding sites. The multivalent antibody comprises at least one polypeptide chain (and preferably two polypeptide chains), wherein the polypeptide chain(s) comprise(s) two or more variable regions. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise the following chain: VH-CH1-flexible linker-VH-CH1-Fc region; or VH-CH1-VH-CH1-Fc region. The multivalent antibody provided herein preferably further comprises at least 2 (and preferably 4) light chain variable region polypeptides. The multivalent antibody provided herein may, for instance, comprise from about 2 to about 8 light chain variable region polypeptides. As used herein, the light chain variable region polypeptides comprise a light chain variable region and optionally further comprise a CL region.

Pharmaceutical Compositions

Another aspect of the invention is a pharmaceutical composition comprising as an active ingredient (or as a single active ingredient) an antibody that is specific for PD-L1. The pharmaceutical composition can include any anti-PD-L1 antibody as described herein. In some embodiments of the invention, the compositions are for improving, preventing or treating disorders that may be associated with the PD-L1 activity.

In general, the anti-PD-L1 antibodies of the invention are suitable for use as dosage forms in combination with one or more pharmaceutically acceptable excipient, for example as described below.

The pharmaceutical compositions of the invention may contain at least one anti-PD-L1 antibody and one or more additional binding molecules (e.g., antibodies) that are targeted to one or more respective surface receptors.

The pharmaceutical composition is a "sterile" one when it is aseptic, i.e. free from living microorganisms and their spores.

The pharmaceutical composition is a "stable" one when the active agent retains its physical stability and/or chemical stability and/or biological activity throughout its shelf life at a storage temperature, e.g., at a temperature of 2-8° C. It is desired that the active agent retains its physical and chemical stability, as well as its biological activity. The storage period is selected based on the results of the stability study under accelerated and natural storage conditions.

The term "excipient" is used herein to describe any ingredient other than the compound(s) of the invention. The choice of inert excipient depends largely on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and similar physiologically compatible substances. Some examples of pharmaceutically acceptable excipients are water, saline, phosphate buffer, dextrose, glycerol, ethanol and the like, and combinations thereof. In many cases, it is preferred to include isotonic agents, for example, sugars, polyalcohols such as mannitol, sorbitol, or sodium chloride into the composition. Further examples of pharmaceutically acceptable substances are wetting agents or minor auxiliary substances such as wetting or emulsifying agents, preservatives or buffers, which enhance the shelf life or effectiveness of the antibody.

By "buffering agent" is meant a solution capable of maintaining the pH value due to the interaction between the acidic and alkaline components that make up its composition. In general, the pH of the pharmaceutical composition is preferably between 4.5 to 7.0. Examples of buffers that are known to those skilled in the art and can be found in the literature include, but are not limited to, histidine, citrate, succinate, acetate, phosphate, phosphate-salt, citrate-phosphate buffers, and tromethamine-based buffers and the like, or suitable mixtures.

By "isotonic agents" is meant an auxiliary substance or a mixture of two or more auxiliary substances that provide an isotonic osmotic pressure of the solution. "Isotonic" is considered a solution creating an osmotic pressure of about 250 to 350 mOsm/kg. As isotonic agents, polyols, mono- and disaccharides, amino acids, metal salts, for example, sodium chloride, etc., can be used but not limited to. The term "hypotonic" describes a composition with an osmotic pressure below that of human blood. Correspondingly, the term "hypertonic" describes a composition with an osmotic pressure above that of human blood.

The term "surfactant" (also called detergent or surfactant or SAS) as used herein refers to an excipient that can change the surface tension of a liquid antibody preparation. In certain embodiments, the surfactant reduces the surface tension of a liquid antibody preparation. In other embodiments, the "surfactant" may contribute to an improvement in colloid stability or solubility of any antibody in the preparation. The surfactant may reduce aggregation of the produced antibody preparation and/or minimize the formation of particulates in the preparation and/or reduce the adsorption. The surfactant may also improve the stability of the antibody during and after a freeze/thaw cycle and during shaking. Surfactants can be ionic or non-ionic. Exemplary non-ionic surfactants that can be included in the formulations of the present invention include, e.g., alkyl poly (ethylene oxide), alkyl polyglucosides (e.g., octyl glucoside and decyl maltoside), fatty alcohols such as cetyl alcohol and oleyl alcohol, Cocamide MEA, Cocamide DEA, and cocamide TEA. Specific non-ionic surfactants that can be included in the formulations of the present invention include, e.g., polysorbates such as polysorbate 20 (Tween 20), Polysorbate 28, Polysorbate 40, Polysorbate 60, Polysorbate 65, Polysorbate 80 (Tween 80), Polysorbate 81, and polysorbate 85; poloxamers such as poloxamer 188 (Kolliphor P188), poloxamer 407; polyethylene-polypropylene glycol; or polyethylene glycol (PEG), ethylene- and propylene glycol copolymers (e.g., Pluronic PF68 etc).

By "stabilizer" is meant an auxiliary substance or a mixture of two or more auxiliary substances that provide the physical and/or chemical stability of the active agent. As stabilizers, amino acids can be used, for example but not limited to, arginine, histidine, glycine, lysine, glutamine, proline; surfactants, for example but not limited to, polysorbate 20 (trade name Tween 20), polysorbate 80 (trade name Tween 80), polyethylene-polypropylene glycol and its copolymers (trade names Poloxamer), Pluronic, sodium dodecyl sulfate (SDS); antioxidants, for example but not limited to, methionine, acetylcysteine, ascorbic acid, monothioglycerol, salts of sulfuric acids, and the like; chelating agents, for example but not limited to, EDTA, DTPA, sodium citrate and the like.

A "pharmaceutically acceptable acid" includes inorganic and organic acids that are non-toxic at the concentration and a form, in which they are formulated. For example, suitable inorganic acids include hydrochloric, perchloric, hydrobromic, hydroiodic, nitric, sulfuric, sulfonic, sulfuric, sulfanilic, phosphoric, carbonic, etc. Suitable organic acids include straight and branched-chain alkyl, aromatic, cyclic, cycloaliphatic, arylaliphatic, heterocyclic, saturated, unsaturated, mono, di- and tri-carboxylic, including for example, formic, acetic, 2-hydroxyacetic, trifluoroacetic, phenylacetic, trimethylacetic, t-butyl acetic, anthranilic, propanoic, 2-hydroxypropanoic, 2-oxopropanoic, propandioic, cyclopentanepropionic, cyclopentane propionic, 3-phenylpropionic, butanoic, butandioic, benzoic, 3-(4-hydroxybenzoyl)benzoic, 2-acetoxy-benzoic, ascorbic, cinnamic, lauryl sulfuric, stearic, muconic, mandelic, succinic, embonic, fumaric, malic, maleic, hydroxymaleic, malonic, lactic, citric, tartaric, glycolic, glyconic, gluconic, pyruvic, glyoxalic, oxalic, mesylic, succinic, salicylic, phthalic, palmoic, palmeic, thiocyanic, methanesulphonic, ethanesulphonic, 1,2-ethanedisulfonic, 2-hydroxyethanesulfonic, benzenesulphonic, 4-chorobenzenesulfonic, napthalene-2-sulphonic, p-toluenesulphonic, camphorsulphonic, 4-methylbicyclo [2.2.2]-oct-2-ene-1-carboxylic, glucoheptonic, 4,4'-methylenebis-3-(hydroxy-2-ene-1-carboxylic acid), hydroxynapthoic.

"Pharmaceutically-acceptable bases" include inorganic and organic bases that are non-toxic at the concentration and form, in which they are formulated. For example, suitable bases include those formed from inorganic base forming metals such as lithium, sodium, potassium, magnesium, calcium, ammonium, iron, zinc, copper, manganese, aluminum, N-methylglucamine, morpholine, piperidine and organic nontoxic bases including, primary, secondary and tertiary amines, substituted amines, cyclic amines and basic ion exchange resins, [e.g., N(R')4+ (where R' is independently H or $C_{1-4}$ alkyl, e.g., ammonium, Tris)], for example, isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, trimethamine, dicyclohexylamine, choline, and caffeine. Additional pharmaceutically acceptable acids and bases useful with the present invention include those which are derived from the amino acids, for example, histidine, glycine, phenylalanine, aspartic acid, glutamic acid, lysine, and asparagine.

The "diluent" of interest as used herein is one that is pharmaceutically acceptable (safe and non-toxic for administration to a human) and is useful for the preparation of a liquid composition, such as a composition reconstituted after lyophilization. Exemplary diluents include water, bacteriostatic water for injection (BWFI), pH buffered solution (e.g., phosphate-buffered saline), sterile saline solution, Ringer's solution or dextrose solution. In an alternative embodiment, diluents can include aqueous solutions of salts and/or buffers.

A "preservative" is a compound that can be added to the composition provided herein to reduce bacterial activity. The addition of a preservative may, for example, facilitate the production of a multi-use (multiple-dose) composition. Examples of potential preservatives include octadecyl dimethyl benzyl ammonium chloride, hexamethonium chloride, benzalkonium chloride (a mixture of alkylbenzyldimethylammonium chlorides, in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. The most preferred preservative provided herein is benzyl alcohol.

The term "lyophilized" as used herein refers to a preparation that has been subjected to a process known in the art as freeze-drying including freezing the preparation and then sublimation ice from the frozen content.

The term "amino acid" as used herein denotes an amino acid (a free amino acid, i.e. not an amino acid in a peptide or protein sequence). Amino acids, as used herein, comprise but is not limited to arginine, glycine, lysine histidine, glutamic acid, aspartic acid, isoleucine, leucine, alanine, phenylalanine, tryptophan, serine, methionine and proline, for instance.

Pharmaceutical compositions of the invention and methods for preparing thereof is undoubtedly apparent to those skilled in the art. Such compositions and methods for preparing thereof can be found, e.g., in Remington, The Science and Practice of Pharmacy, 21th Edition, Troy, Beringer., Lippincott Williams and Wilkins., Philadelphia, Pa. 2006. Production of pharmaceutical compositions should preferably meet the requirements of GMP (Good Manufacturing Practice).

The pharmaceutical composition of the present invention may be manufactured, packaged, or generally distributed as a single unit dose or a plurality of single unit doses. The term "single unit dose" as used herein means a discrete amount of the pharmaceutical composition comprising a predetermined amount of the active ingredient. The amount of the active ingredient is generally equal to the dosage of the active ingredient, which would be administered to a subject, or a convenient part of the dosage, for example, half or third of such dosage.

Any method for administering peptides, proteins or antibodies accepted in the art can be suitably used for the anti-PD-L1 antibody of the invention.

The pharmaceutical compositions of the present invention are generally suitable for parenteral administration. As used herein, the term "parenteral administration" of a pharmaceutical composition includes any route of administration, which is characterized by physical disturbance of the subject tissue integrity and administration of the pharmaceutical composition through the breach in the tissue, which generally results in direct contact with the bloodstream, into muscle, or into an internal organ. Thus, parenteral administration includes but is not limited to administering a pharmaceutical composition by injection of the composition by administering the composition through a surgical incision, by application of the composition through a tissue-penetrating non-surgical wound, etc. In particular, it is assumed that parenteral administration includes but is not limited to subcutaneous, intraperitoneal, intramuscular, intravenous, intraarterial, intrathecal, intraventricular, intraurethral, intracranial, intraarticular injection or infusions; and renal dialysis and infusion techniques. Intratumoral delivery, for example, intratumoral injection, may also be useful. Also, regional perfusion is contemplated. Preferred embodiments include the intravenous and subcutaneous routes.

Dosage forms of the pharmaceutical compositions suitable for parenteral administration conveniently comprise the active ingredient in association with a pharmaceutically acceptable carrier/excipient, such as sterile water or sterile isotonic saline. Such dosage forms can be prepared, packaged, or distributed in a form suitable for bolus administration or for continuous administration. Injection dosage forms may be prepared, packaged, or distributed in unit dosage form, e.g., in ampoules or in multi-dose containers containing a preservative. Dosage forms for parenteral administration include but are not limited to suspensions, solutions, emulsions in oily or aqueous bases, pastes and the like. Such dosage forms may also contain one or more additional ingredients including but not limited to suspending, stabilizing, or dispersing agents. In one embodiment of the compositions of the invention for parenteral administration, the active ingredient is provided in the dry form (i.e., powder or granules) to dissolve with a suitable base (e.g., sterile pyrogen-free water) prior to parenteral administration of the formulation reconstituted. Parenteral dosage forms also include aqueous solutions that may contain fillers such as salts, carbohydrates and buffering agents (preferably to a pH of from 3 to 9 and more preferably to a pH of from 4.5 to 7), but for some applications the more suitable dosage form can be a sterile nonaqueous solution or dry form for use in conjunction with a suitable base, such as sterile pyrogen-free water. An example of parenteral administration forms includes solutions or suspensions in sterile aqueous solutions, for example, aqueous propylene glycol or dextrose solutions. Such dosage forms can be optionally buffered. Other suitable dosage forms for parenteral administration may include those that comprise the active ingredient in microcrystalline form or in a liposomal preparation. Dosage forms for parenteral administration may be made for immediate and/or modified release. Dosage forms with modified release include delayed, sustained, pulsed, controlled, targeted and programmed release.

For example, in one aspect, sterile injection solutions can be prepared by incorporating the required amount of trispecific anti-PD-L1 antibody in the appropriate solvent with one or a combination of ingredients listed above, as required, followed by filter sterilization. Generally, dispersions are prepared by incorporating the active compound into a sterile solvent that contains the basic dispersion medium and the required other ingredients from those listed above. In the case of sterile powders for the preparation of sterile injection solutions, methods for preparing are freeze-drying (lyophilization), which yields a powder of the active ingredient plus any additional desired ingredient from a previously sterile-filtered solution thereof. The proper fluidity of the solution can be maintained, for example, by the use of coating materials such as lecithin, by the maintenance of the required particle size in the case of dispersions, and using surfactants. Prolonged absorption of the injection compositions can be accomplished by including into the composition an absorption delaying agent, for example, monostearate and gelatin, and/or by a modified release coating (e.g., slow release coatings).

Anti-PD-L1 antibody of the invention can also be administered intranasally or by inhalation, typically in the form of a dry powder (either alone, as a mixture or in the form of particles of mixed components, for example, mixed with a suitable pharmaceutically acceptable filler) from a dry powder inhaler, such as an aerosol pressurized container, pump, spray, atomizer (preferably atomizer, which uses the principle electrohydrodynamics to produce a fine mist) or nebulizer wherein in use or not in use a suitable propellant, or as nasal drops.

The pressurized container, pump, spray, atomizer, or nebuliser generally contain a solution or suspension of a binding molecule of the present invention, including, for example, a suitable agent for dispersing, dissolving or extending release of the active, a propellant as a solvent.

Prior to use in a dry powder or suspension, the medication is usually micronised to a size suitable for delivery by inhalation (typically less than 5 microns). This may be achieved by any appropriate comminuting method, such as milling in a spiral jet mill, jet milling fluidized bed, supercritical fluid treatment to form nanoparticles, high-pressure homogenisation, or spray drying.

Capsules, blisters and cartridges for use in an inhaler or insufflator may be configured to contain a powder mix of a compound of the invention and a suitable powder base and an activity modifier.

A suitable formula of the solution for use in an atomizer that uses electrohydrodynamics principle to produce a fine mist may contain a suitable dose of an anti-PD-L1 antibody of the invention per actuation and the volume per pressing may vary, e.g., from 1 µl to 200 µl, more preferably from 1 µl to 100 µl.

To the dosage forms of the present invention intended for inhaled/intranasal administration, suitable flavouring agents may be added, such as menthol and levomenthol, or sweeteners, such as saccharin or sodium saccharin.

Dosage forms for parenteral administration may be made for immediate and/or modified release. Dosage forms with modified release include delayed, sustained, pulsed, controlled, targeted and programmed release.

In the case of dry powder inhalers and aerosols, the dosage unit is established by means of a valve that delivers a metered amount. Units according to the present invention is usually set to administer a metered dose or "injection" of the binding molecule of the invention. The total daily dose will generally be administered in a single dose or more frequently as divided doses throughout the day.

The anti-PD-L1 antibody of the invention may also be configured in the dosage form for oral administration. Oral administration may involve swallowing so that the compound enters the gastrointestinal tract and/or buccal, lingual or sublingual enters the bloodstream directly from the mouth.

Dosage forms suitable for oral administration include solid, semi-solid and liquid systems such as tablets; soft or hard capsules containing multi- or nanoparticles, liquids, or powders; lozenges (including liquid-filled); chewable forms;

gels; rapidly soluble dosage forms; films; suppositories; sprays; and buccal/mucoadhesive patches.

Liquid dosage forms include suspensions, solutions, syrups and elixirs. Such formulations may be employed as fillers in soft or hard capsules (e.g., from gelatin or hydroxypropylmethylcellulose) and typically comprise a carrier, for example, water, ethanol, polyethylene glycol, propylene glycol, methylcellulose, or a suitable oil, and one or more emulsifiers and/or suspending agents. Liquid dosage forms may also be prepared by reduction of a solid, for example, from a sachet.

Therapeutic Use of Anti-PD-L1 Antibody of Invention

In one aspect, the anti-PD-L1 antibody of the present invention is used in the treatment of diseases and disorders that are associated with PD-L1 activity, for example, a disease or disorder selected from the group: HNSCC (head and neck squamous cell carcinoma), cervical cancer, cancer of unknown primary, glioblastoma, oesophageal cancer, bladder cancer, TNBC (triple negative breast cancer), CRC (colorectal cancer), hepatocellular carcinoma, melanoma, NSCLC (non-small cells lung cancer), kidney cancer, ovarian carcinoma, Hodgkin's lymphoma, CRC MSI (colorectal cancer with high-frequency microsatellite instability).

In one aspect, the subject of the treatment or the patient is a mammal, preferably a human subject. The above subject may be male or female of any age.

In the case of a tumor (e.g., cancer), the therapeutically effective amount of the antibody or antibody fragment (e.g., the antibody or antibody fragment that specifically binds to PD-L1) can reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve, to some extent, one or more of the symptoms associated with the disorder. The antibody or antibody fragment can, to some extent, prevent growth and/or kill existing cancer cells, it may provide a cytostatic and/or cytotoxic effect. For cancer therapy, the efficacy can, for example, be measured by assessing lifetime, time to disease progression (TTP), response rate (RR), response duration and/or quality of life.

As used herein, the terms "concomitant prescription", "concomitantly prescribed" and "in combination with" referring to the anti-PD-L1 antibody with one or more other therapeutic agents are considered to mean, refer or include:

1) simultaneous administration of such combination of the anti-PD-L1 antibody of the invention and a therapeutic agent to a patient in need of treatment, when such components are formulated together into one dosage form from which said components are released practically at the same time to said patient, 2) simultaneous administration of such combination of the anti-PD-L1 antibody of the invention and a therapeutic agent to a patient in need of treatment, when such components are formulated separately in different dosage forms which introduction takes place almost at the same time to said patient, whereupon said components are released substantially simultaneously to said patient, 3) sequential administration of such combination of the anti-PD-L1 antibody of the invention and a therapeutic agent to a patient in need of treatment, when such components are formulated apart from each other into separate dosage forms which are taken sequentially in time by said patient with a significant time interval between each administration, whereupon said components are released at substantially different times to said patient; and 4) sequential administration of such combination of the anti-PD-L1 antibody of the invention and a therapeutic agent to a patient in need of treatment, when such components are formulated together into a single dosage form from which the release of these components occurs in a controlled manner whereupon they are concurrently, consecutively or together released into the same time and/or different times to said patient, where each part may be administered by one or by different routes.

The anti-PD-L1 antibody of the invention can be prescribed without an additional therapeutic treatment, i. e., as an individual therapy. Furthermore, treatment of the anti-PD-L1 antibody of the present invention may include at least one additional therapeutic treatment (combination therapy). In some embodiments, the anti-PD-L1 antibody can be administered together or be formulated with another medicament/medication for cancer treatment.

The term "cytotoxic agent", as used herein, refers to a substance that inhibits or prevents the function of cells and/or causes the destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and cyclosphosphamide) (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelarnine; acetogenins (especially bullatacin and bullatacinone); delta-9-tetrahydrocannabinol (dronabinol, MARENOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptoplhycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e.g., calicheamicin, especially calicheamicin gamma II and calicheamicin omega II (see, e.g., Angew, Chem. Intl. Ed. Engl., 33: 183-186 (1994)); dynemicin, including dynemicin A; an esperamicin; as well as neocarzino statin chromophore and related chromoprotein enediyne antibiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection) (DOXIL®, liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermaraium; tenuazonic acid; triaziquone; 2,2',2''-trichlorotriethylamine; trichothecenes (especially T-2 toxin, verracurin A, roridin A and anguidine); urethan; dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE), and docetaxel (TAXOTERE®); chloranbucil; 6-thioguanine; mercaptopurine; metliotrexate; platinum agents such as cisplatin, oxaliplatin, and carboplatin; vincas, which prevent tubulin polymerization from forming microtubules, including vinblastine (VELBAN®), vincristine (ONCOVIN®), vindesine (ELDISINE®), FILDESIN®), and vinorelbine (NAVELBINE®)); etoposide (VP-16); ifosfamide; mitoxantrone; leucovorin; novantrone; edatrexate; daunomycin; aminopterin; ibandronate; topoisomerase inhibitor RFS 2000; difluorometlhylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAJX®), pamidronate (AREDIA®), tiludronate (SKELID®), or risedronate (ACTONEL®) troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (Pfizer); perifosine, COX-2 inhibitor (e.g., celecoxib or etoricoxib), proteosome inhibitor (e.g., PS341); bortezomib (VELCADE®); CCI-779; tipifarnib (811577); orafenib, ABT510; Bcl-2 inhibitor such as oblimersen sodium (GENASENSE®); pixantrone; EGFR inhibitors (see definition below); tyrosine kinase inhibitors (see definition below); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment schedule with oxaliplatin (ELOXATIN) combined with 5-FU and leucovovin.

Also included in this definition are anti-hormonal agents that act to regulate or inhibit hormone action on tumors such as anti-estrogens with mixed agonist/antagonist profile, including, tamoxifen (NOLVADEX®), 4-hydroxytamoxifen, trioxifene, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and nonsteroidal aromatase inhibitors such as anastrazole (ARIMIDEX®), letrozole (FEMAR®) and aminoglutethimide, and other aromatase inhibitors including vorozole (RIVISOR®), megestrol acetate (MEGASE®), fadrozole, imidazole; lutenizing hormone-releasing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor downregulators (ERDs); anti-androgens such as flutamide, nilutamide and bicalutamide; testolactone; and pharmaceutically acceptable salts, acids or derivatives of any of the above; as well as combinations of two or more of the above.

Other therapeutic agents that can be used in combination with the anti-PD-L1 antibodies of the invention can be growth factor function inhibitors, for example, such inhibitors include growth factor antibodies and growth factor receptor antibodies (e.g., anti-erbB2 antibody trastuzumab [Herceptin], anti-EGFR antibody panitumumab, anti-erbB1 antibody cetuximab [Erbitux, C225] and any growth factor or growth factor receptor antibodies disclosed in Stern et al. Critical reviews in oncology/haematology, 2005, Vol. 54, pp 11-29); antiangiogenic agents, such as the inhibitory effects of vascular endothelial growth factor, [e.g., anti-vascular endothelial cell growth factor antibody bevacizumab (Avastin)], anti-vascular endothelial growth factor receptor antibodies such as anti-KDR antibodies and anti-flt1 antibodies; antisense therapies, for example directed to the above targets, such as ISIS 2503, anti-ras antisense agents or G3139 (Genasense), anti-bcl2 antisense agents; gene therapy approaches, including, for example, approaches with the replacement of aberrant genes such as aberrant p53 or aberrant BRCA1 or BRCA2, GDEPT (gene-directed enzyme prodrug therapy) approaches using cytosine deaminase, thymidine kinase or bacterial nitroreductase enzyme, and approaches aimed at increasing the patient's tolerance to chemotherapy or radiotherapy, such as multidrug resistance gene therapy; immunotherapeutic approaches, including, for example, the treatment with Alemtuzumab (campath-1H), a monoclonal antibody directed to CD52, or treatment with antibodies directed to CD22, ex vivo and in vivo approaches to increase the immunogenicity of tumor cells of the patient, transfection with cytokines such as interleukin 2, interleukin 4 or granulocyte-macrophage colony stimulating factor, approaches aimed at reducing T-cell anergy, such as treatment with monoclonal antibodies inhibiting CTLA-4, approaches using transfected immune cells such as cytokine-transfected dendritic cells, approaches using cytokine-transfected tumor cell lines and approaches using anti-idiotypic antibodies, adaptive transfer of T-cells using T-cells exposed to non-specific activation or targeted to a particular antigen of interest, ex vivo; protein degradation inhibitors such as a proteasome inhibitor such as Velcade (bortezomide); biotherapeutic therapeutic approaches, for example using peptides or proteins (such as antibodies or soluble constructs of external receptor domains) that sequester ligand receptors, block ligand binding to the receptor, or weaken receptor signaling (e.g., due to increased receptor degradation or reduced expression levels).

Doses and Routes of Administration

The anti-PD-L1 antibody of the present invention will be administered in an amount effective for treating the subject condition, i. e., in doses and for periods of time necessary to achieve the desired result. The therapeutically effective amount may vary depending on such factors as patient's certain condition to be treated, age, gender and weight, as well as whether the administration of the anti-PD-L1 antibodies is an individual treatment or it is carried out in combination with one or more additional anti-autoimmune or anti-inflammatory treatment methods.

Dosage schedule can be adjusted to provide the optimal desired response. For instance, one bolus may be administered, several separate doses may be administered over a period of time, or the dose may be proportionally decreased or increased depending on the acuteness of the therapeutic situation. Particularly useful is parenteral composition production in a unit dosage form for simplicity of the administration and dosing homogeneity. The unit dosage form as used herein relates to physically discrete units suitable as unit doses for patients/subjects to be treated; each unit comprises a predetermined quantity of an active compound calculated to produce the desired therapeutic effect in combination with the desired pharmaceutically carrier. Typically, the specification for the unit dosage forms of the present invention is defined and directly depends on (a) unique characteristics of the chemotherapeutic agent and particular therapeutic or prophylactic effect to be achieved, and (b) limitations intrinsic in compounding technique for such active compound for treating the susceptibility in subjects.

Thus, those skilled in the art would appreciate, based upon the disclosure provided herein, that doses and dosage schedule are adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Thus, although some doses and dosage schedules are provided herein by way of examples, these examples in no way limit doses and dosage schedules that may be required for a patient in practising the present invention.

It is noted that dosage values may vary, depending on the type and severity of the condition to be relieved, and may include one or more doses. In addition, it is to be understood that for any certain patient, certain dosage schedules should be adjusted over a time according to the individual needs and at the discretion of medical practitioner performing or controlling the administration of the compositions, and that the concentration ranges herein are provided by way of an example only and are not intended to be limiting the scope or practice of the claimed compositions. In addition, the dosage schedule with the compositions of the present invention may be based on different factors, including the type of the disease, age, weight, gender, patient health status, condition severity, route of administration and particular anti-PD-L1 antibody used. Thus, the dosage regimen may vary to a great extent but may be determined regularly using standard methods. For example, the doses may be adjusted based on pharmacokinetic and pharmacodynamic parameters that may include clinical effects, such as toxic effects or laboratory values. Thus, the present invention encompasses individual dose-escalation as determined by the skilled artisan. The determination of the required dose and regimens are well-known in the relevant art and would be appreciated by the skilled in the art upon the insight into the disclosed herein.

Examples of suitable routes of administration are provided above.

It is contemplated that a suitable dose of the anti-PD-L1 antibody of the invention would range from 0.1-200 mg/kg, preferably 0.1-100 mg/kg, including about 0.5-50 mg/kg, for example, about 1-20 mg/kg. The anti-PD-L1 antibody can be administered, for example, at a dose of at least 0.25 mg/kg, for example at least 0.5 mg/kg, including at least 1 mg/kg, for example at least 1.5 mg/kg, for example, as well as at least 2 mg/kg, for example at least 3 mg/kg, including at least 4 mg/kg, for example at least 5 mg/kg; and for example up to at most 50 mg/kg, including up to at most 30 mg/kg, for example up to at most 20 mg/kg, including up to at most 15 mg/kg. The administration will usually be repeated at suitable time intervals, e.g., once per week, once per two weeks, once per every three weeks or one per every four weeks, and as long as the physician judges it advisable, and, if necessary, the dose may be optionally increased or decreased by the physician.

Article (Products) and Kits

A further embodiment of the invention is an article that comprises products for the treatment of cancer, in particular, HNSCC, cancer of unknown primary, glioblastoma, oesophageal cancer, bladder cancer, TNBC, CRC, hepatocellular carcinoma, melanoma, NSCLC, kidney cancer, ovarian carcinoma, Hodgkin's lymphoma, CRC MSI. The product is a container and a label or package insert that is placed on or inserted into a container. Acceptable containers are, for example, tins, vials, syringes, etc. Containers can be made from various materials, such as glass or plastic. The container contains a composition effective for treating a particular condition and may have a sterile inlet channel (for example, the container can be an intravenous solution bag or a vial provided with a stopper that can be punctured with a needle for hypodermic injection). At least one active substance in the composition is an anti-PD-L1 antibody of the invention. The label or package insert indicates that the composition is used to treat a particular condition. The label or package insert should additionally contain the instructions for the administration of the antibody composition to a patient.

The package insert contains the usual instructions that include packages of therapeutic products offered for sale, including exemplary information about indications, use, dose, route of administration, contraindications and/or precautions regarding the use of such therapeutic products. In one embodiment of the invention, the package leaflet indicates that the composition is used for the treatment of cancer, in particular, HNSCC, cancer of unknown primary, glioblastoma, oesophageal cancer, bladder cancer, TNBC, CRC, hepatocellular carcinoma, melanoma, NSCLC, kidney cancer, ovarian carcinoma, Hodgkin's lymphoma, CRC MSI.

In addition, the article may further comprise a second container with a pharmaceutically acceptable buffer, such as bacteriostatic water for injection (BWI), phosphate buffered saline, Ringer's solution and dextrose solution. In addition, it may include other products required from the commercially and the user's point of view, in particular, other buffers, diluents, filters, needles and syringes.

The invention also relates to kits that can be used for various purposes, for example, for detecting PD-L1 in tissues, cells or fluids of a mammalian organism. Such kit would be suitable for screening associated with PD-L1 diseases. The kit includes a specific binding agent or the antibody of the invention and a means indicative of the reaction behaviour of the specific binding agent or the antibody with PD-L1 if present. In one embodiment, the antibody is a monoclonal antibody. In one embodiment, the PD-L1 binding antibody is labelled. In another embodiment, the antibody is an unlabelled primary antibody, and the kit further comprises primary antibody detection agents. In one embodiment, the detection agents comprise a labelled secondary antibody that is an anti-immunoglobulin. The antibody can be labelled with a marker selected from the group consisting of a fluorochrome, enzyme, radionuclide material and radiopacifier. The kit can be a kit that comprises antibodies for detecting and quantifying PD-L1 in vitro, for example, in ELISA or Western blotting. Also, as with the article, the kit comprises a container and a label or package insert placed on or inside the container. The container contains a composition that includes at least one anti-PD-L1 antibody according to the invention. Additional containers may contain, for example, diluents and buffers, control antibodies. The label or package insert may comprise a description of the composition and the instructions for its use in vitro or for diagnostic purposes.

Diagnostic Use and Composition

An anti-PD-L1 antibody of the present invention is also used in diagnostic processes (e.g., in vitro, ex vivo). For example, the anti-PD-L1 antibody may be used to detect or measure the level of PD-L1 in samples obtained from a patient (for example, a tissue sample or body fluid sample such as inflammatory exudate, blood, serum, bowel fluid, saliva or urine). Suitable detection and measurement techniques include immunological techniques such as flow cytometry, enzyme-linked immunosorbent assay (ELISA), chemiluminescence analysis, radioimmunoassay, and immunohistology. The invention further provides kits (e.g., diagnostic kits) comprising the anti-PD-L1 antibodies as described herein.

For the best understanding of the invention, the following Examples are provided. The following Examples are provided for illustrative purposes only and are not to be construed as limiting the scope of the present invention application in any way.

All publications, patents and patent applications cited in the specification are incorporated herein by reference. Although the foregoing invention has been described in some details by way of illustration and example for purposes of excluding of an ambiguous interpretation, those skilled in the art, based on the concepts disclosed herein, will clearly appreciate that certain alterations and modifications may be made without departing from the basic principles and the scope of the accompanying embodiments of the invention.

EXAMPLES

Example 1

Producing Recombinant Antigens and Antibodies in Suspension Mammal Cell Culture

Antibodies and antigens were produced in established cell line obtained from Chinese hamster ovary cells (CHO-K1) according to published protocols [Biotechnol Bioeng. 2005 Sep. 20; 91(6):670-677, Liao Metal., 2004; Biotechnol Lett. 2006 June; 28(11):843-848; Biotechnol Bioeng. 2003 Nov. 5; 84(3):332-342]. Cells constitutively expressing the gene of EBNA1 protein (Epstein-Barr virus nuclear antigen 1) were used. Suspension culture was conducted in flasks on an orbital shaker using serum-free media from Life Technologies Corporation and in accordance with manufacturer's guidelines. For transient expression, cells in a concentration of $2*10^6$/ml were transfected using linear polyethyleneimine (PEI MAX, Polysciences). DNA/PEI ratio was 1:3/1:10. In 5-7 days after transfection, cell culture was centrifuged at 2000 g for 20 min and filtered through 0.22 μm filter. Target proteins from culture liquid were isolated by affinity chromatography.

The recombinant PD-L1 protein containing EPEA-tag (glutamic acid-proline-glutamic acid-alanine) at the C-terminus of the protein was isolated and purified from the culture liquid using the CaptureSelect C-tag Affinity Matrix sorbent. The culture liquid was passed through a chromatography column pre-filled with 5 ml of C-tag sorbent, then the column was washed with 25 ml of PBS to wash out the non-specifically binding components. Bound antigen was eluted in soft conditions with 20 mM Tris, 2M $MgCl_2$, pH 7.0-7.4. Then the protein was dialyzed into PBS (pH 7.4) using semi-permeable dialysis membrane, filtered (0.22 μm), transferred into tubes and stored at −70° C.

Recombinant proteins PD-1 and PD-L1-Fc were isolated and purified from culture fluid using Protein A affine HPLC column. Cleared culture liquid was passed through 5 ml HiTrap rProtein A Sepharose FF column (GE Healthcare) equilibrated with phosphate-buffered saline (PBS, pH 7.4). Then the column was washed with 5 volumes of PBS to remove non-specifically bounding components. Bound antigen was eluted with 0.1M glycine buffer pH 3. The major protein elution peak was collected and brought to neutral pH with 1M Tris buffer (pH 8). All stages were conducted at a flow rate of 110 cm/h. Then isolated protein was dialyzed into PBS (pH 7.4) using semi-permeable dialysis membrane, filtered (0.22 μm), transferred into tubes and stored at −70° C.

Figure 4A:
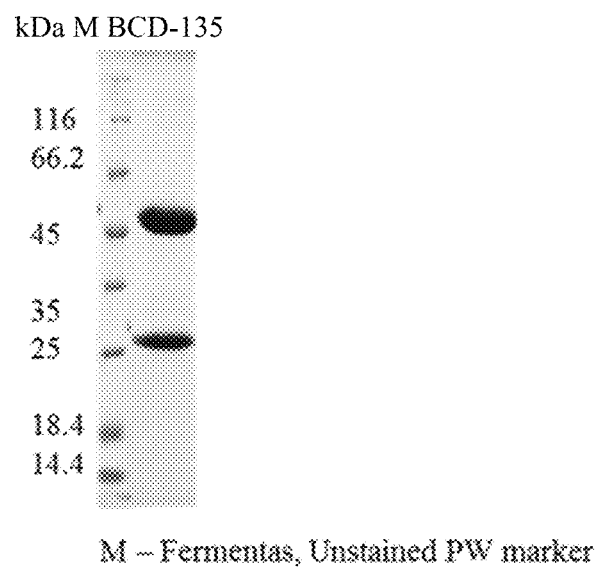
FIG. 4. BCD-135 electrophoregram under reducing conditions (4A, 12% SDS-PAGE), under non-reducing conditions (4B, 8% SDS-PAGE).
Figure 4B:
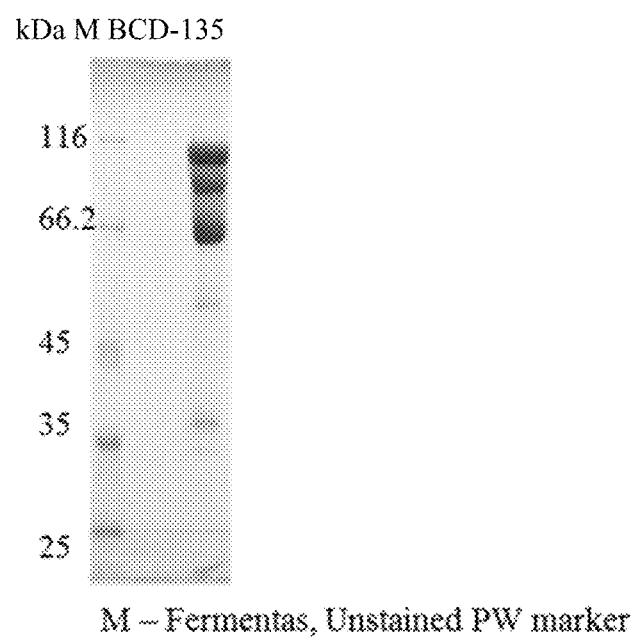

IgG1 antibodies were purified on 1 ml Hi Trap rProteinA FF column (GE Healthcare) in accordance with the procedure above for antigens. The purity of the protein solution obtained was evaluated by SDS-PAGE (FIGS. 4A and 4B).

Example 2

Creation of Naive Human Antibody Fab Library MeganLib™

Total B-lymphocyte RNA from blood samples collected from more than thousand human donors was isolated using RNeasy Mini Kit in accordance with the provided protocol (QIAGEN). RNA concentration assay was performed using Nanovue kit (GE Healthcare) and the quality of isolated RNA was tested by 1.5% agarose gel electrophoresis.

Reverse transcription reaction was carried out using the MMLV RT kit (from Evrogen) according to the recommended protocol using MMuLV reverse transcriptase and random-hexamer oligonucleotides as a primer.

Reverse transcription products were used as a template in a two-stage polymerase chain reaction to produce variable domain genes flanked by restriction sites using the oligonucleotide set following the author protocols [J Biol Chem. 1999 Jun. 25; 274(26): 18218-30].

Figure 2:
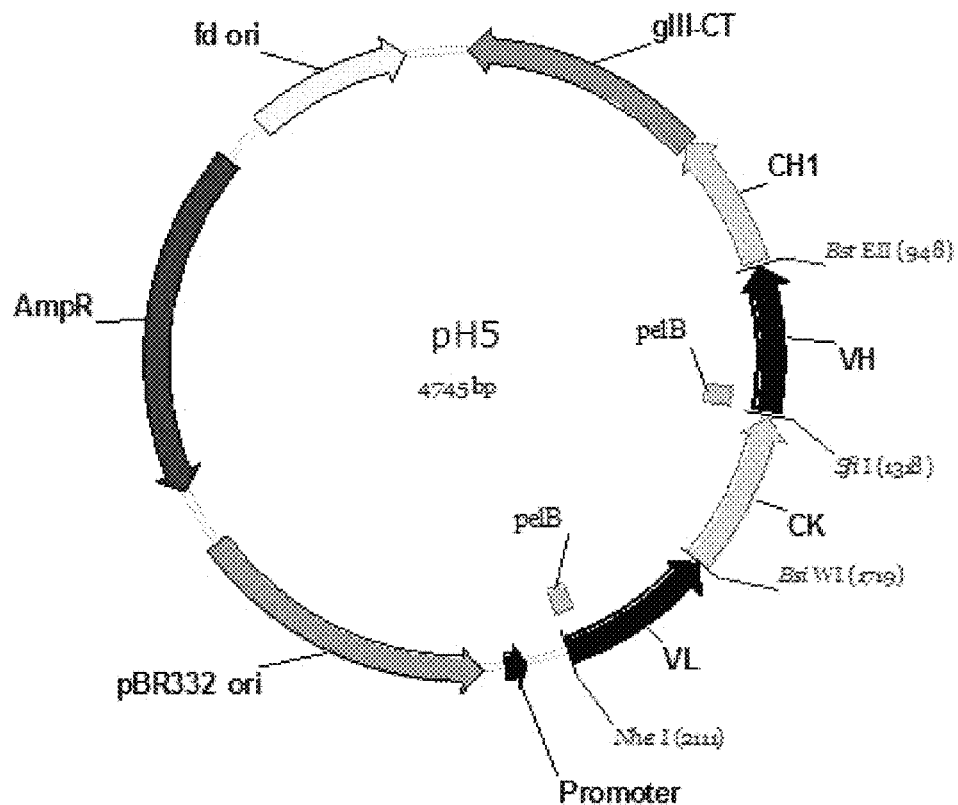
FIG. 2. Map of the phagemid for the Fab phage display library cloning.

Obtained DNA preparation VL-CK-VH (FIG. 1) was treated with restriction enzymes NheI/Eco91I and ligated into an original phagemid pH5 (FIG. 2). Ligation products were transformed into electrocompetent SS320 cells prepared according to protocols described in [Methods Enzymol. 2000; 328: 333-63.]. The repertoire of the combinatorial phage Fab-display library MeganLib™ was $10^{11}$ transformants. Phage preparations from Fab-libraries were prepared according to the procedure described above [J Mol Biol. 1991 Dec. 5; 222(3): 581-97].

Example 3

Selection of Phage Antibody Fab Libraries

Specific phage human anti-PD-L1 Fab-antibodies were obtained from the combinatorial phage Fab-display library MeganLib™. The selection was performed on human PD-L1 by phage display method [Nat Biotechnol. 1996 March; 14(3):309-14; J Mol Biol. 1991 Dec. 5; 222(3): 581-97], but with the use of magnetic particles and the KingFisher Flex instrument, since the use of this technique allows up to 96 different schemes and variants of biopanning to be carried out in parallel.

Figure 3:
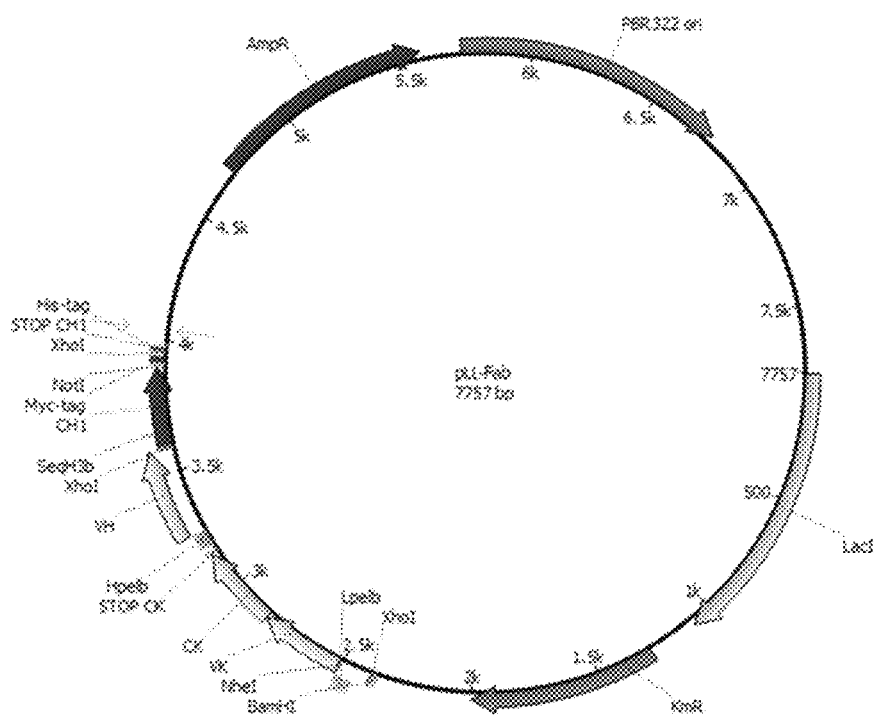
FIG. 3. Map of the expression plasmid for the Fab producing.

In biopanning selection, biotinylated PD-L1-Fc at a concentration of 10 µg/ml was immobilized on the surface of streptavidin magnetic particles by incubating the protein with particles for 1 hour at room temperature on a rotator. The particles were then washed with PBS (pH 7.4), then the particles were blocked with 2% skim milk solution on PBS (pH 7.4) for 1 hour. Then, the phage solution in PBS (pH 7.4) with 2% skim milk was added to antigen-bound magnetic particles, the concentration of phage particles was $2.5*10^{12}$ per ml. The mixture was incubated for 40 minutes while stirring. Unbound phages were removed during several washings of magnetic particles with PBS solution (pH 7.4) with 0.1% Tween 20. The number of washings was increased from round to round (10 on the $1^{st}$ round, 20 on the $2^{nd}$ round and 30 on the $3^d$ round). Phages that remained bound with the antigen on the surface of magnetic particles were eluted from the particles with 100 mM Gly-HCl solution (pH 2.2) during 15 min under stirring and then neutralized with 1 M TRIS-HCl (pH 7.6). *E. coli* TG1 bacteria were infected with phages obtained; phages were produced therein and isolated and used in the next selection round. After two to three rounds, DNAs (phagemids) were isolated from the phages, and the antibody variable domain genes were cloned into expression vectors (FIG. 3) for the production of Fab in *E. coli* cells.

Example 4

Fab Screening of Specifically Binding Human PD-L1

ELISA was used to search for Fab binding to human PD-L1. As a positive control, Fab with the published sequence Atezolizumab (Genentech) was used. For the specific binding assay, ELISA plate wells (medium binding from Greiner bio one) were coated with 50 µl of PD-L1-FE (0.2 µg/ml in 1× carbonate buffer), hermetically sealed and incubated overnight at 4° C. All subsequent steps were carried out according to the standard ELISA protocol using a high-throughput automated platform based on the GenetixQ-Qpix2xt (from Molecular Device) and Tecan Freedom EVO 200 (from Tecan) robotic systems. To block a non-specific binding, a blocking buffer BB (200 µL of 0.5% skimmed milk in PBS) was added. The plates were incubated on a shaker for an hour at room temperature. After washing with PBS-Tween, 50 µl per well of the test cell supernatant containing the test Fab mixed with an equal volume of BB was added. The plates were again incubated, shaking for one hour at room temperature, followed by washing for three times each plate well with PBS-Twin buffer. Once washed, (50 µL/well) anti-human Fab HRP-conjugated secondary antibodies (from Pierce-ThermoScientific) were added at 1:5000 ratio in PBS-Tween. The plates were shaken on a rotary shaker (50 min, room temperature) and washed for three times with FSB-Twin buffer, as described above. The colourimetric signal was developed by adding TMB (50 µL/well) until saturation (average 3-5 min), then the development was quenched by adding stop solution (30 µL/well, 10% sulphuric acid). Colour signal was measured at a wavelength of 450 nm using a suitable Tecan-Sunrise plate reader (from Tecan). Antibody binding level was proportional to producing the colour signal. Clones having the colour signal greater than the signal from the control antibody were tested in ELISA for non-specific binding.

Example 5

Analysis of Selected Fab Non-Specific Binding with Other Antigens

ELISA is used to measure the non-specific binding of studied Fab-fragments with other antigens. The study was performed as described above, but IL6R-Fc, INFα2b, PCSK9-VG-FE, PD-1-Fc (2.5 µg/ml in 1× carbonate buffer) were used as antigens for immobilization. PD-L1-Fc (0.2 µg/ml in 1× carbonate buffer) was used as a control for specific binding. All further stages were conducted in accordance with the standard ELISA protocols using a high-throughput automated platform based on the GenetixQ-Qpix2xt (from Molecular Device) and Tecan Freedom EVO 200 (from Tecan) robotic systems. Clones having the colour signal of non-specific binding not greater than the signal from the specific binding were tested in a competitive ELISA assay to identify antagonist Fabs blocking the interaction between the ligand and the receptor.

Example 6

Competitive ELISA of Blocking Interaction Between PD-L1 and its PD-1 Receptor

Competitive ELISA was used to test preselected anti-human PD-L1 specific Fabs for the ability to block interaction with the PD-receptor. As a positive control antagonist, Fab with the published sequence Atezolizumab (Genentech) was used.

PD-1-Fc was immobilized in ELISA plate wells (medium binding from Greiner bio one) at 50 µl with the concentration of 1 µg/ml in 1× carbonate buffer and incubated overnight at 4° C. All subsequent steps were carried out according to the standard ELISA protocols using a high-throughput automated platform based on the GenetixQ-Qpix2xt (from Molecular Device) and Tecan Freedom EVO 200 (from Tecan) robotic systems. To block a non-specific binding, a blocking buffer BB (200 µL of 0.5% skimmed milk in PBS) was added. The plates were incubated on a shaker for an hour at room temperature.

In parallel, the cell supernatant containing the test Fab and PD-L1-Fc (at a final concentration of 2 µg/ml in PBS-Twin) were mixed at 1:1 ratio in the non-absorbent plates, incubated for 45 minutes at room temperature and shaking at 500 rpm.

After BB washing from the plate containing the PD-1 receptor, a mixture of Fab and PD-L1 was added therein, incubated for 45 minutes at room temperature and shaking at 500 rpm. After that, each plate well was washed for three times with PBS-Twin buffer, 50 μl/well of anti-human Fab HRP-conjugated secondary antibodies (from Pierce-ThermoScientific) were added at 1:5000 ratio in PBS-Tween. They were incubated for 45 minutes at room temperature and shaking at 500 rpm, followed by each plate well was washed for three times with PBS-Twin buffer, as described above. The colourimetric signal was developed by adding TMB (50 μL/well) until saturation (average 3-5 min), then the development was quenched by adding stop solution (30 μL/well, 10% sulphuric acid). Colour signal was measured at a wavelength of 450 nm using a suitable Tecan-Sunrise plate reader (from Tecan). Fab binding level was inversely proportional to producing the colour signal. Clones showed blocking at the level of control Fab antibody Atezolizumab were recorded as positive and used for further analysis. Variable domain genes from positive clones were sequenced according to standard protocols on an Applied Biosystems 3130 Genetic Analyzer instrument (Applied Biosystems) and analyzed.

Example 7

Comparative Screening of Human Anti-PD-L1 Fab Candidates Based on Koff

Koff-screening was performed using a Pall Forte Bio Octet Red 96 instrument. Anti-FABCH1-biosensors (SA) were rehydrated for 30 minutes in the reaction buffer containing 10 mM PBS, pH 7.2-7.4, 0.1% Tween-20, 0.1% BSA. The reaction buffer was added into study $E.\ coli$ supernatant samples to a final concentration of 1×. Then, anti-FABCH1-biosensors were submerged in $E.\ coli$ supernatants containing Fab fragments of candidate antibodies for 12 hours at 4° C. Sensors with surface immobilized Fab fragments were transferred into wells with reaction buffer wherein baseline was recorded (for 60 seconds). Next, sensors were transferred to wells with analyte solution (PD-L1, 30 μg/mL) to associate antigen-antibody complex (300 s). Then, sensors were returned to the wells containing the reaction buffer for the next dissociation step (600 s). After each experiment, used sensors were regenerated by 3-time placing them into the regeneration buffer (Gly-HCl, pH 1.7), thereafter they were used in the next experiment. Obtained curve analysis was carried out using Octet Data Analysis (ver 7.0) software according to the standard procedure using 1:1 interaction model.

Example 8

Figure 5:
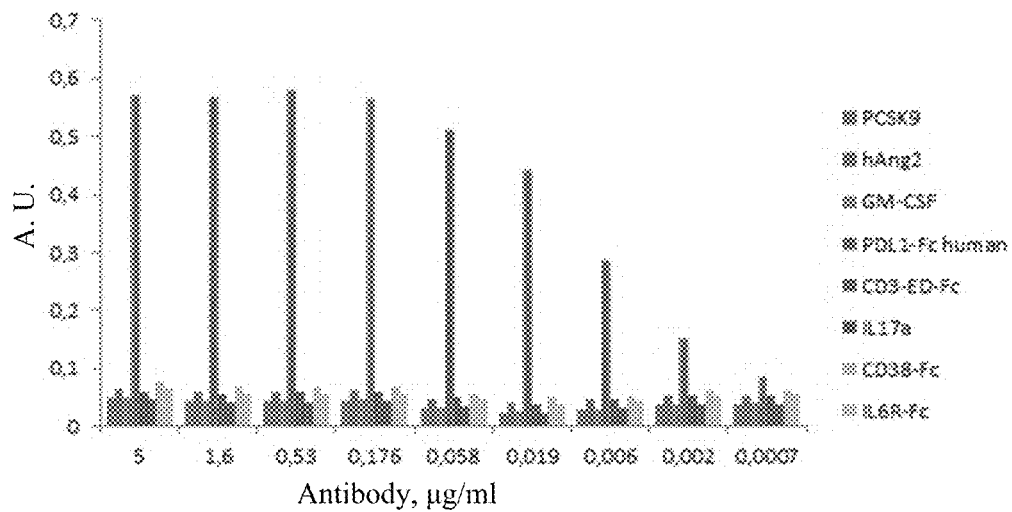
FIG. 5. Enzyme-linked immunosorbent assay of BCD-135 interaction with PD-L1, and other antigens.

Enzyme Immunoassay of Anti-PD-L1 Antibody Interaction with PD-L1 and Other Antigens ELISA was used to measure the relative affinity of anti-PD-L1 antibodies and other antigens. For binding assay, ELISA plate wells (medium binding from Greiner bio one) were coated with 50 μl of PD-L1-Fc, fPCSK9-EPEA, Ang2-H6F, GM-CSF-FE, CD3-ED-Fc, IL17a, CD38-Fc, IL6R-Fc (1 μg/ml in 1× carbonate buffer), hermetically sealed and incubated overnight at 4° C. All the subsequent stages were conducted following standard ELISA protocol. To block a non-specific binding, a buffer BB (200 μL of 0.5% skimmed milk in PBS) was added. The plates were incubated on a shaker for an hour at room temperature. Once washed with PBS-Tween, 50 μl per well of the test BCD-135 antibody at a concentration of 5 μg/ml in PBS-Twin was added. The plates were again incubated, shaking for one hour at room temperature, followed by washing for three times each plate well with PBS-Twin buffer. Once washed, (50 μL/well) anti-human Fab HRP-conjugated secondary antibodies (from Pierce-ThermoScientific) were added at 1:5000 ratio in PBS-Tween. The plates were shaken on a rotary shaker (50 min, room temperature) and washed for three times with FSB-Twin buffer, as described above. The colourimetric signal was developed by adding TMB (50 μL/well) until saturation (average 3-5 min), then the development was quenched by adding stop solution (30 μL/well, 10% sulphuric acid). Colour signal was measured at a wavelength of 450 nm using a suitable Tecan-Sunrise plate reader (from Tecan). Antibody binding ratio was proportional to producing the colour signal (FIG. 5). The anti-PD-L1 antibody specifically binds to PD-L1 and is not bound to other antigens studied.

Example 9

NFAT Signaling Reactivation with Anti-PD-L1 Antibodies in Jurkat-NFAT-PD-1 Reporter Cell Line An engineering of the human T-cell derived line Jurkat was performed by introducing into its genome two genetic constructs. One construct encoded the human PD-1 receptor gene. The other construct encoded the luciferase gene under the control of NFAT-sensitive genetic element. As a result, a Jurkat-NFAT-PD-1 reporter cell line was obtained that expressed PD-1 receptor on the surface membrane and contained NFAT-dependent promoter that directed luciferase gene transcription. The synthesis of luciferase enzyme in the cells of this line is proportional to the level of NFAT activity that, in turn, reflects the overall level of T-lymphocyte activation.

The activity of anti-PD-L1 antibodies was analyzed using this cell line as follows: activation of TCR receptors by anti-CD3 and anti-CD28 antibodies triggered the intracellular cascade leading to the NFAT promoter activation. PD-L1 is presented on the surface of MDA-MB-231 cells activated by interferon. The interaction between PD-L1 and PD-1 inhibited signalling from TCR receptors to NFAT promoter. Anti-PD-L1 antibodies disconnected the interaction of PD-L1-PD-1, and the intracellular signalling was reactivated.

MDA-MB-231 cells were activated for the PD-L1 production with an interferon-gamma solution, for this purpose, 72 hours prior to the assay, interferon gamma was added to the cell suspension to a concentration of 20 ng/ml, then cells were plated in 96-well culture plates at a rate of 10,000 cells/well.

After 72 hours of activation, the growth medium from the plates with MDA-MB-231 cells was removed and dilutions of the analyzed antibodies, control antibody and isotype control in the cell growth medium from 10 μg/ml to 0.001 μg/ml were added, incubated for 30 minutes at room temperature.

Further, a suspension of Jurkat-NFAT-PD-1 cells and a solution of the activating antibodies aCD3/aCD28/a-mouseIgG were added to each well. The plate was placed in a $CO_2$ incubator for 6 hours.

Figure 6:
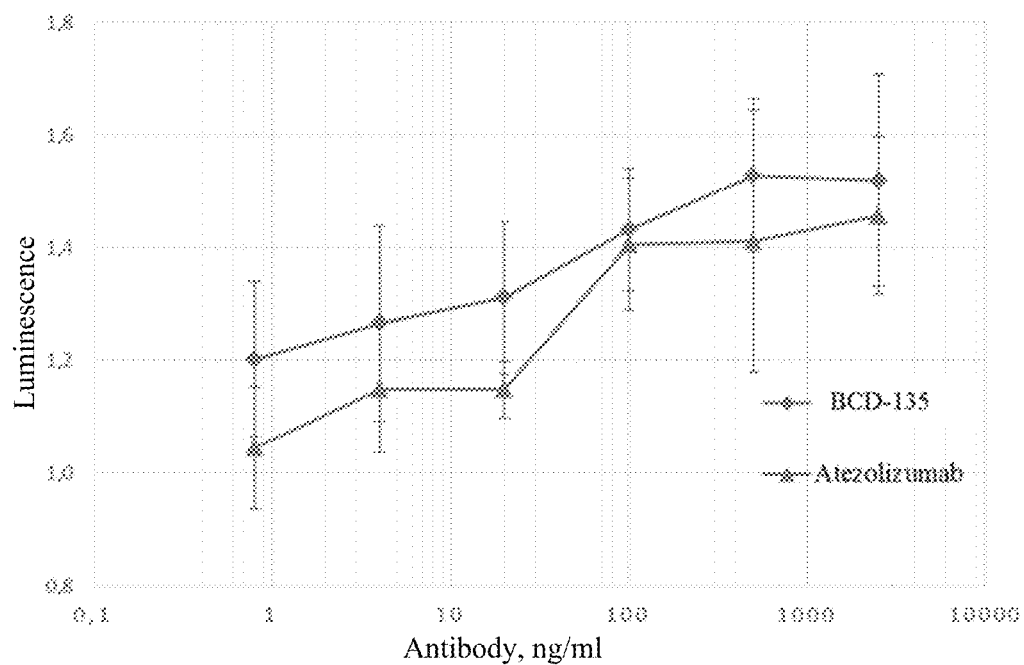
FIG. 6. NFAT signalling reactivation with anti-PD-L1 antibodies in Jurkat-NFAT-PD-1 reporter cell line.

A pre-prepared substrate for the luciferase Bio-Glo Luciferase assay system (Promega) was added to V cells/V substrate. The luminescence level was measured on Fluoroscan Ascent (FIG. 6). Anti-PD-L1 antibodies reactivated the luminescence level in the Jurkat-PD-1-NFAT reporter line.

Example 10

Assay of Anti-PD-L1 Antibody Interactions with FcRn and Fcγ-Receptors Using Octet RED 96

To assay the antibody interactions with FcgRIIIaV, FcgRIa, FcRn receptors, the Fortebio Octet RED96 instrument was used. C-terminal biotinylated receptors and streptavidin-coated biosensors (SA-Streptavidin) were used.

Biotinylated receptors were immobilized on the surface of the sensors. Further, the association stage was carried out: the sensors with the bound antigen were submerged into the antibody solutions with different concentrations (a series of antibody dilutions in a working buffer was prepared in advance and placed into the appropriate wells of a 96-well plate). After this, the dissociation stage was carried out: the sensors from the antibody solution were transferred to wells with the working buffer.

To assay the antibody affinity constants to FcgRIIIaV, and FcgRIa, phosphate buffer PH7.4 was used, for FcRn, phosphate buffer PH6.0 was used.

Figures 7, 8, 9:
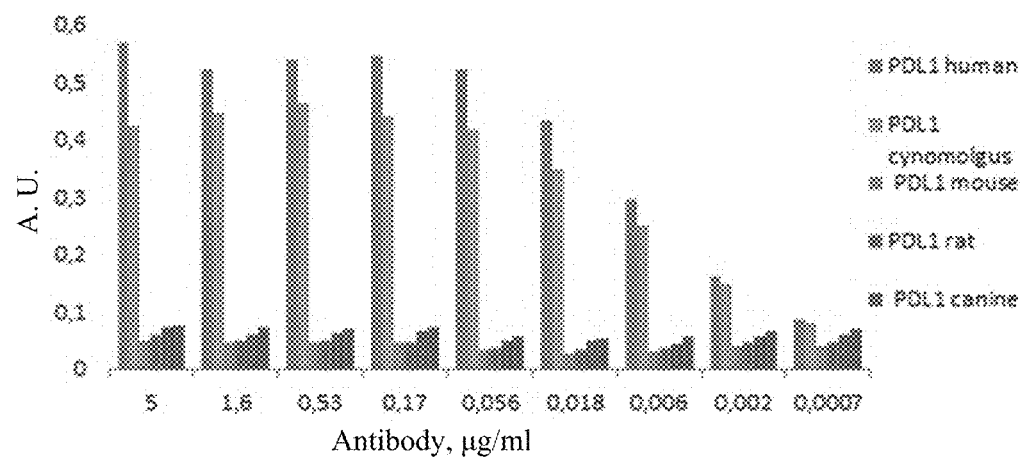
FIG. 7. Analysis of BCD-135 interactions with FcRn, and Fcγ-receptors on an Octet RED 96 instrument.
FIG. 8. Immunoenzymatic analysis of BCD-135 interactions with PD-L1 from different species.
FIG. 9. Analysis of BCD-135 interactions with human and cynomolgus monkey PD-L1 on an Octet RED 96 instrument.

Obtained curve analysis was carried out using the Forte Bio Data Analysis 8.2 software and the 1:1 binding model. The results are shown in FIG. 7. The binding to the Fcg receptors of the modified IgG1 antibody was not detected compared to the wild-type variant that suggested the absence of effector functions in the analyzed antibody. The affinity constant for the FcRn in the analyzed anti-PD-L1 antibody was 1.69E-08 1/M.

Example 11

Enzyme-Linked Immunosorbent Assay of Interactions Between Anti-PD-L1 Antibody and PD-L1 from Different Organisms ELISA was used to measure the relative affinity of anti-PD-L1 antibodies from different organisms. For the binding assay, ELISA plate wells (medium binding from Greiner bio one) were coated with 50 µl of human, cynomolgus, murine, rat, canine, rabbity PD-L1-Fc, (0.5 µg/ml in 1× carbonate buffer), hermetically sealed and incubated overnight at 4° C. All the subsequent stages were conducted following standard ELISA protocol described above. The anti-PD-L1 antibody specifically binds to human and cynomolgus PD-L1 and is not bound to other receptors studied (FIG. 8).

Example 12

Analysis of Anti-PD-L1 Antibody Interactions with Human and Cynomolgus Monkey PD-L1 on Octet RED 96 Instrument Constants of the antibody binding affinity to human and cynomolgus PD-L1 were measured with an OctetRed 96 instrument (from ForteBio). BCD-135 antibody at a concentration of 30 µg/ml was non-specifically immobilized onto the surface of the second-generation amino-reactive biosensors (ForteBio, AR2G) following the standard protocol according to the manufacturer instructions for AR2G sensors preparation and immobilization. The assay was carried out at 30° C. using PBS containing 0.1% Tween-20 and 0.1% BSA as a reaction buffer. The binding of human and monkey PD-L1 solutions to a sensor-bound antibody was analysed in a work buffer with an antigen concentration of 10 µg/ml to 1 µg/ml.

The binding curves minus the reference signal were analyzed using Octet Data Analysis (ver 8.2) software according to the standard procedure using the 1:1 interaction model. The anti-PD-L1 antibody specifically and affinely binds to the human and cynomolgus PD-L1 antigen (FIG. 9) with constants <1.0E-12 and 5.55E-10 1\M, respectively.

Example 13

Anti-PD-L1 Antibody Stability Determination

Figure 10:
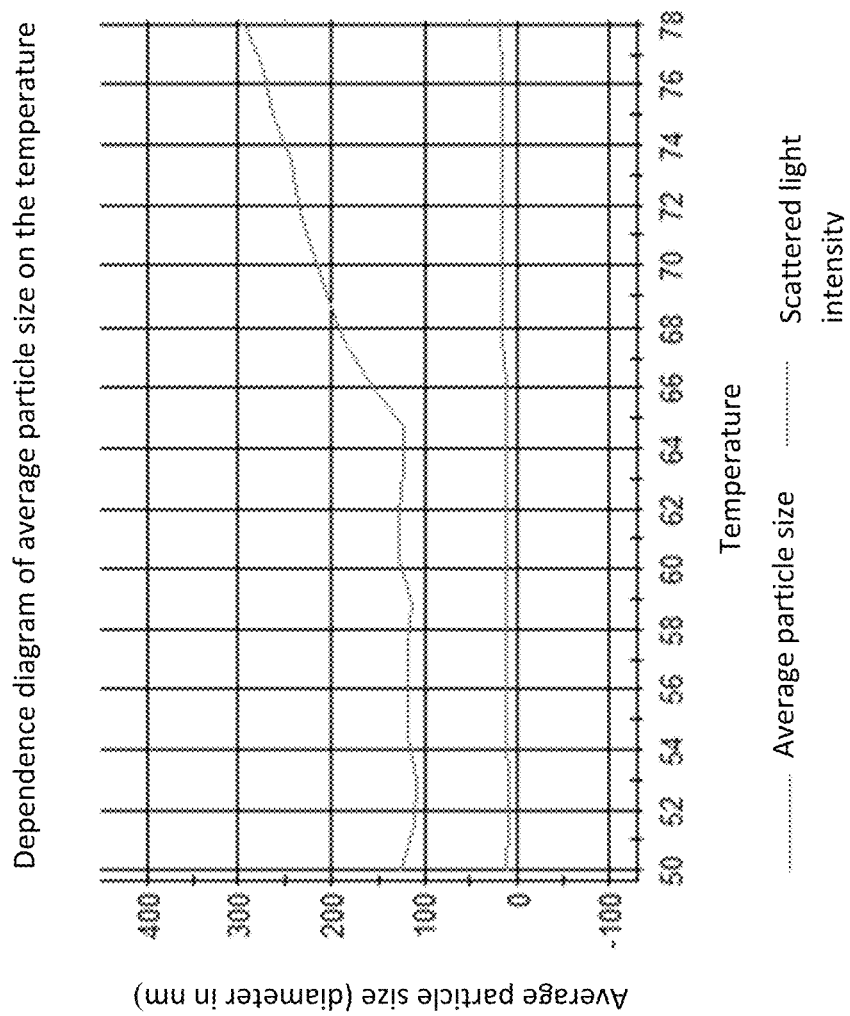
FIG. 10. Conformational stability analysis of BCD-135.

The conformational stability of BCD-135 was evaluated based on protein aggregation point using Dynamic Light Scattering technique (DLS). Protein aggregation point determination for study proteins (1 mg/ml) was performed using a Zetasizer Nano ZSP instrument. For this purpose, 0.5 ml of the solution was placed into a dust-free quartz cuvette that was heated gradually in an instrument from 50° C. to 90° C. while constant measuring the scattered light intensity. The BCD-135 antibody exhibited high conformational stability in 20 mM acetate buffer, a melting point of more than 80° C. (FIG. 10).

Figure 11:
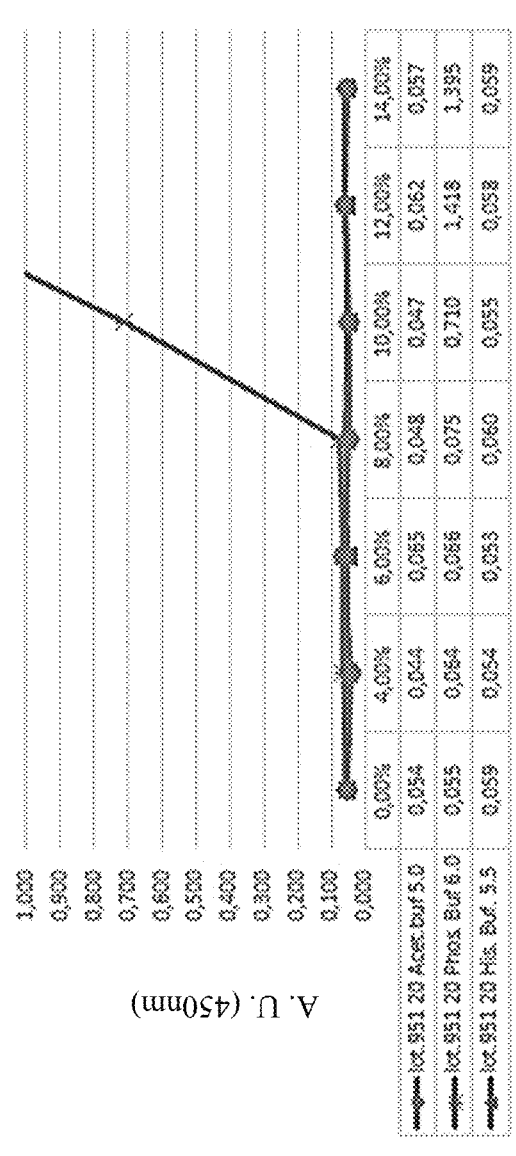
FIG. 11. Colloidal stability analysis of BCD-135.

The colloid stability of the candidates was evaluated by the PEG-protein aggregation method. For the experiment, samples with a protein concentration of 5 mg/ml were used. To UV spectrophotometry plates, the calculated amount of the sample, placebo solution, and PEG 6000 solution was added. All solutions in the wells were well mixed by pipetting. Further, the solution degree of turbidity was assessed visually, and the solution optical density at $\lambda=320$ nm was also measured. The BCD-135 antibody demonstrated a high colloidal stability (FIG. 11).

Figure 12A:
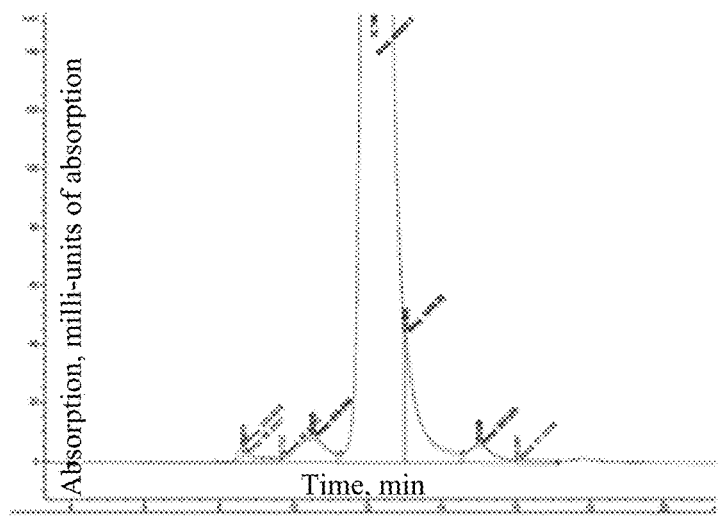
FIG. 12. Thermal stability analysis of BCD-135 in phosphate (A), acetate (B), and histidine (B) buffers. The x-axis represents time, Y-axis represents absorption.
Figure 12B:
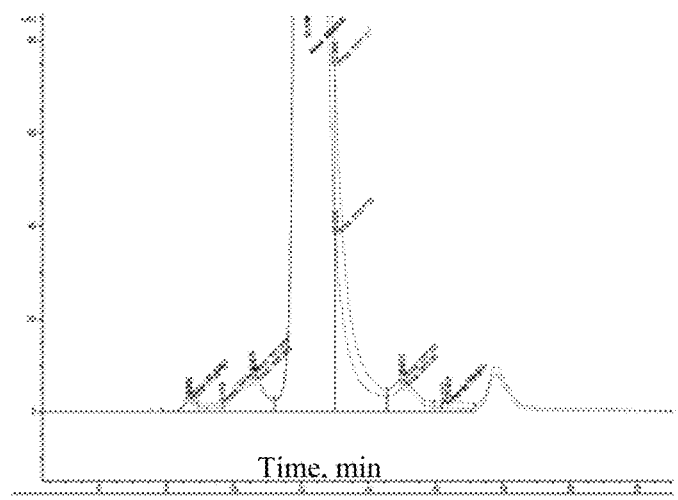
Figure 12C:
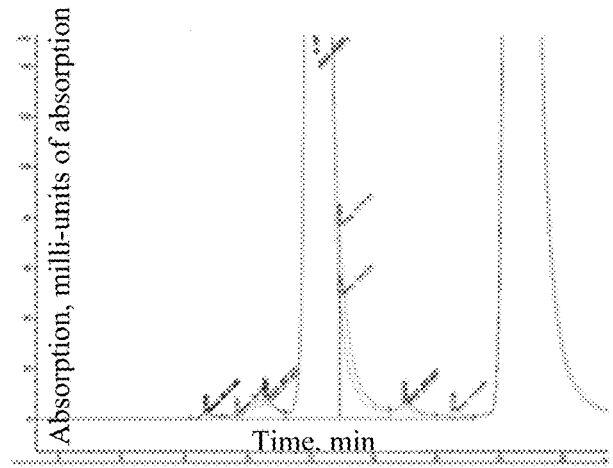

The antibody thermal stability was evaluated by thermal stress at 50° C. for 48 hours in three different buffers: 20 mM phosphate buffer at pH 6.0 (FIG. 12A), 20 mM acetate buffer at pH 5.0 (FIG. 12B) and 20 mM histidine buffer pH 5.5 (FIG. 12C). Homogeneity control was carried out by the HPLC method (SEC HPLC).

| Name | Test Buffers | Content change of the main peak for 48 h |
|---|---|---|
| BCD-135 | 20 mM phosphate buffer pH 6.0 | $\Delta = -0.126\%$ |
| BCD-135 | 20 mM acetate buffer pH 5.0 | $\Delta = -2.04\%$ |
| BCD-135 | 20 mM histidine buffer pH 5.5 | $\Delta = -1.55\%$ |

The test samples art the protein concentration of ~5 mg/ml were divided into 2 parts and placed in separate tubes: 1 tube for each formulation was stored in a refrigerator at 4° C., the rest were placed in a thermostat and incubated at 50° C. for 72 hours. Once the warm-up was finished, the tubes were removed from the thermostat and transferred for analysis (in FIGS. 12A, 12B and 12C, red indicates control kept at +4, blue indicates a sample after thermal stress). Anti-PD-L1 antibody showed high thermal stability in all three buffers (the difference between the content of aggregates in the solution before and after the thermal stress was not more than 5%):

The stability of BCD-135 in normal human serum was also assessed for 7 days at 37° C. For this purpose, recombinant PDL1 (100 µl, 2.5 µg/ml in 1× carbonate buffer) was added into wells of a 96-well high sorption ELISA plate. It was incubated at 4° C. for 18 hours. Further, the contents of the wells were removed and a blocking buffer (200 µl of 0.5% skimmed milk in TBST) was added. The plates were incubated at 37° C. for 30 minutes, then washed for 2 times with TBST solution.

To plot a calibration curve, 100 µl of solutions containing BCD-135 at a concentration of 0; 7.8; 15.6; 31.25; 62.5;

125.0; 250.0 ng/ml diluted in the blocking buffer was added to the wells of the first vertical row.

The plates were incubated for 30 minutes at 37° C., then the plates were washed for 3 times with TBST solution. Further, 100 µl solution of anti-human IgG Fc fragment goat polyclonal antibody conjugated with horseradish peroxidase was added to each well. The plates were incubated for 30 minutes at 37° C. Then the plates were washed for 4-5 times with TBST solution. To the washed and dried wells, 100 µl of TMB solution was added to develop the colour. The plates were placed in a place protected from light and incubated at a temperature of 22° C. for 20 to 25 minutes for the colour development. The reaction was quenched by adding to the wells 50 µl stop solution of 0.9 M sulfuric acid. The solution optical density in the wells was measured on a microplate reader at a wavelength of 450 nm.

Figures 13A, 13B:
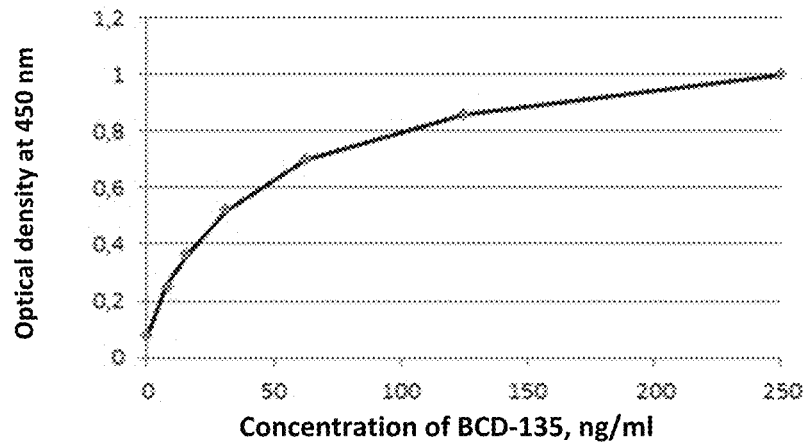
FIG. 13. Stability analysis of BCD-135 in human serum. A is a calibration curve representing the optical density dependence on the concentration of BCD-135 added to the well. B is the summary table showing the dependence of the BCD-135 concentration when incubated in human serum on the incubation time.

Based on the obtained data, a calibration curve was plotted (FIG. 13A) representing the optical density dependence on the concentration of BCD-135 added to the well. To plot the curve, the solution optical density arithmetical average was used. On the basis of the calibration curve, the BCD-135 concentration value in the sample was found corresponding to the values of the optical density obtained in the experiment.

Based on the study results, after 7 days of storage at 37° C. in human serum, the BCD-135 concentration determined was not different significantly from the concentration determined in serum samples prepared immediately before analysis (FIG. 13B) indicating the stability of the antibody.

Example 14

Constructing Library of BCD-135 Mutant Antibodies Specific for PD-L1.

To construct the BCD-135 mutant antibodies specific for PD-L1, a 3D modelling based structural analysis was carried out using YLab software package from BIOCAD and the PD-L1 model (PDB 4ZQK, PDB 4Z18) (see also Example 18). Based on the computational models, libraries of BCD-135 genes with partially degenerated codons (FUH G ET AL.), Improving antibody binding affinity and specificity for therapeutic development, Methods Mol Biol., 2009, 525, 353-376) were synthesized at positions in first and third CDR regions of the heavy chain variable domain of SEQ ID NO: 4 and in third CDR of the light chain variable domain of SEQ ID NO: 8. The resulting DNA of the randomized gene was cloned into a phage display plasmid pH5 (FIG. 2), according to the protocol described in Example 2. The transformation of these constructs into the SS320 strain yielded 5*10e7 independent transformants for the library according to the procedure [Methods Enzymol. 2000; 328: 333-63]. Phage preparations of mutant VH BCD-135 libraries were prepared according to the previously described procedure [Mol Biol. 1991 Dec. 5; 222(3): 581-97].

The selections of the obtained phage mutant BCD-135 Fab libraries were performed under conditions similar to those described above (Example 3).

Following the third round of the selection of the libraries described above on human recombinant PD-L1 product, performed ELISA assay of polyclonal phage products revealed significant enrichment and more than 10-fold excess above the non-specific binding background. Gene pools from enriched phage libraries of BCD-135 mutant Fab antibodies specific for human PD-L1-Fc were recloned into expression plasmid pLL (FIG. 3) containing myc-tag peptide at the C-terminus for ELISA detection.

Example 15

Comparative ELISA Assay of BCD-135 Mutant Fab Antibodies Specific for PD-L1.

ELISA is used to measure the tested mutant Fab antibody binding to human PD-L1, similar to as described in Example 4. The number of tested clones, producers of BCD-135 mutant Fab antibodies, was 400 units. A wild type of BCD-135 Fab antibody with the sequence of SEQ ID NO: 4 and SEQ ID NO: 8 was used as a positive control.

As a result, 85 positive clones giving the signal higher or similar to the control wild BCD-135 Fab antibody were selected (values in the range of 0.7-1.2 rel. units).

Example 16

Characterization of BCD-135 Mutant Fab Antibodies Specific Against PD-L1

Eighty-five ELISA screening (Example 15) positive clone candidates giving the signal higher or similar to the control wild BCD-135 Fab antibody were sequenced on the Applied Biosystems 3130 sequencer according to the protocols recommended by the manufacturer. As a result, 25 sequence-unique clones were obtained. The eight mutant Fab antibodies of the unique clones were further analysed by quantifying the kinetic dissociation constant on the Octet Red 96 instrument according to Example 7.

Koff-screening was performed using a Pall Forte Bio Octet Red 96 instrument, similar to that indicated in Example 7. Anti-FABCH1-biosensors (SA) were rehydrated for 30 minutes in the reaction buffer containing 10 mM PBS, pH 7.2-7.4, 0.1% Tween-20, 0.1% BSA. The reaction buffer was added into study E. coli supernatant samples to a final concentration of 1×. Then, anti-FABCH1-biosensors were submerged in E. coli supernatants containing Fab fragments of candidate antibodies for 12 hours at 4° C. Sensors with surface immobilized Fab fragments were transferred into wells with reaction buffer wherein baseline was recorded (for 60 seconds). Next, sensors were transferred to wells with analyte solution (PD-L1, 30 µg/mL) to associate antigen-antibody complex (300 s). Then, sensors were returned to the wells containing the reaction buffer for the next dissociation step (600 s). After each experiment, used sensors were regenerated by 3-time placing them into the regeneration buffer (Gly-HCl, pH 1.7), thereafter they were used in the next experiment. Obtained curve analysis was carried out using Octet Data Analysis (ver 7.0) software according to the standard procedure using 1:1 interaction model.

As a result, the kinetic dissociation constants of the mutant Fab antibodies were obtained, which showed comparable characteristics with the wild type of BCD-135 Fab, and thus a tolerance of up to 8% of the substitutions for three CDRs in the variable domains.

```
Anti-PDL1 VH of BCD-135
BCD-135 VH
         10        20        30        40        50        60        70        80
90        100       110       120
12345672901234567890123456789012345678901234567890123456789012345678901234567890123456
789012345678901234567890123456789012
EVQLVESGGGVVRPGGSLRLSCAASGFTFDDYAMSWVRQAPGKGLEWVSDISWSGSNTNYADSVKGRFTISRDNAKNSLYLQMNSL

RAEDTALYHCARAPLLAMTFGVGSWGQGTLVTVSS

EVQLVESGGGVVRPGGSLRLSCAASGFTFXXYAXSWVRQAPGKGLEWVSDISWSGSNTNYADSVKGRFTISRDNAKNSLYLQMNSL

RAEDTALYHCAXAPLXXXXTFGVGSWGQGTLVTVSS

BCD-135 VL
         10        20        30        40        50        60        70        80
90        100
12345678901234567890123456789012345678901234567890123456789012345678901234567890123456
78901234567890123456
QTVVTQEPSLSVSPGGTVTLTCGLSSGTVTAINYPGWYQQTPGQAPRTLIYNTNTRHSGVPDRFSGSISGNKAALTITGAQAEDEA

DYYCALYMGNGGHMFGGGTK

QTVVTQEPSLSVSPGGTVTLTCGLSSGTVTAINYPGWYQQTPGQAPRTLIYNTNTRHSGVPDRFSGSISGNKAALTITGAQAEDEA

DYYCALYXGXGXHMFGGGTK
```

| | Sequence of signal positive AA mutants BCD-135 | | | | | |
|---|---|---|---|---|---|---|
| Name | HCDR1 | HCDR2 | HCDR3 | LCDR3 | Response | koff |
| Wild-BCD-135VH | FDDYAMS | DISWSGSNTNYADSVKG | CARAPLLLAMTFGVGS | CALYMGNGGHM | 0.0903 | 0.001313 |
| 1m-BCD-135VH | FANYAMS | DISWSGSNTNYADSVKG | CAKAPLLLATTFGVGS | CALYVGTGSHM | 0.0971 | 0.005323 |
| 2m-BCD-135VH | FNDYAMS | DISWSGSNTNYADSVKG | CAKAPLPLATTFGVGS | CALYTGTGSHM | 0.0505 | 0.006534 |
| 3m-BCD-135VH | FNNYAMS | DISWSGSNTNYADSVKG | CAKAPLLLATTFGVGS | CALYTGTGSHM | 0.0719 | 0.006463 |
| 4m-BCD-135VH | FANYAMS | DISWSGSNTNYADSVKG | CAKAPLPLATTFGVGS | CALYVGTGSHM | 0.0637 | 0.00594 |
| 5m-BCD-135VH | FKSYAIS | DISWSGSNTNYADSVKG | CAKAPLMLAATFGVGS | CALYYGTGSHM | 0.0623 | 0.003241 |
| 6m-BCD-135VH | FSTYAMS | DISWSGSNTNYADSVKG | CAKAPLVLAITFGVGS | CALYTGTGSHM | 0.0945 | 0.001475 |
| 7m-BCD-135VH | FADYAMS | DISWSGSNTNYADSVKG | CAKAPLPSAITFGVGS | CALYEGTGSHM | 0.0637 | 0.00594 |
| 8m-BCD-135VH | FNNYAMS | DISWSGSNTNYADSVKG | CAKAPLLLATTFGVGS | CALYTGTGSHM | 0.0548 | 0.001831 |

Example 17

Creation of Stable Cell Line, Production and Purification of Anti-PD-L1 Antibody A stable cell line of the monoclonal antibody BCD-135 producer was obtained with transfection by electroporation using the Neon Transfection System (Life Technologies) device of the parental suspension cell line CHO-S with vector constructs containing light and heavy chains of the antibody in an optimized ratio. Clonal lines with a high level of productivity (more than 1000 mg/L) were made using a ClonePix robotize platform (Molecular Devices) and preliminary stages of the minipool selection using antibiotics in different culturing formats. Productivity assay was performed using the Octet RED96 analytical system (Pall Life Sciences). DOE for the basic medium selection and incubation schedule was carried out using the Biomek FX robotics computer-based system (Beckman Coulter). To incubate the producer, serum-free media and feedings without animal proteins were used. The BCD-135 preparation for preclinical studies was carried out in a HyLone single-use bioreactor (Thermo Fisher Scientific) fermenter having a working volume of 50 l.

Culture liquid was clarified on Millistak C0HC depth filter (Merck-Millipore). The primary purification of the antibody from clarified CL was performed on an affinity sorbent with protein A. Specific elution of the target protein was carried out under acidic conditions pH 3.3 to 3.8 in glycine buffer. The resulting eluate was kept in an acidic pH for 30-60 minutes to inactivate viruses and then neutralized with 1M Tris-OH solution to pH 6.5 to 7.0. The final chromatographic purification in the breakthrough mode was carried out on the CaptoAdhere sorbent (GE HealthCare LifeSciences) to remove residual DNAs, production cell proteins, the cleaved ligand of the affinity sorbent, antibody aggregates and fragments. For this purpose, the protein solution was passed through a prepared sorbent, at a pH of 6.5-7.0 with a low conductivity (<3 mS/$cm^2$). The purified protein was subjected to antiviral filtration using a Viresolve PRO filter set (Millipore), concentration and diafiltration against a final buffer containing acetate buffer (pH 5.0-5.5) and trehalose. The concentration of the resulting protein was 50 mg/ml or more.

Example 18

In Silico Modeling of BCD-135 Antibody and Human PD-L1 Complex

Figure 14A:
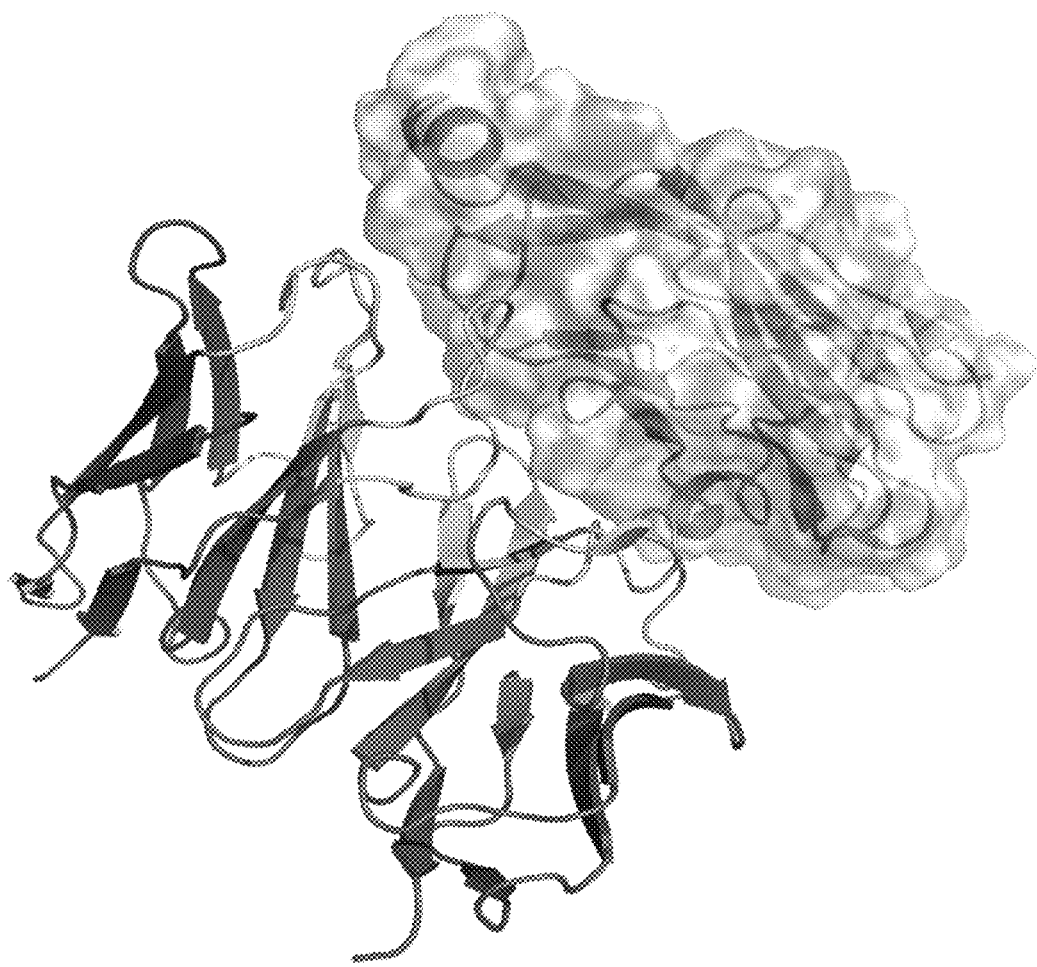
FIG. 14. 3D dimensional model of the complex between BCD-135 and N-terminus Ig domain of PD-L1 antigen. A is a general view of the 3D model; B is a detailed model in the region of direct antigen-antibody contacts (see table in Example 18).
Figure 14B:
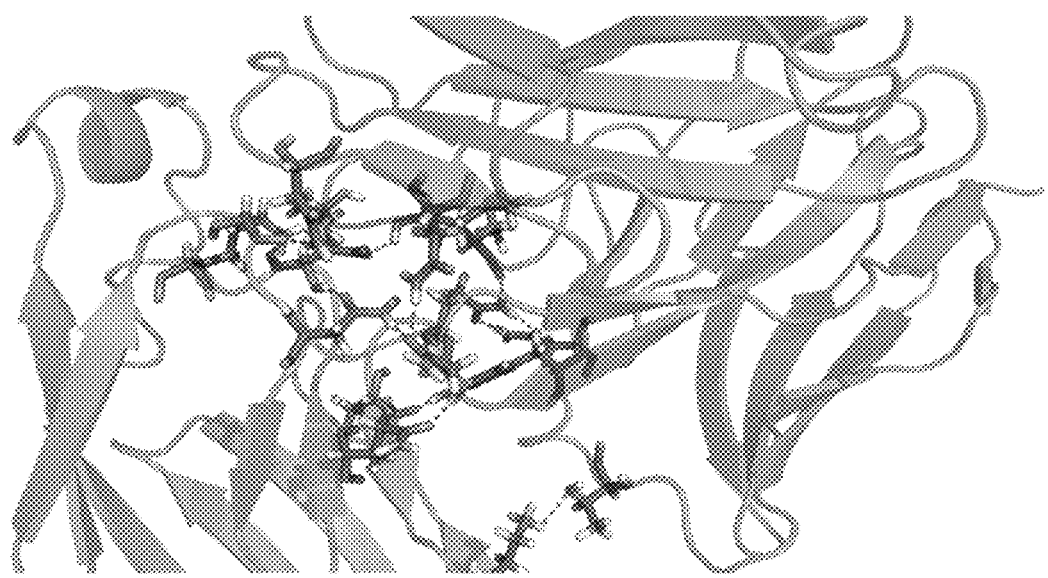

To create the BCD-135 mutant antibodies specific for PD-L1, a 3D modelling based structural analysis was carried out using Schrodinger Suite software from Schrodinger and YLAB package from BIOCAD. As the crystal structure of the target, PDB 5C3T was chosen because it has more crystallized amino acids than the classical 4ZQK structure where the emphasis is placed on the PD-1. The docking was performed using the HEDGE instrument (part of the YLab package from BIOCAD). The choice of optimal positions was made by estimating the free energy at the 10 nanosecond molecular dynamics interval (Desmond instrument, part of the Schrodinger Suite package). The visualization of the resulting structure was created using PyMOL instrument from Schrodinger. The model including the variable domains BCD-135 is shown in FIG. 14A, whereas FIG. 14B shows the region of antigen and antibody interaction with the isolated amino acid residues forming a tight inter-protein contact.

Table B presents the key amino acid residues of both antibody and antigen caused dense inter-protein interactions.

TABLE B

The middle column represents the amino acids residues of the BCD-135 antibody interacting with human PD-L1. The right column lists the corresponding amino acid residues of PD-L1 antigen interacting with the BCD-135 antibody.

| | Positions involved in interaction with human PD-L1 | Positions of human PD-L1 involved in interaction with BCD-135 |
|---|---|---|
| VH BCD-135 | N55 | G33 |
| | L99 | K105 |
| | M100a | D103 |
| | T100b | Q83 |
| VL BCD-135 | N50 | |
| | N94 | N35 |
| | Y32 | A85 |
| | T30a | K89 |
| | N94 | Q100 |

---

What is claimed is:

1. A monoclonal antibody or antigen binding fragment thereof that specifically binds to PD-L1, wherein
a heavy chain variable domain comprises CDR1, CDR2, CDR3, wherein CDR1 comprises the amino acid sequence of SEQ ID NO: 1, CDR2 comprises the amino acid sequence of SEQ ID NO: 2 and CDR3 comprises the amino acid sequence of SEQ ID NO: 3; and
a light chain variable domain comprises CDR1, CDR2, CDR3 wherein CDR1 comprises the amino acid sequence of SEQ ID NO: 5, CDR2 comprises the amino acid sequence of SEQ ID NO: 6 and CDR3 comprises the amino acid sequence of SEQ ID NO: 7.

2. The monoclonal antibody or the antigen binding fragment thereof according to claim 1, wherein the heavy chain variable domain comprises an amino acid sequence that is at least 90% identical to SEQ ID NO: 4.

3. The monoclonal antibody or the antigen binding fragment thereof according to claim 1, wherein the heavy chain variable domain comprises the amino acid sequence of SEQ ID NO: 4.

4. The monoclonal antibody or the antigen binding fragment thereof according to claim 1, wherein the light chain variable domain comprises an amino acid sequence that is at least 90% identical to SEQ ID NO: 8.

5. The monoclonal antibody or the antigen binding fragment thereof according to claim 1, wherein the light chain variable domain comprises the amino acid sequence of SEQ ID NO: 8.

6. The monoclonal antibody or the antigen binding fragment thereof according to claim 1, wherein
the heavy chain variable domain comprises an amino acid sequence that is at least 90% identical to SEQ ID NO: 4; and
the light chain variable domain comprises an amino acid sequence that is at least 90% identical to SEQ ID NO: 8.

7. The monoclonal antibody or the antigen binding fragment thereof according to claim 1, wherein
the heavy chain variable domain comprises the amino acid sequence of SEQ ID NO: 4; and
the light chain variable domain comprises the amino acid sequence of SEQ ID NO: 8.

8. The monoclonal antibody according to claim 1, comprising:
the heavy chain comprising an amino acid sequence that is at least 90% identical to SEQ ID NO: 9; and
the light chain comprising an amino acid sequence that is at least 90% identical to SEQ ID NO: 10.

9. The monoclonal antibody according to claim 1, wherein:
the heavy chain comprises the amino acid sequence of SEQ ID NO: 9; and
the light chain comprises the amino acid sequence of SEQ ID NO: 10.

10. The monoclonal antibody according to claim 1, wherein the antibody that specifically binds to PD-L1 is a full-length IgG antibody.

11. The monoclonal antibody according to claim 10, wherein the full-length IgG antibody is an isotype of human antibody IgG1, IgG2, IgG3, IgG4.

12. A pharmaceutical composition for relieving a disease or disorder mediated by PD-L1, comprising the antibody or the antigen binding fragment according to claim 1 and one or more pharmaceutically acceptable excipients.

13. The pharmaceutical composition according to claim 12 for relieving a disease or disorder mediated by PD-L1, wherein the disease or disorder mediated by PD-L1 is one of: SCCHN (squamous cell carcinoma of the head and neck), cervical cancer, cancer of unknown primary origin, glioblastoma, esophageal cancer, bladder cancer, TNBC (triple-negative breast cancer), CRC (colorectal cancer), hepatocellular carcinoma, melanoma, NSCLC (non-small-cell lung cancer), kidney cancer, ovarian cancer, Hodgkin's lymphoma, MSI-H CRC (high microsatellite instability colorectal cancer).

14. A method of relieving a PD-L1 mediated disease or disorder in a subject, comprising administrating to the subject a therapeutically effective amount of the pharmaceutical composition of claim 12.

15. The method according to claim 14, wherein the disease or disorder is one of: SCCHN (squamous cell carcinoma of the head and neck), cervical cancer, cancer of unknown primary origin, glioblastoma, esophageal cancer, bladder cancer, TNBC (triple-negative breast cancer), CRC (colorectal cancer), hepatocellular carcinoma, melanoma, NSCLC (non-small-cell lung cancer), kidney cancer, ovarian cancer, Hodgkin's lymphoma, MSI-H CRC (high microsatellite instability colorectal cancer).

16. A pharmaceutical combination for relieving a disease or disorder mediated by PD-L1, comprising the antibody or the antigen binding fragment according to claim 1 and at least one therapeutic antitumor compound.

17. The pharmaceutical combination according to claim 16 for relieving a disease or disorder mediated by PD-L1, wherein the disease or disorder mediated by PD-L1 is one of: SCCHN (squamous cell carcinoma of the head and neck), cervical cancer, cancer of unknown primary origin, glioblastoma, esophageal cancer, bladder cancer, TNBC (triple-negative breast cancer), CRC (colorectal cancer), hepatocellular carcinoma, melanoma, NSCLC (non-small-cell lung cancer), kidney cancer, ovarian cancer, Hodgkin's lymphoma, MSI-H CRC (high microsatellite instability colorectal cancer).

18. A method for inhibiting of biological activity of PD-L1 in a subject in need thereof, comprising administrating to the subject a therapeutically effective amount of the antibody or the antigen binding fragment as defined in claim 1.

19. A method of relieving a PD-L1 mediated disease or disorder in a subject, comprising administrating to the subject a therapeutically effective amount of the antibody or the antigen binding fragment of claim 1.

20. The method according to claim 19, wherein the disease or disorder is one of: SCCHN (squamous cell carcinoma of the head and neck), cervical cancer, cancer of unknown primary origin, glioblastoma, esophageal cancer, bladder cancer, TNBC (triple-negative breast cancer), CRC (colorectal cancer), hepatocellular carcinoma, melanoma, NSCLC (non-small-cell lung cancer), kidney cancer, ovarian cancer, Hodgkin's lymphoma, MSI-H CRC (high microsatellite instability colorectal cancer).

21. A monoclonal antibody or antigen binding fragment thereof that specifically binds to PD-L1 comprising:
- a) a heavy chain variable domain comprising the amino acid sequences corresponding to SEQ ID NO: 1, 2 and 3; a light chain variable domain comprising the amino acid sequences corresponding to SEQ ID NO: 5, 6 and 7; or
- b) a variant of a) comprising a combination of amino acid substitutions selected from the following group:
  - i) the first amino acid of SEQ ID NO: 1 is A, the second amino acid of SEQ ID NO: 1 is N, the seventh amino acid of SEQ ID NO: 3 is T, the fourth amino acid of SEQ ID NO: 7 is V, the sixth amino acid of SEQ ID NO: 7 is T and the eighth amino acid of SEQ ID NO: 7 is S;
  - ii) the first amino acid of SEQ ID NO: 1 is N, the fourth amino acid of SEQ ID NO: 3 is P, the seventh amino acid of SEQ ID NO: 3 is T, the fourth amino acid of SEQ ID NO: 7 is T, the sixth amino acid of SEQ ID NO: 7 is T and the eighth amino acid of SEQ ID NO: 7 is S;
  - iii) the first amino acid of SEQ ID NO: 1 is N, the second amino acid of SEQ ID NO: 1 is N, the seventh amino acid of SEQ ID NO: 3 is T, the fourth amino acid of SEQ ID NO: 7 is T, the sixth amino acid of SEQ ID NO: 7 is T and the eighth amino acid of SEQ ID NO: 7 is S;
  - iv) the first amino acid of SEQ ID NO: 1 is A, the second amino acid of SEQ ID NO: 1 is N, the fourth amino acid of SEQ ID NO: 3 is P, the seventh amino acid of SEQ ID NO: 3 is T, the fourth amino acid of SEQ ID NO: 7 is V, the sixth amino acid of SEQ ID NO: 7 is T and the eighth amino acid of SEQ ID NO: 7 is S;
  - v) the first amino acid of SEQ ID NO: 1 is K, the second amino acid of SEQ ID NO: 1 is S, the fifth amino acid of SEQ ID NO: 1 is I, the fourth amino acid of SEQ ID NO: 3 is M, the seventh amino acid of SEQ ID NO: 3 is A, the fourth amino acid of SEQ ID NO: 7 is Y, the sixth amino acid of SEQ ID NO: 7 is T and the eighth amino acid of SEQ ID NO: 7 is S;
  - vi) the first amino acid of SEQ ID NO: 1 is S, the second amino acid of SEQ ID NO: 1 is T, the fourth amino acid of SEQ ID NO: 3 is V, the seventh amino acid of SEQ ID NO: 3 is I, the fourth amino acid of SEQ ID NO: 7 is T, the sixth amino acid of SEQ ID NO: 7 is T and the eighth amino acid of SEQ ID NO: 7 is S;
  - vii) the first amino acid of SEQ ID NO: 1 is A, the fourth amino acid of SEQ ID NO: 3 is P, the fifth amino acid of SEQ ID NO: 3 is S, the seventh amino acid of SEQ ID NO: 3 is I, the fourth amino acid of SEQ ID NO: 7 is E, the sixth amino acid of SEQ ID NO: 7 is T and the eighth amino acid of SEQ ID NO: 7 is S; and
  - viii) the first amino acid of SEQ ID NO: 1 is N, the second amino acid of SEQ ID NO: 1 is N, the seventh amino acid of SEQ ID NO: 3 is T, the fourth amino acid of SEQ ID NO: 7 is T, the sixth amino acid of SEQ ID NO: 7 is T and the eighth amino acid of SEQ ID NO: 7 is S.

* * * * *

UNITED STATES PATENT AND TRADEMARK OFFICE
CERTIFICATE OF CORRECTION

| | |
|---|---|
| PATENT NO. | : 11,236,167 B2 |
| APPLICATION NO. | : 16/605865 |
| DATED | : February 1, 2022 |
| INVENTOR(S) | : Andrei Borisovich Ulitin |

It is certified that error appears in the above-identified patent and that said Letters Patent is hereby corrected as shown below:

On the Title Page

1. On Page 3, Column 1, item (56), under 'OTHER PUBLICATIONS', Line 17, delete "evleopment" and insert -- development --.

In the Specification

2. In Column 2, Line 44, delete "product" and insert -- produce --.
3. In Column 4, Line 25, delete "transplated" and insert -- transplanted --.
4. In Column 10, Line 41, delete "is" and insert -- are --.
5. In Column 13, Line 14, delete "neuravidin)." and insert -- neutravidin). --.
6. In Column 14, Line 24, delete "spectrophometer" and insert -- spectrophotometer --.
7. In Column 14, Line 31, delete "octetm" and insert -- octetTM --.
8. In Column 14, Line 65, delete "spectrophometer" and insert -- spectrophotometer --.
9. In Column 17, Line 10, delete "ImMunoGeneTic" and insert -- Immunogenetics --.
10. In Column 18, Line 43 delete "and" and insert -- "end" --.
11. In Column 38, Line 40, after "fragments" insert -- to --.
12. In Column 47, Line 25, delete "spirogermaraium;" and insert -- proherbarium; --.
13. In Column 47, Line 29, delete "gacytosine;" and insert -- cytosine; --.
14. In Column 47, Line 39, delete "leucovovin;" and insert -- leucovirin; --.
15. In Column 47, Line 60, delete "orafenib," and insert -- sorafenib, --.
16. In Column 48, Line 3, delete "leucovovin." and insert -- leucovirin. --.
17. In Column 49, Line 44, delete "schedule" and insert -- schedules --.
18. In Column 57, Line 52, delete "OctetRed" and insert -- Octet Red --.

In the Claims

19. In Column 72, Claim 13 Line 27, after "claim 12" insert -- , --.
20. In Column 72, Claim 17 Line 56, after "claim 16" insert -- , --.

Signed and Sealed this
Fifteenth Day of November, 2022

Katherine Kelly Vidal
*Director of the United States Patent and Trademark Office*